United States Patent
Kim

(10) Patent No.: US 6,210,423 B1
(45) Date of Patent: Apr. 3, 2001

(54) BONE MARROW SHIELDING APPARATUS AND METHOD OF BONE MARROW-SHIELDED CANCER CHEMOTHERAPY

(76) Inventor: Sinil Kim, 548 Ford Ave., Solana Beach, CA (US) 92075

( * ) Notice: Subject to any disclaimer, the term of this patent is extended or adjusted under 35 U.S.C. 154(b) by 0 days.

(21) Appl. No.: 09/239,511

(22) Filed: Jan. 28, 1999

Related U.S. Application Data

(60) Provisional application No. 60/080,817, filed on Apr. 6, 1998, provisional application No. 60/075,128, filed on Feb. 14, 1998, provisional application No. 60/074,002, filed on Feb. 9, 1998, and provisional application No. 60/073,004, filed on Jan. 29, 1998.

(51) Int. Cl.[7] .......................... A61B 17/00; A61M 29/00
(52) U.S. Cl. ........................................ 606/203; 128/898
(58) Field of Search ................................. 606/203, 201, 606/202, 204–204.15; 128/898, 899

(56) References Cited

U.S. PATENT DOCUMENTS

| | | | |
|---|---|---|---|
| 2,811,970 | 11/1957 | Hipps et al. | 128/327 |
| 3,032,033 | 5/1962 | Ramirez | 128/90 |

(List continued on next page.)

FOREIGN PATENT DOCUMENTS

| | | | |
|---|---|---|---|
| 821 824 | 11/1951 | (DE) . | |
| 8610887 | 6/1986 | (DE) | A61F/5/01 |
| WO 90/11744 | 10/1990 | (WO) | A61F/13/00 |

OTHER PUBLICATIONS

Conrad and Crosby, "Massive Nitrogen Mustard Therapy in Hodgkin's Disease with Protection of Bone Marrow by Tourniquets," *Blood*, 16:1089–1103 (1960).

(List continued on next page.)

*Primary Examiner*—Michael Buiz
*Assistant Examiner*—(Vikki) Hoa B. Trinh
(74) *Attorney, Agent, or Firm*—Gray Cary Ware & Freidenrich; June M. Learn

(57) ABSTRACT

The invention provides a variety of bone marrow-shielding tourniquets and methods for using them to perform bone marrow-shielded chemotherapy with or without general and without the need to remove a patient's bone marrow for protection during the procedure. In the invention method, pressure is applied to at least one body part of the patient that contains myelopoietic bone marrow to temporarily occlude arterial flow to the bone marrow while blood circulation through the remainder of the body is maintained. Then an effective amount of at least one myelosuppresive chemotherapeutic agent is administered to the blood circulation in the remainder of the patient while the arterial flow through the at least one body part is occluded and so that the myelosuppresive effect of the agent is substantially dissipated within the maximum safe period for the occlusion of the arterial flow, or about three hours. The pressure is removed to restore blood circulation to the bone marrow when the effect has substantially dissipated and within the maximum safe period. By the invention method, a tumor located in the remainder of the body is treated by the at least one chemotherapeutic agent without destruction of a substantial portion of the bone marrow in the occluded body part. The bone marrow shielding tourniquets for use in the invention chemotherapeutic method are designed to substantially cover at least the shoulder or hip area of a human so as to occlude arterial flow therein and include inflatable bladders that apply the requisite pressure when the tourniquet is applied to the wearer. The shoulder tourniquet optionally is designed to occlude arterial flow into the proximal scapula as well as into the shoulder area. Bilateral tourniquets are also provided for simultaneous occlusion of bilateral shoulders and, optionally, bilateral scapulae.

40 Claims, 29 Drawing Sheets

U.S. PATENT DOCUMENTS

| | | | |
|---|---|---|---|
| 3,454,010 | 7/1969 | Lilligren et al. | 128/327 |
| 4,210,147 | 7/1980 | Nestor et al. | 128/327 |
| 4,228,792 | 10/1980 | Rhys-Davies | 128/24.3 |
| 4,240,415 | 12/1980 | Wartman | 128/90 |
| 4,329,997 | 5/1982 | de Yampert et al. | 128/402 |
| 4,372,297 | 2/1983 | Perlin | 128/64 |
| 4,469,099 | 9/1984 | McEwen | 128/327 |
| 4,635,635 | 1/1987 | Robinette-Lehman | 128/327 |
| 4,829,994 | 5/1989 | Kurth | 128/96.1 |
| 4,957,105 | 9/1990 | Kurth | 128/96.1 |
| 5,234,459 | 8/1993 | Lee | 606/203 |
| 5,263,473 | 11/1993 | McWhorter | 128/25 |
| 5,288,286 | 2/1994 | Davis et al. | 602/6 |
| 5,411,518 | 5/1995 | Goldstein et al. | 606/202 |
| 5,454,831 | 10/1995 | McEwen | 606/202 |
| 5,486,194 * | 1/1996 | Kawasaki et al. | 606/203 |
| 5,496,358 | 3/1996 | Rosenwald | 607/108 |
| 5,514,155 | 5/1996 | Daneshvar | 606/112 |
| 5,584,853 | 12/1996 | McEwen | 606/201 |
| B1 4,469,099 | 11/1992 | McEwen | 606/202 |

OTHER PUBLICATIONS

Duff et al., "High–Dose Nitrogen Mustard Therapy With Intermittent Aortic Occlusion," *British Medical Journal*, 2: 1523–1528 (1961).

Gaffney et al., "Hemodynamic Effects of Medical Anti–Shock Trousers (MAST Garment)," *The Journal of Trauma*, 21(11):931–937 (1981).

Heavner et al., "Interaction of Lidocaine and Hypothermia in Bier Blocks in Volunteers," *Anesth Analg*, 69:53–59 (1989).

Kaback et al., "MAST Suit Update," *JAMA*, 252(18):2598–2603 (1984).

Pesce et al., "Scalp Tourniquet In The Prevention Of Chemotherapy–Induced Alopecia," *The New England Journal of Medicine*, 298(21) (1978).

Solonen et al., "Metabolic Changes In The Upper Limb During Tourniquet Ischaemia," *Acta Orthop. Scandinav.*, 39:20–32 (1968).

Wilgis, S., "Observations on the Effects of Tourniquet Ischemia," *The Journal of Bone and Joint Surgery*, 53–A(7):1343–1346 (1971).

* cited by examiner

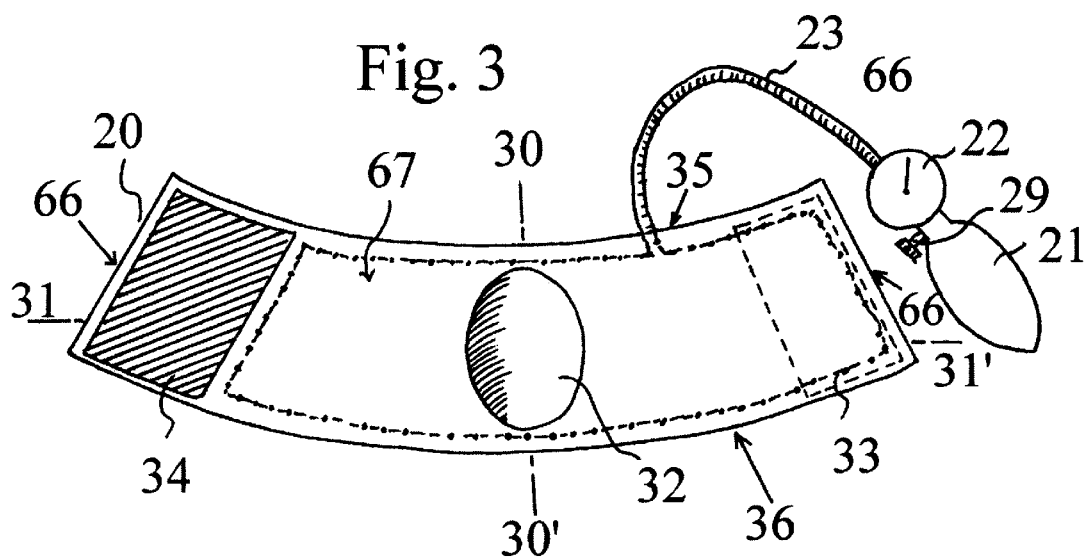
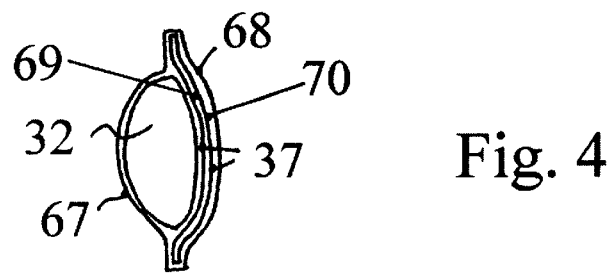
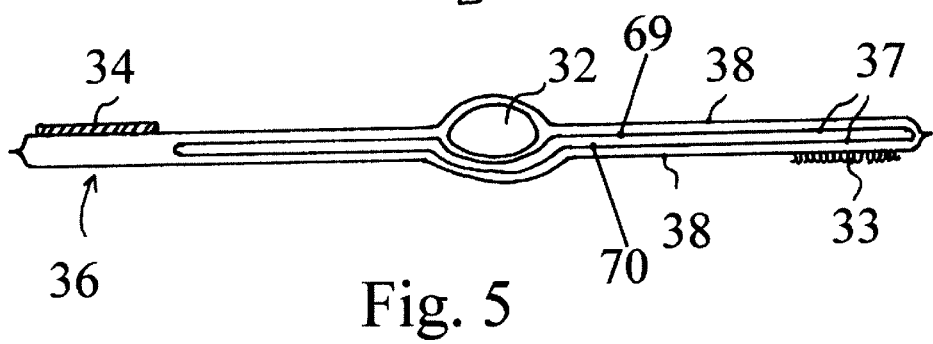

BONE MARROW SHIELDING APPARATUS AND METHOD OF BONE MARROW-SHIELDED CANCER CHEMOTHERAPY

RELATED APPLICATIONS

This application is a continuation-in-part of U.S. Provisional Patent Application Ser. No. 60/080,817, filed Apr. 6, 1998; U.S. Provisional Patent Application Ser. No. 60/075,128, filed Feb. 14, 1998, U.S. Provisional Patent Application Ser. No. 60/074,002, filed Feb. 9, 1998; and U.S. Provisional Patent Application Ser. No. 60/073,004, filed Jan. 29, 1998.

FIELD OF INVENTION

This invention pertains to an inflatable tourniquet-like apparatus or "bone marrow shield" useful for temporary occlusion of arterial flow into bone marrow of the limbs, shoulder girdle, or pelvic girdle during administration of cancer chemotherapy, and to a method of bone-marrow-shielded cancer chemotherapy in humans or mammals.

BACKGROUND OF THE INVENTION

One of the most serious side effects of cancer chemotherapy is myelosuppression—suppression of production of white blood cells, red cells, and platelets due to damage to the blood-forming elements of bone marrow in mammals. Myelosuppression can result in severe infections or bleeding and can result in death.

Currently, several strategies are employed to reduce this serious side effect. Granulocyte-colony stimulating factor (G-CSF), granulocyte-macrophage-colony stimulating factor (GM-CSF), stem cell factor (SCF), erythropoietin (EPO), thrombopoietin (TPO), or interleukin-11 (IL-11) is given to stimulate the bone marrow to produce more white blood cells, red cells or platelets. However, even with these bone marrow stimulating agents, chemotherapy doses cannot be high enough to have significant impact upon patient survival. Therefore, today autologous bone marrow transplant (ABMT) or peripheral blood stem cell (PBSC) transplant are relied upon to reconstitute severely damaged bone marrow. Both autologous bone marrow transplant and autologous peripheral stem cell transplant involve harvesting the patient's own hematopoietic cells, storing them outside the body while chemotherapy is administered to the patient, and then returning the previously-stored cells back to the patient after the chemotherapeutic agents have largely dissipated from the body. These methods provide the advantage of reducing the severity and duration of myelosuppression so that delivery of very high doses of chemotherapeutic agents can be administered.

However, these prior art methods are quite complicated and expensive to perform. Harvesting of a patient's bone marrow cells usually requires general anesthesia to perform multiple needle passes into bone marrow of pelvic bones. Harvesting of peripheral stem cells for PBSC transplant requires multiple apheresis procedures that are expensive and labor-intensive. The proper aseptic processing and freezing of harvested bone marrow cells and peripheral stem cells are also labor intensive and require highly trained laboratory personnel and special laboratory facilities. For these reasons, ABMT or PBSC transplant are not routinely performed in an ordinary oncologist's office making it difficult to perform multiple cycles of chemotherapy with ABMT or PBSC transplant.

To enable broad applicability to the general population of cancer patients, including those without access to expensive and sophisticated medical technologies, it is desirable to have an alternative method of reducing the myelosuppresive effect of chemotherapy that is both less costly and is simple enough to be performed in an ordinary oncologist's office. In addition, to derive the maximum benefit from cytotoxic agents, it is quite desirable to use a procedure that allows administration of multiple cycles of chemotherapy to the cancer patient.

Many cancers are confined to the trunk of the body. If it were possible to restrict arterial flow to the trunk of the body or to shield at least a portion of the myelopoietic bone marrow in the limbs while administering a chemotherapeutic agent to the remainder of the body, the need for removing a portion of the patient's bone marrow to preserve it from the effects of the chemotherapy could be avoided. Conrad et al. (*Blood*, 16:1089–103, 1960), almost 40 years ago, treated eight cancer patients using a procedure in which tourniquets were applied to three extremities (one arm plus two legs) for 15 minutes while nitrogen mustard was being administered. The chemotherapy involved administration of nitrogen mustard (1.0 to 1.5 mg/kg) under general anesthesia with endotracheal intubation in an operating room. Out of the eight patients treated, two patients died within three days, one from pulmonary embolism and the other from postoperative aspiration pneumonia. All six patients who survived more than three days postoperatively, suffered severe side effects, including headache, tinnitus and local thrombophlebitis, and three of the six patients suffered deafness. One patient died at 78 days post-operatively with internal and external hydrocephalus. The symptoms of the latter patient included aphasia, hemiparesis, papilledema, mental confusion, somnolence, and weakness.

Thus, this prior art method of chemotherapy generated severe side effects. The general anesthesia and intubation used in the study have risks, including aspiration pneumonia and pulmonary embolism, from which two of the eight patients succumbed within three days. Tourniqueting of the lower extremity may have also contributed to the fatal pulmonary embolism in one patient. Besides these side effects, the prior art method is expensive. General anesthesia and intubation are generally performed in an operating room and require presence of an anesthesiologist, artificial ventilation, and monitoring equipment, all of which significantly increase the cost of the chemotherapy treatment In addition, in adults most of the myelopoietic bone marrow in the upper and lower extremities is confined to the upper ⅓ of the humerus and femur. Since Conrad et al. appear to have used a common tourniquet applied in the usual tourniquet position to practice the prior art method of chemotherapy, it is likely that the myelopoietic bone marrow in the extremities of the patients treated was exposed to the myelosuppresive agent.

Almost 40 years ago in Africa, Duff et al. (*British Med J.*, 2:1523–8. 196 1) also treated patients under general anesthesia on an operating table in a chemotherapeutic method intended to protect the bone marrow from the myelosuppresive effects of the chemotherapeutic method. Sand bags were placed on the patient's abdomen, directly over the aorta, and then the patient's body was tightly wrapped with elastic Esmarch bandage while the chemotherapeutic agent was administered. The occlusion was maintained for 20 minutes and the treatment was repeated 48 hours later.

However, this prior art method of chemotherapy is useful for only a limited number of patients. External compression of the abdomen at a pressure high enough to occlude the aorta is only possible in thin patients and may damage delicate internal organs and anatomic structures in the abdomen and pelvis, such as the intestines, kidneys, bladder and ureters. Abdominal pressure high enough to occlude the aorta would also be likely to occlude the inferior vena cava, possibly causing formation of thrombus in the inferior vena cava or other veins in the pelvis and legs, especially in hypercoagulable cancer patients. In addition to the risks involved, the use of general anesthesia in Duff's method would make it expensive and difficult to apply in the modern era.

The tourniquets of prior art have design limitations which make them difficult to apply to the shoulder area or hip area. They have been designed to be applied to part of the limb which is largely cylindrical or conical, such as the upper arm or thigh areas. Since the areas of active bone marrow in limbs are normally limited to the proximal $1/3$ of the humerus and femur, blood circulation must be interrupted in the shoulder area or hip area, not just in the arm or leg area. However, the shoulder and hip areas are of complex three-dimensional shape, and tourniquets designed to apply a uniform pressure to these areas do not exist in prior art, as far as the Applicant is aware. Therefore, methods of tourniquet application and new tourniquet apparatus are needed that are designed for application to the shoulder and hip areas.

SUMMARY OF THE INVENTION

The present invention provides a method for bone marrow-shielded chemotherapeutic treatment of a cancer patient. The invention method comprises applying pressure to at least one body part of the patient that contains myelopoietic bone marrow to temporarily occlude arterial flow to the bone marrow while blood circulation through the remainder of the body is maintained, administering an effective amount of at least one myelosuppresive chemotherapeutic agent while the arterial flow through the at least one body part is occluded and so that the myelosuppresive effect of the agent is substantially dissipated within the maximum safe period for the occlusion of the arterial flow, and removing the pressure to restore blood circulation to the bone marrow when the effect has substantially dissipated and within the maximum safe period. By the invention method a tumor located in the remainder of the body is treated by the at least one chemotherapeutic agent without destruction of a substantial portion of the bone marrow in the at least one body part, and without general anesthesia.

In a presently preferred embodiment of the invention method, a bone marrow shielding tourniquet is used to apply pressure to at least one body part containing myelopoietic bone marrow so as to occlude arterial flow to the bone marrow therein. It is presently preferred that pressure is applied around one or both shoulders and/or hips of the patient so as to occlude arterial flow to the bone marrow in the upper $1/3$ of the proximal humerus or femur, for example by surrounding the shoulder(s) and/or hip(s) with a tourniquet such as is provided herein. The pressure applied (e.g., by the tourniquet) is substantially greater than the systolic blood pressure of the patient, for example from about 5 mmHg to about 300, above the systolic blood pressure to assure complete occlusion of arterial flow in the shoulder or hip to which the pressure is applied.

In another embodiment, the invention provides a bone marrow shielding tourniquet adapted to apply pressure around a shoulder or hip of a human. The invention bone marrow-shielding tourniquet comprises an inflatable bladder contoured for substantially covering the shoulder or hip of a human and having an inner face and an outer face, a fluid-tight connector on the inflatable bladder for attaching the bladder to a source of fluid pressure, and a substantially inelastic exterior layer substantially covering the outer face of the bladder so as to limit expansion of the bladder in the direction of the exterior layer when the bladder is inflated by fluid from the fluid source.

The human shoulder and hip are complex three-dimensional shapes, rather than substantially cylindrical, as is the arm or thigh. Consequently it is difficult to apply a tourniquet around these body parts so as to occlude arterial blood flow to the myelopoietic bone marrow residing therein. Therefore, the shape of the invention bone marrow-shielding tourniquet contributes substantially to its ability to apply pressure over the shoulder or hip area such that all the arteries that supply the proximal upper one third of the humerus or femur are occluded by the tourniquet. In some embodiments, the exterior layer is inflexible or semi-flexible and the invention tourniquet further comprises a cooperative fastener for fastening the tourniquet around the shoulder or hip and/or a brace to hold the patient's arm or thigh at an angle that facilitates placement of the tourniquet and prevention of migration of the tourniquet during chemotherapy.

In another embodiment, the invention provides a bilateral hard shell bone marrow shielding tourniquet adapted for wearing by a human. The invention hard shell bilateral tourniquet comprises a semi-flexible or inflexible and inelastic carapace in one or more parts, wherein the carapace has a three-dimensional shape adapted to substantially cover at least the bilateral scapulae and shoulder areas of a wearer while allowing the head, arms, and lower torso to protrude from the carapace. Optionally the bilateral tourniquet further comprises bilateral inflatable bladders attached along the interior surface of the carapace that, when inflated, apply pressure over at least the bilateral shoulder areas of the wearer, and a fluid-tight connector on each inflatable bladder for inflating the bladder. Inflation of one or both bladders in the invention hard shell bilateral tourniquet exerts sufficient pressure upon the respective shoulder area of the wearer to occlude arterial flow into at least the upper $1/3$ of the proximal humerus of the wearer. The invention bilateral hard shell tourniquet generally further comprises at least one fastener attached to the carapace for cinching the carapace about the torso of the wearer, for example the midriff and upper back. In one embodiment, the carapace is semi-flexible and in one piece with a neck/chest opening adapted for receiving the wearer's head and at least one opening, such as a slit, to enable the tourniquet to be placed about the wearer.

In another embodiment, the invention provides an inflatable bladder comprising an expandable bladder piece shaped to substantially cover a hip area or a shoulder area of a human, and a fluid-tight connector on the bladder for connecting the bladder to a source of fluid pressure. When the inflatable bladder is shaped to substantially cover a shoulder area, it may further substantially cover the proximal scapula of a human. The invention inflatable bladder, or two mirror image inflatable bladders, can be used with the invention hard shell tourniquet to shield a portion of a wearer's bone marrow during chemotherapy in accordance with the invention method of chemotherapy.

In another embodiment, the invention provides a hard shell bone marrow shielding tourniquet adapted for applying pressure to a scapular area of a human wearer. In this embodiment, the invention tourniquet comprises an inflatable bladder contoured for substantially covering the scapular area and having an inner face and an outer face, a fluid-tight connector attached to the inflatable bladder for attaching the bladder to a source of fluid pressure, a substantially inflexible and inelastic exterior layer substantially covering the outer face of the bladder and having a three-dimensional shape selected to hold the bladder against the scapular area of a human, and at least one fastener attached to the exterior layer for cinching the tourniquet about the torso of the wearer. In this embodiment of the invention tourniquet, inflation of the bladder by fluid from the fluid source exerts a pressure on the scapular area of the wearer sufficient to substantially occlude arterial flow into the scapular area of the wearer.

In another embodiment, the invention provides a method for fabricating an individualized bone marrow shielding tourniquet. The invention fabrication method comprises wrapping a hip or shoulder to be compressed for occlusion of arterial blood flow therein with an inflatable bladder having an attached air-tight tubing, wrapping the inflatable bladder with an orthopedic cast material so as to leave free the distal end of the attached tubing, and molding the cast material and inflatable bladder around the hip or shoulder under conditions suitable for causing the orthopedic cast material to harden into an inflexible hard shell.

It is, accordingly, one object of the present invention to provide a method for applying a tourniquet to one or both shoulders, hips, scapulas, or pelvic areas of a human body, for example, without general anesthesia, to enable temporary occlusion of arterial flow into myelopoietic bone marrow contained therein during administration of a chemotherapeutic agent.

Another objective of the present invention is to provide new tourniquets contoured to fit the shoulder or hip area of a human body.

Another objective of the present invention is to provide a contoured hard-shell tourniquet for shoulder or hip area of a human body.

Another objective of the present invention is to provide a method of making a custom-fitted hard-shell tourniquet for the shoulder or hip area of a human body.

Another objective of the present invention is to provide a new tourniquet that places and holds the limbs in a preferred position relative to the torso of a patient's body to effect compression of blood vessels that supply the proximal ends of femur or humerus bones.

Another objective of the present invention is to provide a new tourniquet with a binding system to affix the tourniquet at a preferred position at the shoulder or hip while preventing migration of tourniquet away from the preferred position on the shoulder or hip.

Another objective of the present invention is to provide a method of using the tourniquet to protect myelopoietic bone marrow cells from the effects of chemotherapeutic agents without the need for physical removal of bone marrow cells from the patient's body, i.e. without expensive apheresis or bone marrow aspiration procedures.

Another objective of the present invention is to provide a method of bone marrow-shielded chemotherapeutic treatment of a patient by administering one or more chemotherapeutic agents while protecting bone marrow cells in situ using a tourniquet to occlude arterial blood flow in the bone marrow, for example in one or both shoulders and hips.

Another objective of the present invention is to provide a method of bone marrow-shielded chemotherapeutic treatment of a patient using the tourniquet apparatus to administer one or more chemotherapeutic agents, in combination with bone-marrow stimulating factors.

Still another objective of the present invention is to provide a method of bone marrow-shielded chemotherapeutic treatment of a patient using the tourniquet apparatus in combination with administration of highly oxygenated autologous blood into an area of ischemia behind the tourniquet.

Still another objective of the present invention is to provide a method of bone marrow-shielded chemotherapeutic treatment of a patient using the tourniquet apparatus that includes chilling the limb behind the tourniquet to reduce metabolic rate and thereby decrease tissue damage caused by ischemia.

The invention also comprises such other objects, advantages, and capabilities as will later more fully appear and which are inherently possessed by the invention. While the accompanying drawings show certain embodiments of the invention, it should be understood that the same is susceptible of modification and change without departing from the spirit of the invention.

BRIEF DESCRIPTION OF DRAWINGS

FIG. 3 is an elevation view of an invention contoured shoulder tourniquet,

FIG. 4 is a cross-sectional view taken through line 30—30 of FIG. 3.

FIG. 5 is a cross-sectional view taken through line 31—31 of FIG. 3.

DETAILED DESCRIPTION OF THE PREFERRED EMBODIMENTS

Figure 1:
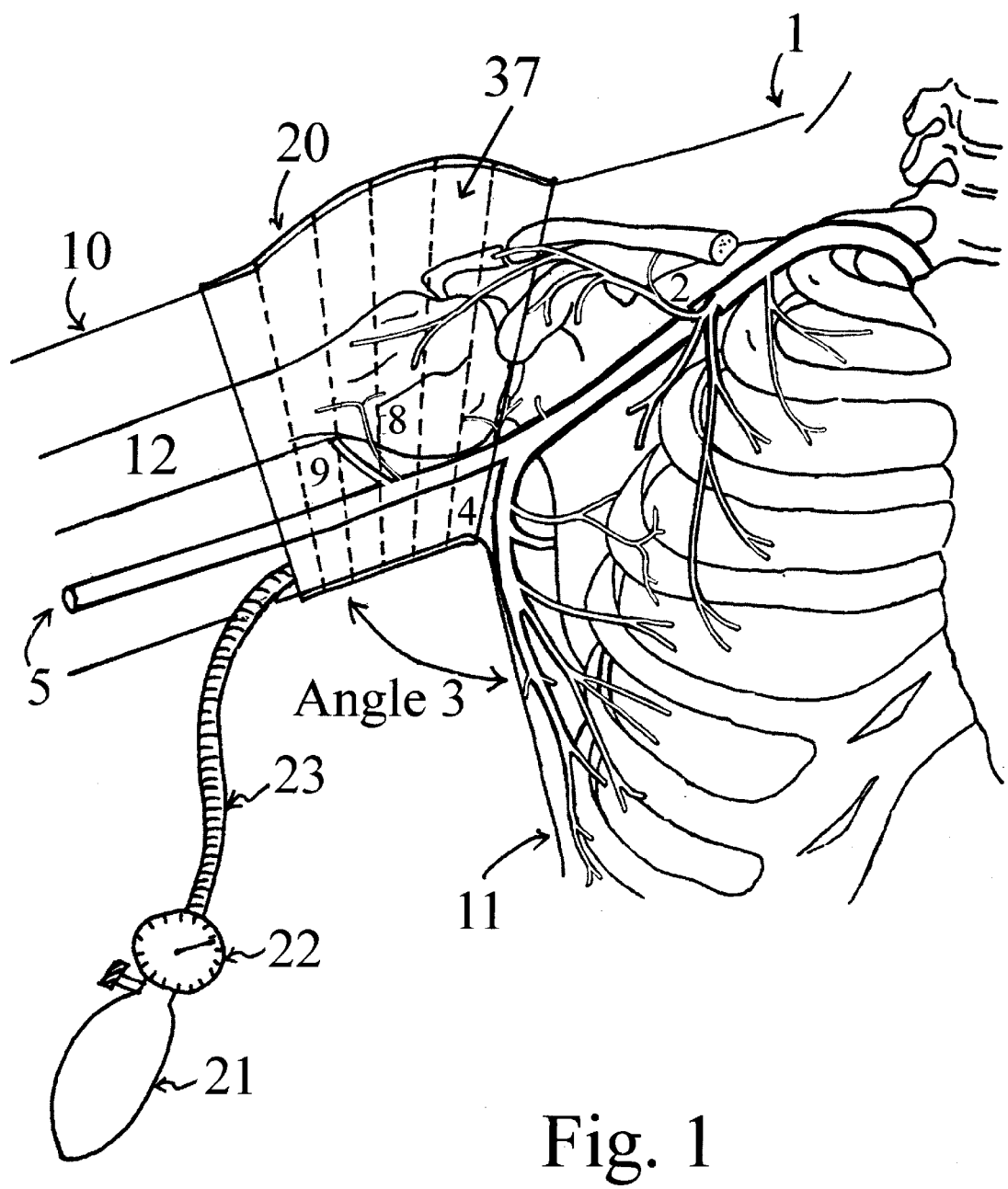
FIG. 1 is a see-through drawing showing preferred shoulder tourniquet placement with an invention shoulder tourniquet placed around the shoulder area of a patient such that all the arteries that supply the proximal end of the humerus are occluded by the tourniquet.

In adults, active marrow is located primarily in the axial skeleton, including the vertebral bodies, pelvis, sternum, ribs, scapulae, and to a variable extent, the skull. In the limbs, active bone marrow is restricted to the proximal one third of the femurs and humeri (with more peripheral extension of marrow seen in children). In fact, the proximal humerus contains hematopoietic marrow in 99% of adult patients, with some patchy extension to the epiphysis in 62% of adults. Surprisingly, the adult humerus contains a larger quantity of hematopoietic marrow than the femur, despite its smaller size.

Accordingly, in the present invention there are provided method(s) for bone marrow-shielded chemotherapeutic treatment of a patient in need thereof. The invention method (s) comprise applying pressure to at least one body part of the patient that contains myelopoietic bone marrow to temporarily occlude arterial flow to the bone marrow while blood circulation through the remainder of the body is maintained, administering to the blood circulation in the remainder of the body an effective amount of at least one myelosuppresive chemotherapeutic agent while the arterial flow through the at least one body part is occluded so that the myelosuppresive effect of the agent is substantially dissipated within the maximum safe period for the occlusion of arterial flow, and removing the pressure to restore blood circulation to the bone marrow when the effect has substantially dissipated and within the maximum safe period. By the invention method, a tumor located in the remainder of the body is treated by the at least one chemotherapeutic agent without destruction of a substantial portion of the bone marrow in the at least one body part. The invention method(s) can be practiced either with or without general anesthesia.

The term "substantially dissipated" as used herein means that the myelosuppresive effect of the chemotherapeutic agent has subsided sufficiently in the circulating blood that irreparable damage to a substantial portion of the bone marrow in the occluded body part will not occur when the blood circulation is restored to the body part. As those of skill in the art will appreciate, the period of time required for the chemotherapeutic (i.e., myelosuppresive) effect to be substantially dissipated will depend upon the pharmokinetics of the particular chemotherapeutic agent used, or of the combination of chemotherapeutic agents used, and can be selected by the skilled practitioner when taking into account such factors as the initial half-life and residual effects of the chemotherapeutic agent or combination of therapeutic agents, as well as the size and general health of the patient.

In a presently preferred embodiment of the invention method(s), a bone marrow shielding tourniquet is used to apply pressure to at least one body part that contains myelopoietic bone marrow so as to occlude arterial flow to the myelopoietic bone marrow. Use of the invention bone marrow shielding tourniquet in practice of the invention method(s) greatly facilitates practice of the methods with or without general anesthesia as explained more fully herein.

The most convenient body parts to be shielded during chemotherapy in a human adult are the shoulder and hip. The term "shoulder" or "shoulder area" as used in the description and claims herein means the part of the body formed by the lateral portions of a scapula and clavicle, at least the head of the proximal humerus, and the flesh covering them (including the areas commonly referred to as the shoulder cap and the arm pit). Similarly, the term "hip" or "hip area" as used in the description and claims herein means the part of the body formed by the pelvis, at least the head of the femur, and the flesh covering them (including the areas commonly referred to as the "hip bone" and groin). As used herein, the term "shoulder tourniquet" means a tourniquet shaped to conform to and fit around the shoulder area of a human so as to substantially cover the shoulder area, and the term "hip tourniquet" means a tourniquet apparatus shaped to conform to and fit around the hip area of a human so as to substantially cover the hip area. The term "scapula" or "scapular area" as used herein means the substantially flat, triangular bone commonly known as the shoulder blade and the flesh covering it, but does not necessarily include the spine. The term "nutrient artery" or nutrient arteries" as used herein means the arteries supplying blood into bone and bone marrow that enter the body (or shaft) of a long bone, in this case the humerus or femur. The arteries supplying the ends of the humerus and femur have individual names as provided herein.

The term "bone-marrow shielding" as used herein means a process of temporarily occluding arterial blood flow into a body part containing myelopoietic bone marrow, such as a shoulder or hip, for example, during administration of cancer chemotherapy. The term "occludes," "occluded" and "occluding" as used herein mean temporary occlusion of arterial blood flow into the affected body part. Whether arterial blood flow has been occluded in a shoulder or hip can be empirically determined by determining the absence of a pulse in the adjacent limb, for example the pulse of the dorsalis pedis artery in the foot or the radial artery in the wrist. The term "bone-marrow shield" is defined as an apparatus, such as an invention tourniquet, that performs bone-marrow shielding.

Preferably, the occluding pressure is applied to the body part using an inflatable, releasable tourniquet that occludes arterial flow to the body part, preferably completely, such as the invention tourniquet(s) described herein. However, the pressure is applied, it is essential that the pressure not be inadvertently released to allow arterial flow into the shielded bone marrow while the myelosuppresive effect of the chemotherapeutic agent(s) is substantially present in the circulating blood, as such an accident could result in serious injury to the patient. When the bone marrow shielding pressure is applied to a shoulder area, it is therefore essential that arterial flow into the proximal upper ⅓ of the humerus of the patient be substantially occluded, preferably completely occluded. Similarly, when the bone marrow shielding pressure is applied to a hip area, it is essential that arterial flow into the proximal upper ⅓ of the femur of the patient be substantially occluded, preferably completely.

Figure 8:
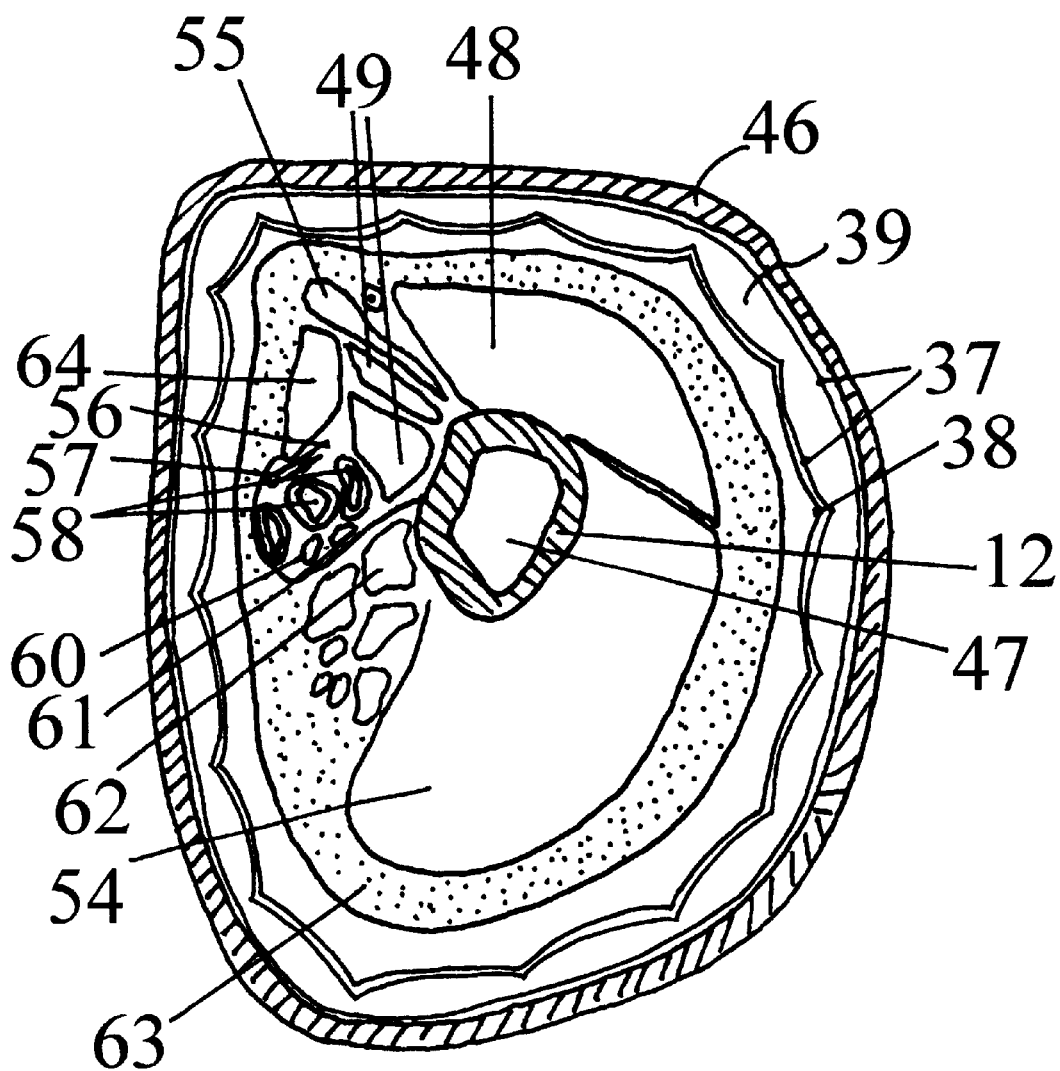
FIG. 8 is a cross-sectional view of an invention hard-shell tourniquet with an inflatable bladder at the beginning of the inflation.
Figure 9:
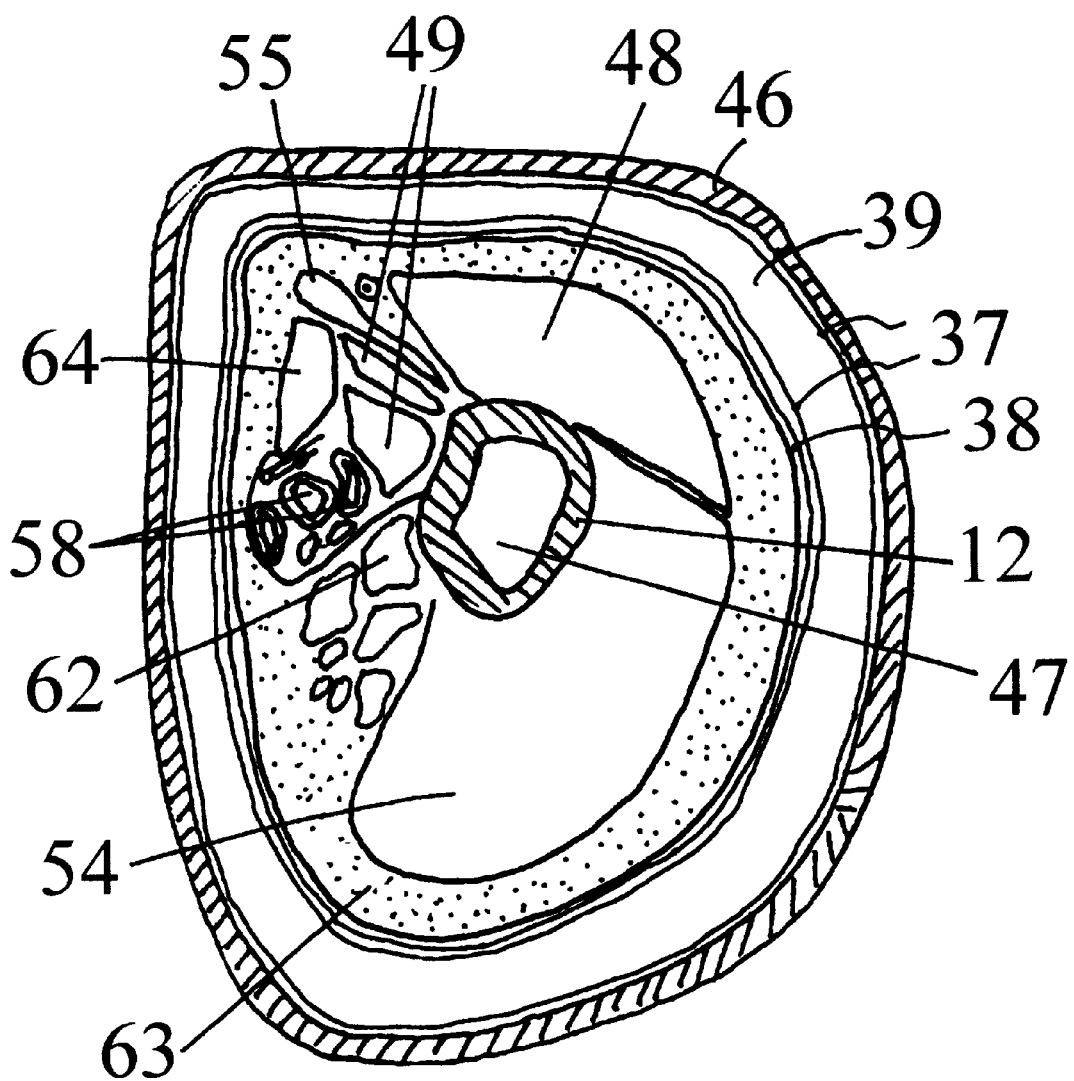
FIG. 9 is a cross-sectional view of an invention hard-shell tourniquet with an inflatable bladder inflated further than in FIG. 8.

Since bone marrow shielding of the shoulder or hip areas requires substantial occlusion of the arteries into these body parts, the invention is best understood by reference to the anatomy of the body parts to be shielded. FIG. 1 illustrates cancer patient 1 with an arm 10 in a preferred elevated position with shoulder tourniquet 20 placed in a preferred shoulder area location. For the upper limb, the arteries supplying the upper end of the humerus 12 include anterior and posterior humeral circumflex arteries 8 and 9, which are typically the last branch of the axillary artery 4, which is the direct continuation of the subclavian artery. The deltoid branch of thoraco-acromial artery 2 also supplies the upper end of the humerus in some patients. The nutrient artery of the humerus is a thin branch that arises from the brachial artery 5 about the middle of the upper arm and enters the anteromedial surface of the middle third part of the humerus. To interrupt blood circulation into the upper humerus it is critical for the tourniquet to compress not only the main artery supplying the limb (axillary artery 4 which continues on as brachial artery 5), but also smaller branch arteries of the upper humerus, such as the anterior and posterior humeral circumflex arteries 8 and 9 and the deltoid branch of thoraco-acromial artery 2. FIGS. 8 and 9 show cross-sections through the upper humerus bone with an invention shoulder tourniquet in position before and after inflation, respectively.

The tourniquet compresses the main artery, brachial artery 58 against the humerus to occlude arterial flow, but median nerve 57, ulnar nerve 60 and radial nerve 61 will also be compressed against the humerus. It is important to the practice of the invention that the pressure applied to occlude arterial flow into the upper humerus be as evenly distributed over the surface of the shoulder area as possible to avoid damage to these nerves. Therefore, in the invention method(s) the pressure is preferably applied over the entire shoulder area and the pressure applied, for example by a tourniquet, is preferably substantially equalized over the shoulder area. Similarly, the invention bone marrow-shielding shoulder tourniquet is contoured to extend over the shoulder area so as to substantially equalize the pressure applied to the delicate nerves and arteries within the shoulder area.

It is preferred that the arm 10 is in an elevated position to enable preferred placement of tourniquet 20 in shoulder area when the invention shoulder tourniquet is used in practice of the invention bone marrow shielded chemotherapy method. Therefore, as shown in FIG. 1, the angle 3 formed by the patient's arm 10 and the proximal side of the patient's torso 11 is preferably between 45 degrees and 180 degrees, more preferably between 75 degrees and 160 degrees, and most preferably between 85 degrees and 140 degrees in practice of the invention method.

Figure 15:
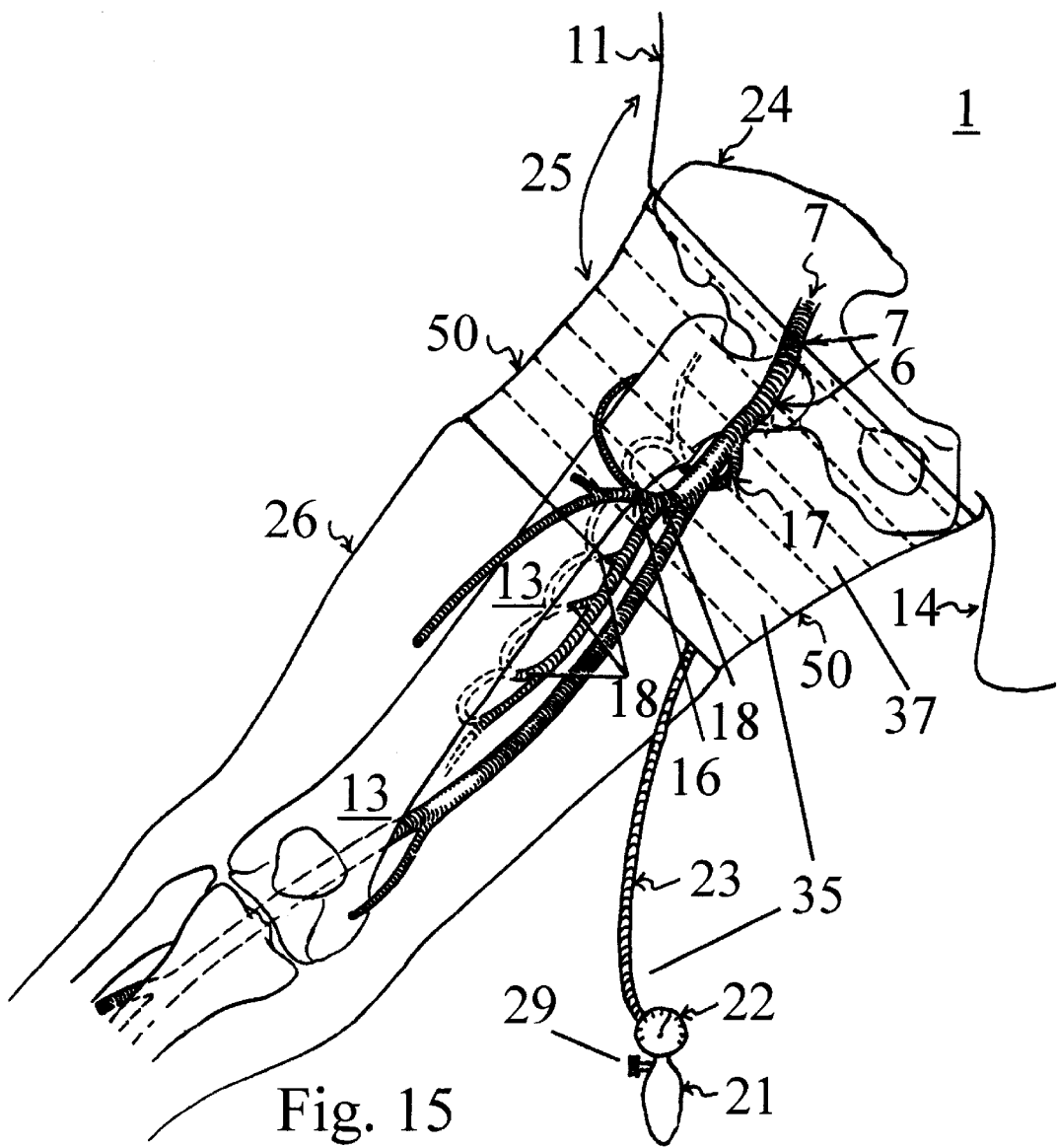
FIG. 15 is a see-through drawing showing tourniquet placement with an invention hip tourniquet placed around the hip area of a patient such that all the arteries that supply the proximal end of the femur are occluded by the tourniquet.
Figure 16:
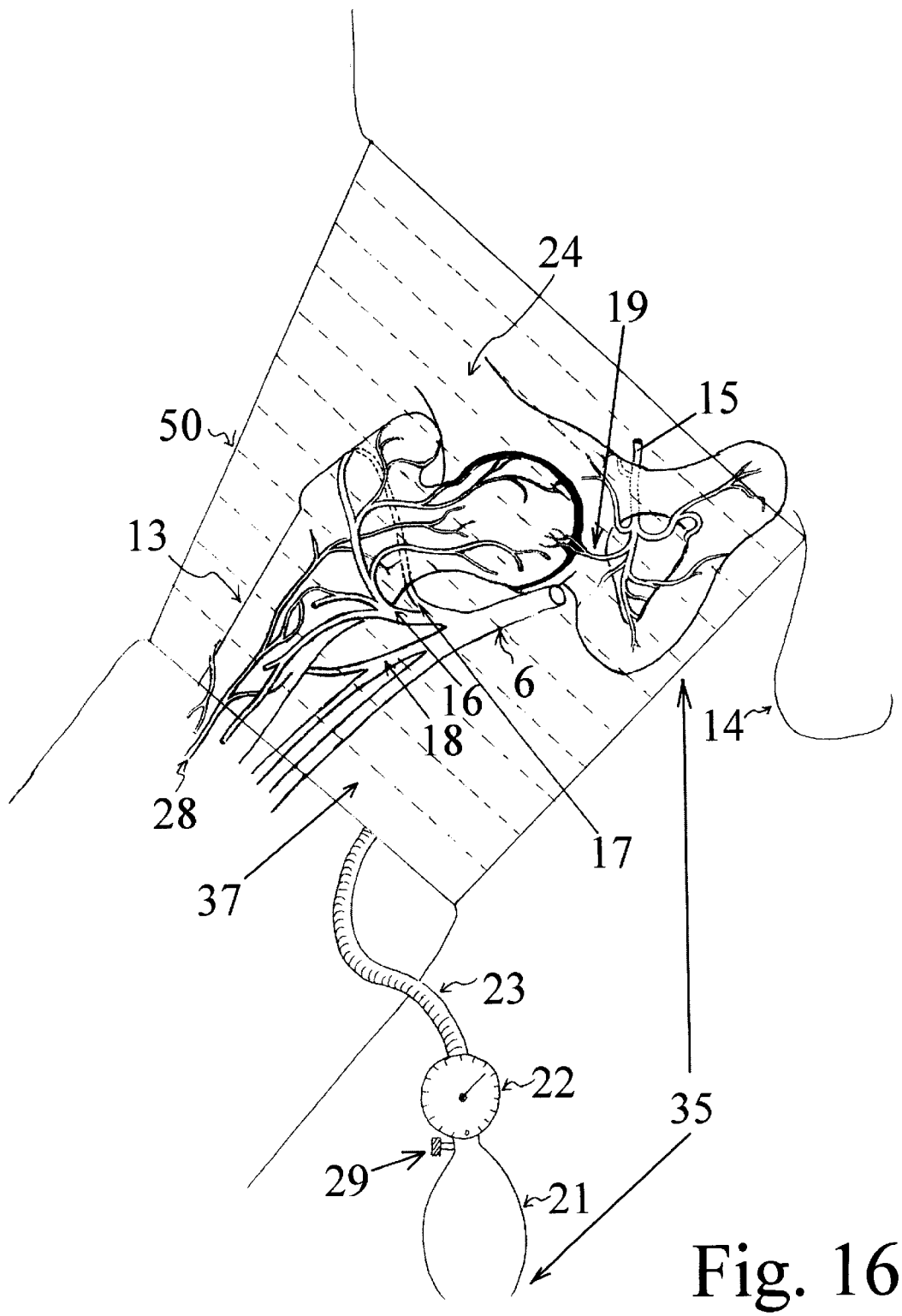
FIG. 16 is another see-through drawing showing tourniquet placement with an invention hip tourniquet placed around the hip area of a patient and showing details of arteries that supply the proximal end of the femur.

The anatomy of the hip area, is illustrated in FIGS. 15 and 16, which show the blood supply of the femur 13 consisting of multiple arteries entering each end of the femur, and one or two nutrient arteries entering the body or shaft of the femur. The nutrient arteries are usually derived from upper perforating branches of the profunda femoris 18; and they enter the femur close to the linea aspera and run up and down in the marrow cavity. Although the nutrient arteries in the femur anastomose with the vessels at the two ends of the femur, the upper perforating branches of the profunda femoris 18 are the chief supply of nutrients to the human femur.

The arteries to the upper end of the femur are derived mostly from the medial 17 and lateral 16 femoral circumflex arteries; which provide numerous branches to the trochanters. The artery of the ligament of the femoral head, derived from the obturator 15 (see FIG. 16) or the medial femoral circumflex 17, enters the head through the ligament of the head and supplies a variable amount of bone adjacent to the fovea. Otherwise, the head and neck are supplied by branches of the two circumflexes 16 and 17. These branches approach the bone at the level of attachment of the capsule of the hip joint, pierce the capsule, and then run upward along the neck deep into the synovial membrane that is reflected upward around the neck to the cartilage of the head. To occlude arterial circulation into the upper femur, it is important for the tourniquet to compress not only the main femoral artery 6, but the smaller branches that supply the upper femur such as the medial and lateral femoral circumflex arteries 16 and 17 and the artery of the ligament of the head 19.

The scapulae of adult humans also contain myelopoietic bone marrow. Therefore, in an alternative embodiment of the invention method(s), a bone marrow shielding pressure is applied to one or both scapulae in a manner that occludes arterial flow thereinto. There are three main arteries that supply the scapulae. The first is the suprascapular artery, which arises from the thyrocervical trunk in the neck. The suprascapular artery courses backward above the scapular notch on the superior border of the scapula and supplies blood to the back (dorsal) surface (facie) of the scapula. The second is the subscapular artery, which arises from the axillary artery. The subscapular artery supplies the front (costal) surface of the scapula and then branches into the scapular circumflex artery, which swings around the lower border of the scapula and supplies arterial blood to the back (dorsal) surface of the scapula. The third is the transverse cervical artery, which also arises from the thyrocervical trunk in the neck. The transverse cervical artery runs along the medial margin of the scapula and supplies both the back (dorsal) and front (costal) surfaces of the scapula. Application of sufficient pressure over the back (dorsal) surface of the scapula will compress the arteries supplying the back surface of the scapula. Such a pressure upon the back surface of the scapula can transmit the pressure to the posterior rib cage, further compressing the arteries between the front surface of the scapula and the rib cage.

Therefore, in practice of the invention method, the at least one body part is selected from the group consisting of an upper femur, an upper humerus, and a scapula of the patient, and combinations of two or more thereof.

To assure that arterial flow is substantially occluded to the bone marrow to be shielded, the pressure applied, for example by the invention tourniquet, is substantially greater than the systolic blood pressure of the patient, preferably at the point of application of the tourniquet, for example from about 5 mmHg to about 300 mmHg above the systolic blood pressure, such as from about 20 mmHg to about 250 mmHg, and preferably about 50 mmHg to about 200 mmHg above systolic blood pressure. Alternatively, pressure of about 280 mmHg may be used. Preferably, the tourniquet is applied around or over the body part so that the occluding pressure is substantially equalized over the entire area.

Once the pressure has been applied, and occlusion of arterial flow is assured, one or more chemotherapeutic agents selected to treat the type of tumor under treatment can be administered, for example, by injection of the chemotherapeutic agent(s) into the blood circulation to treat a tumor that lies within the trunk or within any part of the body in which the circulation of blood has been maintained. Any myelosuppresive chemotherapeutic agent known in the art can be safely administered in the standard dosage, or in a higher dosage, so long as the myelosuppresive effect of the agent(s) is substantially dissipated before removal of the occluding pressure and any non-myelosuppresive side-effect is not dose-limiting. Given the present understanding in the medical arts concerning methods for extending the maximum safe period, the arterial flow can be occluded before irreversible cell damage to the occluded body part (e.g., extremity) occurs, the occluding pressure is removed in practice of the invention method within the maximum safe period for occluding arterial flow, generally about three hours, or preferably two hours, of commencement of the application of the occluding pressure to the body part.

Therefore the chemotherapeutic agent(s) are selected to have the property that their myelosuppresive effect will be substantially dissipated before the occluded body part sustains irreversible damage caused by the occlusion.

Generally, the chemotherapeutic agent or combination of chemotherapeutic agents is selected to have a half life of from about 10 seconds to about 25 minutes. However, many chemotherapeutic agents continue to have myelosuppresive effect for a period equal to three or more half-lives, and their chemotherapeutic effect is generally maximized when the activity of the agent(s) is allowed to substantially dissipate by the natural operation of bodily processes, as is known to those of skill in the art. Therefore in practice of the invention method the general rule is that the chemotherapeutic agents used are selected and the method of administration (i.e. whether bolus, drip or infusion) is selected so that the myelosuppresive effect of the agent(s) will have substantially dissipated (i.e., at least to a level that will not irreparably harm bone marrow) within three hours, or preferably two hours, of application of the occluding pressure to the body part of the patient. It is not presently possible to extend the period of occlusion for substantially longer than about three hours even when secondary measures such as chilling of the occluded body part or infusion of oxygenated blood into the occluded body part are taken, as explained more fully hereafter. Generally, the chemotherapeutic agent(s) is selected and administration of the chemotherapeutic agent (s) is timed so the level of toxicity of the chemotherapeutic agent to myelopoietic bone marrow has dissipated to a safe or acceptable level within no more than about two hours of occlusion of arterial blood flow to the body part. Alternatively, in some cases, a known neutralizing agent that lowers the toxicity of the chemotherapeutic agent(s) can be administered so that circulation can be restored to the occluded body part within a safe time period. The invention therapeutic treatment method can be repeated at spaced intervals of from eight hours to two months for up to 20 repeats, depending upon the choice of the chemotherapeutic agent.

Many chemotherapeutic agents have a known in vivo initial half life of about 25 minutes or less, as shown in Table I herein below. When such an agent is used in the practice of the invention method(s), the pressure can be removed to restore blood circulation to the protected bone marrow about 15 minutes after passage of the known period of initial half life of the chemotherapeutic agent.

1) the chemotherapeutic agent(s) and their active metabolic products have sufficiently short half-lives following intravenous administration so that the concentration of the active drug or active metabolic products are at a clinically safe level when the occluding pressure is released; 2) the agent(s) have hematological toxicity; and 3) the agent(s) have cytotoxic activity against the type of tumor being treated.

It is also possible to combine a myelosuppresive drug, such as those in Table 1, with a less myelosuppresive drug

TABLE 1

Myelosuppresive Chemotherapeutic Agents with Short Half-Lives

| Concer Drugs | Initial T½ | Terminal T½ | Toxicities | Common Indications | Dose |
|---|---|---|---|---|---|
| Mechlorethamine | ~1 min. | | hematologic, N/V | Hosgkin's dis. lymphoma, lung, breast, ovary cancers | 0.1 to 1.6 mh/kh IV |
| Doxorubicin | 5 min | 10 hrs | hematologic, cardiac | breast, ovary, lymphoma, lung cancers | 5 to 75 mg/m² IV |
| 5-FU + leucovorin | 16 min* | | hematologic, diarrhea, stomatitis | Colon, breast, rectal, stomach, ovary, cervix, bladder, liver, pancreatic, head and neck cancers | 300 to 1200 mg/m² IV 5-FU + 500 mg/m² IV LV |
| 5-fluoro-uracil (5-FU) | 16 min* | | hematologic, stomatitis | Colon, breast, rectal, stomach, ovary, cervix, bladder, liver, pancreatic, head and neck cancers | 300 to 1200 mg/m² IV |
| Dactino-mycin | 2 min | 36 hrs | hematologic; mucositis | Wilm's tumor, rhabdomyosarcoma, Swing's sarcoma, trophoblastic neoplasms, testicular, Kaposi's sarcoma, melanoma, breast, ovary cancers, and regional isolation perfusion | 0.2–2.5 mg/m² IV |
| Mitomycin-C | 6–17 min | | hematologic, 2% renal, HUS, pulmonary. | Breast, stomach, pancreas, colon, rectum, H & N, lung, carvix. | 5–10 mg/m² IV |
| Streptozocin | 5 min | 35–40 min | 25–70% renal, mild hematologic. | Pancreatic islet cell, carcinoid, Hodgkin's disease, colorectal, hepatoma, melanoma. | 200–500 mg/m² IV |
| Mito-xanthrone | 9 min | 29 hrs | moderate hematologic, cholestasis, cardiac | Leukemia, prostate | 4–75 mg/m² IV |
| BCNU | 6 min | 68 min | hematologic, pulmonary | Brain tumors, multiple myeloma, lymphoma, Hodgkin's disease, melanoma gastero-intestinal tumors, brewast, lung | 50–225 mg/m² IV |
| Cytarabine | 7–20 min | | hematologic | Leukemia, lymphoma. | 20–3000 mg/m² IV |
| Melphalan | 10 min | 75 min | hematologic | Multiple myeloma, ovarian, breast, prostate, melanoma, isolation perfusion. | 2–8 mg/m² IV |
| Thiotepa | 8 min | 2.4 hr | hematologic | Breast, ovary, lymphoma, lung, | 0.1–0.4 mg/kg IV |
| DTIC (da-carbazine) | 10 min | 5 hrs | hematologic | Melanoma, lymphoma, soft-tissue sarcomas, neuroblastomas. | 200 mg/m² IV |
| 5-fluoro-deoxyuridine | 16 min* | | hematologic, stomatitis | Colon, breast, rectal, stomach, ovary, cervix, bladder, liver, pancreatic, head and neck cancers | 5–20 mg/m² IV |
| 5-Aza-citidine | 2–5 min | | hematologic; neurotoxicity, mucositis | Leukemia | 200 mg/m² IV |

*Shoter half-life with smaller doses

The list of useful chemotherapeutic agents in Table 1 is merely exemplary and is not intended to be limiting in any way. Additional useful intravenous agents not included in Table 1, agents being developed, or agents yet to be developed, and combinations thereof, are just as useful provided they exhibit the following desirable characteristics:

in practice of the invention. Table 2 below lists chemotherapeutic agents that are less myelosuppresive than those in Table 1, but which can be combined with myelosuppresive drugs, such as those in Table 1, for combination chemotherapy. Of course, drugs in Table 1 may also be combined among themselves for combination chemotherapy.

TABLE 2

Less-Myelosuppresive Chemotherapeutic Agents for Combination Chemotherapy.

| Cancer Drugs | Initial T½ | Toxicities | Indications | Dose |
| --- | --- | --- | --- | --- |
| Cisplatin | 30 min | moderate hematologic, severe nausea/vomiting, renal | Testicular, lung, ovary, bladder, head and neck, cervical cancers. | 20–100 mg/m$^2$ IV |
| Vincristine | 2.6 hr | mild hematologic; neuropathy | Leukemia, Hodgkin's disease, lymphoma, sarcomas, small cell lung, breast, Kaposi's sarcoma, multiple myeloma, renal cell | 1–1.4 mg/m$^2$ IV |
| Hema-methyl-melamine** | 5 hrs | mild hematologic, neurotoxicity | Ovarian cancer | 150 mg/m$^2$ PO qd X 14 days |
| Bleomycin | 2 hr | mild hematologic; skin; pulmonary fibrosis, fever | Testicular, lymphomas, Hodgkin's disease, head and neck cancers | 2–15 U/m$^2$ IV qwk |

**Available in per oral formulation

Thus, it can be seen that the period of time after administration of the chemotherapeutic agent that the pressure is maintained on the occluded body part is determined by two factors—by the in vivo clearance rate of the chemotherapeutic agent, or the combination of the agents, and by the maximum safe period for stoppage of arterial flow into the body part under the treatment conditions (i.e., whether the occluded body part is being chilled and/or infused with pre-oxygenated autologous blood during the occlusion period). Generally, the occluding pressure is removed about 1 minute to about 2 hours after passage of a known period of initial half life so that the arterial flow is occluded for a period of from about 5 minutes to about 2 hours. For example, where the known period of initial half life is about 10 seconds to about 25 minutes, the removing of an invention tourniquet to release the pressure on the occluded body part is about 15 minutes after passage of the known period of initial half life. Whatever the pharmacokinetics or the treatment conditions, under existing technology the period of occlusion is limited to about 3 hours. However, it is anticipated that the maximum safe period of occlusion may be extended by future development in the art.

It is usually preferred, to minimize the period of occlusion of a body part, not only for safety, but for the comfort of the patient to alleviate such symptoms as anxiety, nausea, pain, and the like, caused by the combined physiological and psychological effects of the drugs and the occlusion of arterial flow. Therefore, the selection of the chemotherapeutic agent is guided, as much as possible (so long as the other two above-listed required characteristics are met) by giving preference to a chemotherapeutic agent having the shortest initial half-life. Nitrogen mustard (mechlorethamine) and 5-azacitidine have the shortest in vivo half-lives following intravenous administration in humans of all chemotherapeutic agents presently known. Because of the short half-lives of these drugs, it is safe to release the pressure on the occluded body part as soon as 10 minutes after administration of the drug(s) while substantially shielding the bone marrow within the occluded body part, although a somewhat longer period of post-administration occlusion, for example, 15 to 30 minutes or even up to 2 hours may increase the bone marrow protection to a further extent. When the chemotherapeutic agent is mechlorethamine, the effective amount is in the range from about 0.1 mg/kg to about 1.6 mg/kg, for example, in the range from about 0.2 mg/kg to about 0.6 mg/kg of body weight of the patient.

In addition to the short half-life, nitrogen mustard also has the advantage of having a broad spectrum activity against a variety of cancers, such as Hodgkin's disease, lymphoma, sarcoma and skin, lung, breast, brain, colon, prostate, testicular and ovarian cancers, and the like. Nitrogen mustard also has the property of being neutralized by sodium thiosulfate. Therefore, it is possible to neutralize the remaining activity of the drug remaining before removing the pressure (e.g. releasing the tourniquet) to allow arterial blood flow into the occluded body part. Due to this combination of properties, nitrogen mustard is currently the chemotherapeutic agent preferred for use in the invention method of treatment of these cancers.

The chemotherapeutic agent 5-azacitidine, which is a nucleoside analogue that has somewhat narrow spectrum of activity compared to nitrogen mustard, has an initial active half life of 2 to 5 minutes, making it an especially useful for use in the invention method wherein general anesthesia is not used. With the shielding of bone marrow according to the invention, as illustrated in Example 13 below, an escalation of dose intensity is now possible, for example to as high as 200 mg/m$^2$ of treated body surface. At such elevated dosage, this chemotherapeutic agent may have activity against a wider spectrum of cancers.

Doxorubicin is a DNA intercalator with very rapid initial half-life (about 5 minutes) followed by longer terminal half-life (about 10 hours or more). Because of the rapid initial half-life, substantial shielding of occluded bone marrow occurs when the occluding pressure is maintained for a period as short as about 15 minutes to 1 hour post administration of the doxorubicin, although a longer period of tourniquet application can further shield the bone marrow and further reduce myelosuppression therein. This agent has very broad spectrum of activity against cancers arising from breast, lung, ovary, and lymphoma. There are several different types of suitable dosing for use of doxorubicin in practice of the invention methods. For example, smaller doses such as about 5 mg/m$^2$ to about 20 mg/m$^2$ of treated body surface can be given frequently, for example daily for about 2 to about 5 times. Another method less frequently, is to give a larger dose, such as about 21 mg/m$^2$ to about 75 mg/m$^2$ of treated body surface, for example about 5 mg/m$^2$ to about 75 mg/m$^2$; 10 mg/m$^2$ to about 50 mg/m$^2$; or preferably, about 50 mg of doxorubicin per m$^2$ of treated body surface.

5-Fluorouracil (5-FU), alone or in combination with the vitamin leucovorin, and/or 5-fluorodeoxyuridine (both are pyrimidine nucleoside analogues) has a broad spectrum of activity against the commonly occurring malignancies, such as breast, head and neck, colon, and other cancers arising from the gastrointestinal tract. These primitive nucleoside analogues have relatively short half-lives of some 16 minutes, which is dose-dependent. That is, smaller doses have shorter half-lives, even as short as 8 minutes. Therefore, smaller, frequent doses allow use of shorter tourniquet times. Maximal tourniquet post-dosage duration, such as 1 to 2 hours, is most preferred to maximize bone marrow shielding, but a shorter duration of occlusion, such as about 30 minutes to about 59 minutes will still give substantial protection from the myelosuppresive effects of these drugs. However, these drugs can cause well known side effects, such as stomatitis, which can be reduced by ice chips in the mouth for a 30-minute period during bolus injection therapy. When 5-FU is given with leucovorin, diarrhea from enterocolitis can assume life-threatening proportions. This severe diarrhea usually responds to therapy, for example with octreotide acetate; however the fluid loss caused by diarrhea generally must be replaced by aggressive fluid replacement.

Dactinomycin (or actinomycin D) is a DNA intercalator whose antitumor and toxic effect may be proportional to peak drug concentration rather than to the prolonged exposure to low concentration. This agent also has very rapid initial distribution half-life of 2 minutes and very slow terminal half-life. Toward the end of the initial distribution phase, when the pharmacokinetic is beginning to be dominated by the slow terminal half-life, the plasma concentration usually drops below the concentration that is irreversibly damaging to human cells. Therefore, a post-dosage tourniquet duration of about 15 minute to about 1 hour, is sufficient time for the major part of initial rapid half-life distribution phase to run its course and to allow the drug concentration in plasma to drop close to or below a therapeutic concentration. Nevertheless, a longer tourniquet duration of about 1 to about 2 hours may be further beneficial for shielding the occluded bone marrow from myelosuppression. Several different suitable dosing regimens can be used in practice of the invention method using dactinomycin. For example, about 0.2 to about 0.5 mg/m$^2$ of affected body area can be administered at spaced intervals, for example daily for about 2 to 5 times. Alternatively, a larger dose, such as about 0.6 to about 2.5 mg/m$^2$, can be administered less frequently. Use of dactinomycin in the invention method is illustrated herein in Example 17 below.

Mitomycin-C is an agent with a fairly broad spectrum of activity against breast, stomach, pancreas, colon, rectum, head and neck, lung, and cervical cancers and has a half-life of 6–17 minutes. Since hematologic toxicity is severe with this drug, a tourniquet duration of 1 to 2 hours is preferred. Nevertheless, a shorter duration of tourniquet application, such as 30 minutes to 59 minutes, may provide additional shielding from myelosuppresive effects to the bone marrow within the circulation-isolated part of the body. Non-hematological toxicity, especially hemolytic uremic syndrome and pulmonary toxicities, are rare, but potentially dose limiting and fatal. The usual intravenous dose is from about 10 to about 20 mg/m$^2$ of treated body surface.

Streptozocin has chemotherapeutic activity against such cancers as Hodgkin's disease and pancreatic islet cell or carcinoid colorectal cancers, hepatoma, and melanoma and the like. Because this drug is cleared by the liver, Streptozocin may cause problems when the drug is combined with other drugs metabolized by the liver, such as doxorubicin. Also, because of potential renal toxicity, this drug is generally not combined with other nephrotoxic drugs, such as cisplatin. The hematologic toxicity of streptozocin is relatively mild as compared with other chemotherapeutic drugs. Therefore, the recommended post-dosage duration of occlusion is from about 30 minutes to about 60 minutes. Example 19 below is an example of the invention method employing Streptozocin.

Mitoxantrone is a DNA intercalator with rapid initial half-life of 9 minutes and a long terminal half-life of 29 hours. As is the case with actinomycin D, plasma concentration of mitoxantrone drops below the lethal concentration for human cells at the end of the initial rapid-half-life (i.e., the distributive phase of pharmacokinetics) so that the period of occlusion necessary to substantially shield bone marrow from myelosuppressive effects is about 30 minute to about 1 hour post-dosage. Nevertheless, a longer post-dosage tourniquet duration of about 1 to about 2 hours may be further beneficial for reducing myelosuppression in the shielded bone marrow. There are several different types of suitable dosing. Smaller doses such as about 4 mg/m$^2$ to about 20 mg/m$^2$ of treated body surface can be given frequently, for example daily for 2 to 5 times. Alternatively, a larger dose, such as about 21 mg/m$^2$ to about 75 mg/m$^2$ of treated body surface can be administered less frequently. Example 20 below illustrates use of mitoxantrone in the invention method.

BCNU (carmustin) has a somewhat broad spectrum of activity against brain tumor, multiple myeloma, lymphoma, melanoma, gastero-intestinal tumors and breast and lung cancers. The main toxicities are hematologic and pulmonary. The pulmonary toxicity can be ameliorated by concurrent administration of prednisone. Because the plasma half-life of BCNO is 15–20 minutes, bone marrow is generally shielded by maintaining the occluding pressure for about 1 to about 2 hours following administration of the BCNU. However, a shorter duration of 30 minutes to 1 hour also provides some protection to the bone marrow within the circulation-isolated part of the body. Example 21 below illustrates use of BCNU in practice of the invention method.

Cytarabine is mainly useful for treatment of leukemia and lymphoma. However, it has synergistic activity against solid tumors when given with other agents, such as cisplatin. In addition, when administered in frequent small doses, this agent has significant activity against a broad spectrum of solid tumors in its own right. Cytarabine has fairly short half-life in circulation, about 7–20 minutes. Thus, in practice of the invention method, the shielding is preferably continued for about 1 to about 2 hours after administration of cytarabine to maximize bone marrow protection, but a shorter duration of shielding, such as about 30 minutes to about 1 hour will reduce the myelosuppresive effect, especially when the cytarabine is given in smaller doses within this range. This drug has hematologic toxicity as the main side-effect. Use of cytarabine in the invention method is illustrated in Example 22 below.

Melphalan has a biphasic pharmacokinetic profile following intravenous administration in humans. The initial half-life is quite short, about 10 minutes, but the terminal half-life is quite long at about 75 minutes. Therefore, in practice of the invention method, the occluding pressure is preferably maintained for about 1 to about 2 hours following administration of melphalan. However, shielding for a shorter duration, such as about 30 minutes to about 1 hour post-dosage, is beneficial in protecting the shielded bone marrow against the myelosuppresive effects of melphalan. Use of melphalan in the invention method is illustrated in Example 23 below.

Thiotepa is a polyfunctional alkylating agent with a wide spectrum of anti-cancer therapeutic activity, for example against breast, ovarian, and lung cancers, as well as against lymphomas. Following intravenous administration, the serum concentration of thiotepa declines rapidly with a half-life of about 8 minutes during the initial distributive phase of pharmacokinetics (i.e., the initial half-life). Therefore, when thiotepa is used as the therapeutic agent in practice of the invention method, maintaining the occluding pressure for about 15 to about 60 minutes after administration of the drug is generally sufficient to provide substantial protection against myelosuppression to the shielded bone marrow. Nevertheless, longer tourniquet duration such as about 1 to about 2 hours post-dosage may further decrease the exposure of the shielded bone marrow to myelosuppressive effects of the drug. Use of thiotepa in the invention method is illustrated in Example 24 below.

Dacarbazine (DITC) is a synthetic analogue of the naturally occurring purine precursor, 5-amino-1H-imidazole-4-carboxamine, but this drug works as an alkylating agent and has a spectrum of activity against melanoma, lymphoma, soft-tissue sarcomas, and neuroblastomas. The initial distributive phase half-life is quite short at about 10 minutes. Therefore, applying pressure to occlude arterial blood flow to the shielded body part for about 30 to about 60 minutes post-dosage provides substantial protection against myelosuppression therein. Applying the occluding pressure for a longer period, such as about 1 to about 2 hours, may further reduce myelosuppression in the shielded bone marrow. An illustration of the invention method using dacarbazine as the chemotherapeutic agent in the invention method is provided in Example 25 below.

When the invention bone marrow shielding tourniquet is used to occlude arterial blood flow to both shoulder areas, the chemotherapeutic drug is most conveniently administered via a central venous catheter, such as a Port-A-Cath®, Hickman catheter, Groshong catheter, Pick line, or Broviac catheter. The catheter is preferably placed into a vein selected from the group consisting of internal jugular vein, external jugular vein, and the subclavian vein.

In patients undergoing the chemotherapy according to the invention method, the venous blood pH prior to tourniquet activation is generally between 7.33 to 7.37 with an average of approximately 7.35; $pO_2$ is 43–53 mmHg (48 mmHg average), $pCO_2$ is 38–43 mmHg (average of 41 mmHg), and lactic acid concentration is 3 to 9 mg/dl. When arterial flow is occluded, for example, by inflation of the invention tourniquet, the oxygen is initially consumed fairly rapidly by continued aerobic metabolic activity, generating carbon dioxide. As hypoxia deepens, the cells largely convert into an anaerobic metabolic pathway, which does not consume oxygen, but generates lactic acid, which in turn lowers the blood pH. Following the initial 30 minutes of tourniquet inflation, the venous blood pH drops to 7.24–7.30, $pO_2$ drops to 25–30 mmHg (average 27 mmHg), $pCO_2$ rises to 48–56 mmHg, and lactic acid rises to 20 to 30 mg/dl. After 60 minutes of total tourniquet time, the blood pH drops further to an average of 7.14 (range: 7.11–7.17), $pO_2$ drops slightly further to 22–25 mmHg (average 23 mmHg), $pCO_2$ rises further to 63–69 mmHg (average 65 mmHg), and lactic acid continues to rise precipitously to 50–70 mg/dl. At 90 minutes of total tourniquet time, the blood pH drops further to an average of 6.99 (range: 6.97–7.05), $pO_2$ drops further to 9–19 mmHg (average 13 mmHg), $pCO_2$ rises further to 83–91 mmHg (average 88 mmHg), and lactic acid continues to rise precipitously to 60–80 mg/dl. At 120 minutes of total tourniquet time, the blood pH is now very acidotic with average pH of 6.90 (range: 6.88–6.96), $pO_2$ drops very low to 3–9 mmHg (average 7 mmHg), $pCO_2$ rises even further to 95–113 mmHg (average 107 mmHg), and lactic acid is now 80–100 mg/dl.

The invention method may further comprise steps designed to counteract the build up of hypoxia in the tissue of the bone marrow-shielded body part. For example, the invention method may further comprise chilling the occluded body part during at least a portion of the time during which the occluding pressure is applied. Hypothermia of the occluded limb decreases the metabolic rate within the limb, which results in decreased consumption of oxygen and other nutrients while decreasing production of harmful metabolic products in the absence of arterial blood flow. Chilling a limb during temporary occlusion of circulation therein results in slower development of metabolic disequilibrium within the limb (i.e., slowing of the rate of decline of blood pH and $pO_2$, and slowing of the rise in $pCO_2$ and lactic acid concentration. Thus, damage to tissues during the transient regional ischemia is reduced.

Yet another embodiment of the invention method(s) comprises administering highly oxygenated autologous blood into the occluded body part while the occluding pressure (e.g., the tourniquet) is applied. The highly oxygenated autologous whole blood can be prepared and infused as is known in the art, and as described in Example 11 hereinbelow.

In another embodiment of the invention method(s) wherein arterial blood flow is to be occluded in a shoulder or hip, the affected extremity is exsanguinated prior to application of pressure to occlude arterial flow therein. Exsanguination can be accomplished by such well known methods as application of gravity drainage, or by use of a bandage designed to progressively press blood from an extremity towards the trunk of a patient, such as an Esmarch bandage.

In another embodiment, the invention method further comprises administering to the patient an effective amount of one or more cytokines, such as G-CSF, GM-CSF, Stem cell factor, Thrombopoietin, IL-12, EPO, and the like, and suitable combinations thereof, to stimulate various components of blood-forming elements, or other cytokines that result in expansion of myelopoiesis in myelopoietic bone marrow and into peripheral areas of bone marrow. The cytokines can be administered prior to and/or after the chemotherapy. For example, about 2 to about 10 days, or about 4 to about 7 days, and preferably about 5 days, prior to administration of the chemotherapeutic agent, one or more of such cytokines are given daily or twice weekly to expand the bone marrow. Then chemotherapy is administered as described herein. Administration of the cytokine(s) can be repeated following chemotherapy. This embodiment of the invention method is illustrated in Example 4 below. Alternatively, starting with the administration of chemotherapy or following the administration of chemotherapy, the patient can be administered the cytokine daily by subcutaneous injections for about 7 to about 30 days (for example, about 10 to about 20 days, and preferably about 14 days) to stimulate the bone marrow.

To combat discomfort and anxiety in the patient during the practice of the invention method, the method may further comprise premedicating the patient prior to application of the occluding pressure by administering to the patient an effective amount of one or more active agents for relieving pain, anxiety, nausea or vomiting, and the like, and suitable combinations of any two or more thereof. This additional step is particularly recommended when the invention method of bone marrow shielded chemotherapy is practiced without the use of general anesthesia. The use of such active agents in conjunction with particular chemotherapeutic agents is illustrated in the Examples below.

The chemotherapeutic agent and/or cytokine is administered in an "effective amount." An effective amount is the quantity of a chemotherapeutic agent necessary to prevent, to cure, or at least partially arrest growth of a tumor, or of a symptom of cancer associated therewith. An effective amount of a cytokine is the quantity of a cytokine necessary to stimulate growth of bone marrow in a subject. A patient or human is any mammal having a human-shaped shoulder or hip area, preferably a human. Amounts effective for therapeutic use will, of course, depend on the severity of the disease and the weight and general state of the subject as well as the mode or regimen of administration (i.e., whether multiple smaller doses are preferred over bolus injection of the maximum recommended dose, and the like). Since individual subjects may present a wide variation in severity of symptoms and each therapeutic agent has its unique therapeutic characteristics, it is up to the practitioner to determine a subject's response to treatment and vary the dosages accordingly. In addition to the considerations pertaining to the pharmacokinetics of the chemotherapeutic agents, various considerations in arriving at an effective amount are described, e.g., in *Goodman And Gilman's: The Pharmacological Bases of Therapeutics,* 8th ed., Pergamon Press, 1990; and *Remington's Pharmaceutical Sciences,* 17th ed., Mack Publishing Co., Easton, Pa., 1990, each of which is herein incorporated by reference in its entirety.

The chemotherapeutic agent can be administered either as a bolus injection, drip, or continuous infusion. Buffers, preservatives, antioxidants, and the like, can be incorporated as required.

In another aspect, the invention provides a bone marrow shielding tourniquet adapted to apply pressure around a shoulder or hip of a human. The invention tourniquet comprises an inflatable bladder contoured for substantially covering the shoulder or hip and having an inner face and an outer face, a fluid-tight connector on the bladder for connecting the bladder to a source of fluid pressure, and a substantially inelastic exterior layer substantially covering the outer face of the bladder so as to limit expansion of the bladder in the direction of the exterior layer when the bladder is inflated by fluid from the fluid source. The exterior layer can be semi-flexible or inflexible. When the exterior layer is inflexible, the exterior layer has a three-dimensional shape selected to hold the bladder around the shoulder or hip area. The invention tourniquet can optionally further comprise a co-operative fastener attached to the tourniquet for releasably affixing the tourniquet around the hip or shoulder, although the tourniquet can be lashed around the shoulder or hip using any suitable type of tie or belt that does not form a part of the tourniquet. No matter how the tourniquet is affixed around the body part to be occluded, it is important that the fastener not be subject to inadvertent release during the practice of the invention method to prevent potentially lethal damage to the patient's bone marrow.

In a presently preferred embodiment, the invention tourniquet further comprises a flexible interior layer lining the inner face of the bladder. The exterior layer and interior layer may co-operatively form an envelope for containing the bladder such that inflation of the bladder causes the bladder to extend the flexible interior layer. In this embodiment, the invention tourniquet can further comprise a fastener attached to or contiguous with the envelope so formed so that engagement of the fastener affixes the tourniquet with the interior layer in contact with the body parts such as a hip or shoulder. In any event, when the tourniquet is in position around the hip or shoulder and fluid pressure is introduced into the bladder through the fluid-tight connector attached thereto, the constraining force exerted by the semi-flexible or inflexible, substantially inelastic exterior layer causes the bladder to expand towards the shoulder or hip that the tourniquet surrounds.

Since the invention tourniquet is adapted to apply an occluding pressure around a shoulder or hip area of a human, the overall shape of the tourniquet must be selected to substantially cover, or wrap around, at least the shoulder or hip so as to cut off arterial flow into the upper ⅓ of the proximal humerus or femur. To facilitate this requirement, in a presently preferred embodiment, the invention tourniquet has two longer, arcuate sides, and two shorter, straight sides. One arcuate side describes a larger arc than the other so that the bladder has an overall shape described by the difference between the sectors of two circles having a common center and swept out by a common angle, but having radii of substantially different length. To adequately cover the shoulder or hip area of the human, the difference in the length of the radii describing the arcuate sides of the tourniquet is generally from about 2 inches to about 10 inches, although the exact difference will depend upon the general body size of the patient and whether the invention tourniquet is intended to be positioned around a shoulder or a hip.

This embodiment of the invention tourniquet is illustrated in FIGS. 3, 4 and 5, which show an invention contoured shoulder tourniquet 20 having larger and smaller arcuate sides 36 and 35, respectively, two shorter straight ends 66, and a two-part cooperative fastener (of hooks and loops), with one part 34 located on the interior layer 67 and one part 33 (shown in dotted outline in FIG. 3) located on the exterior layer 68 of the tourniquet. The interior and exterior layers form an envelope to contain inflatable bladder 37 having an inner face 69 and an outer face 70. Air pump 21, pressure gauge 22, air feed tube 23, are in fluid communication with inflatable bladder 37. FIG. 4 is a cross-sectional view taken through line 30—30 of FIG. 3; FIG. 5 is a cross-sectional view taken through line 31—31 of FIG. 3.

The connector on the inflatable bladder is in fluid communication with a source of fluid pressure. As shown in the Figures herein, the source of fluid pressure includes an air pump bulb 21, air pressure gauge 22, air pressure tubing 23, and pressure relief valve 29. However, as used in the description and claims herein the term "source of fluid pressure" is intended to include any type of fluid pump known in the art, including a self-inflating air bag, which may be contained within the tourniquet itself. The fluid pump can be adapted to supply fluid pressure to two or more of the bladders simultaneously and/or independently.

An optional protuberance 32 also contained within the envelope is contoured and located so that the protuberance fits into the arm pit of the patient when the invention shoulder tourniquet is positioned around the shoulder area. The protuberance 32, which equalizes pressure distribution over the shoulder area decreases likelihood of tissue damage caused by the tourniquet itself, can be either located on the surface of the bladder itself, or, when the tourniquet comprises an interior layer, the protuberance can be located either on the interior layer or under the interior layer on the inner face of the bladder (i.e., within the envelope that encloses the bladder). Although FIGS. 3, 4 and 5 show a preferred embodiment of the optional fastener, a fabric hook and loop fastener system 33 and 34, the fastener can also be a belt buckle system, strong snaps, ties, and the like, or any type of device known in the art for securely, but releasably fastening together two different objects or parts of a continuous object.

In another embodiment of the invention tourniquet, the arcuate sides are substantially equal in length and are arranged in mirror image to one another so that the tourniquet has an overall hour glass shape.

The inflatable bladder contained in the invention tourniquet is pressurizable to at least about 300 mmHg and is configured so that, when affixed around a shoulder or hip and inflated, the tourniquet occludes arterial flow to the upper ⅓ of the proximal humerus or femur (as well as to the extremities containing them) and thereby shields the myelopoietic the bone marrow therein. FIG. 1, which is a "see-through" figure, illustrates the invention shoulder tourniquet in position on cancer patient 1 with an arm 10 in a preferred elevated position. Shoulder tourniquet 20 is positioned in a preferred shoulder area location to enable occlusion of arterial flow through not only the major arterial trunk, axillary artery 4 and brachial artery 5, but also the smaller branch arteries such as anterior humeral circumflex artery 8 posterior humeral circumflex artery 9 and deltoid branch of thoraco-acromial artery 2 that supply blood to proximal humerus.

Figure 2:
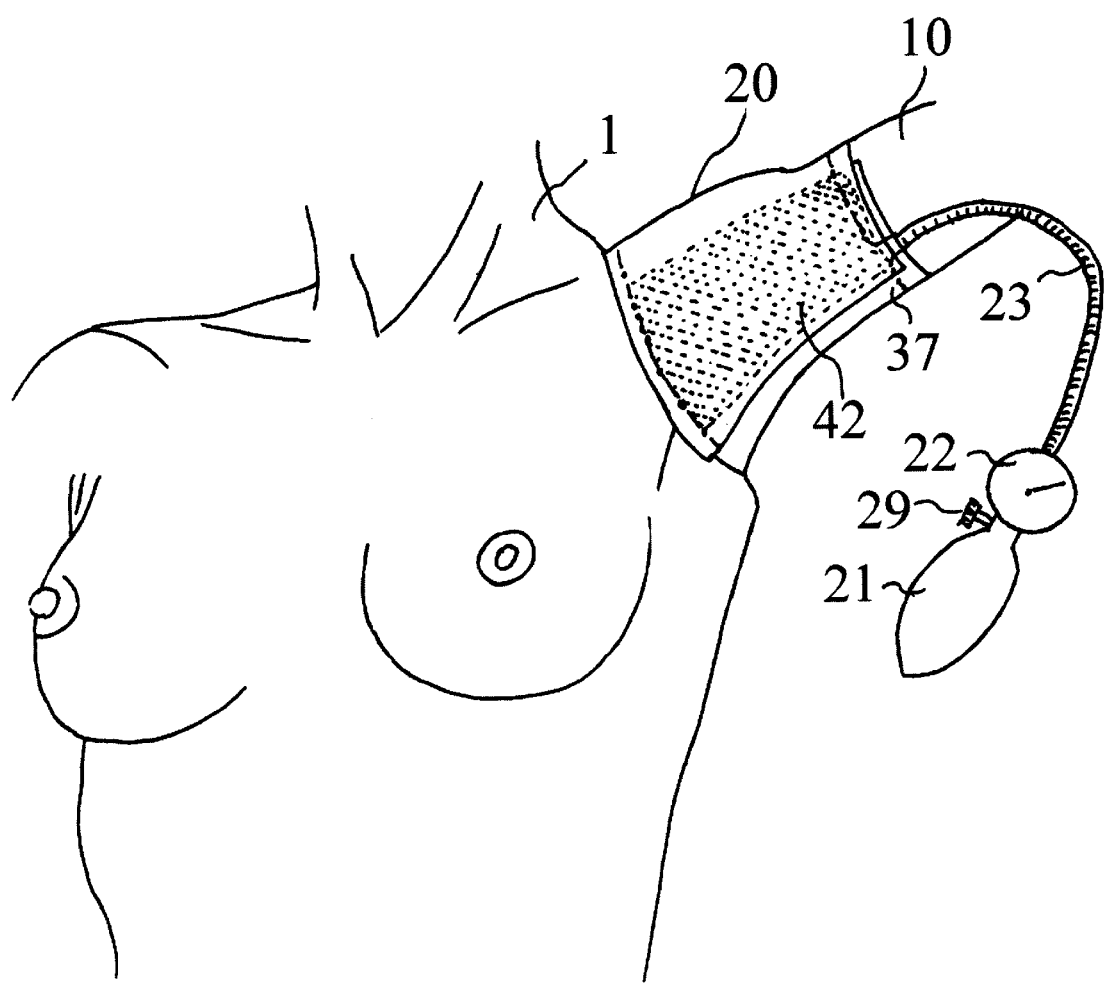
FIG. 2 is a perspective view of shoulder tourniquet apparatus of the present invention positioned and affixed on a patient's shoulder area.

FIG. 2 is an alternate view of shoulder tourniquet 20 of the present invention position at a preferred location of a cancer patient's 1 shoulder area, with an arm 10 in a preferred elevated position, to enable occlusion of arterial flow through not only the major arterial trunk, axillary artery and brachial artery, but also the smaller branch arteries such as anterior humeral circumflex artery 8, posterior humeral circumflex artery 9, and deltoid branch of thoraco-acromial artery 2 that supply blood to proximal humerus as shown in FIG. 1.

Figure 10:
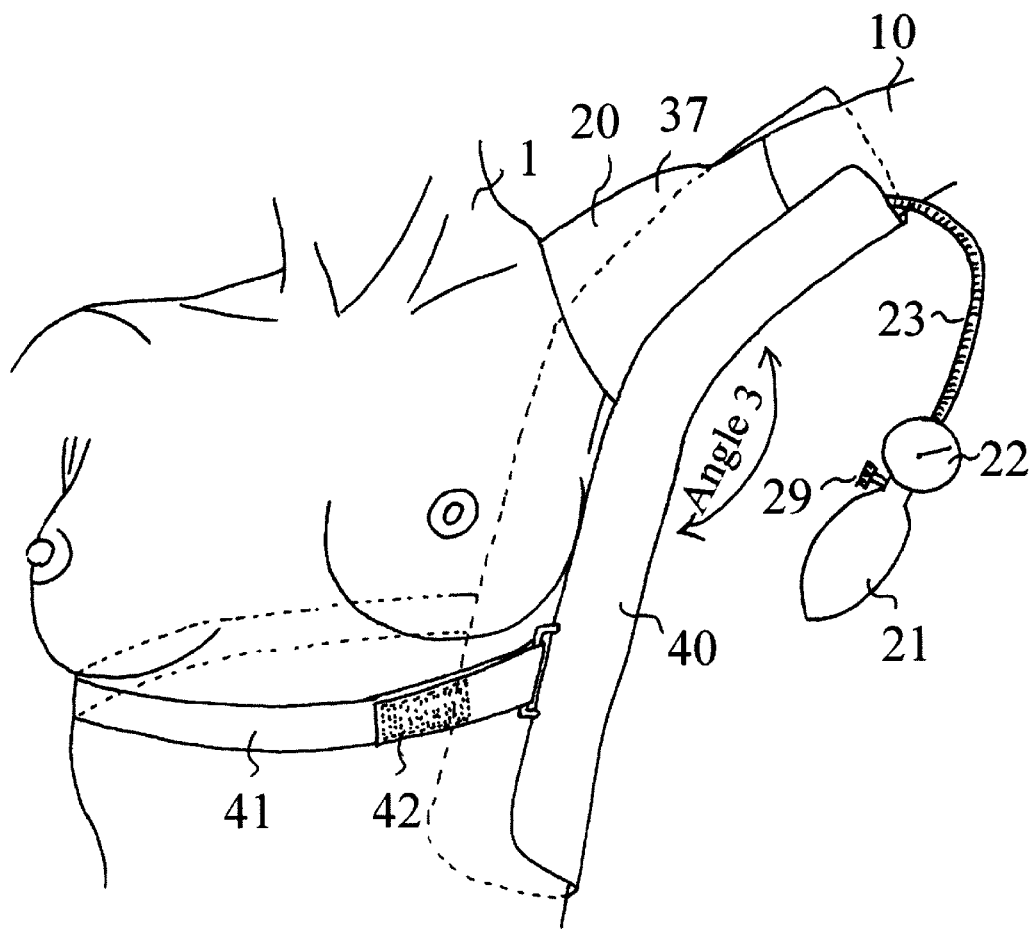
FIG. 10 is a perspective view of an invention shoulder tourniquet in place on a patient's shoulder area, wherein the tourniquet includes a brace to keep the occluded arm elevated at an angle away from the patient's torso.
Figure 11:
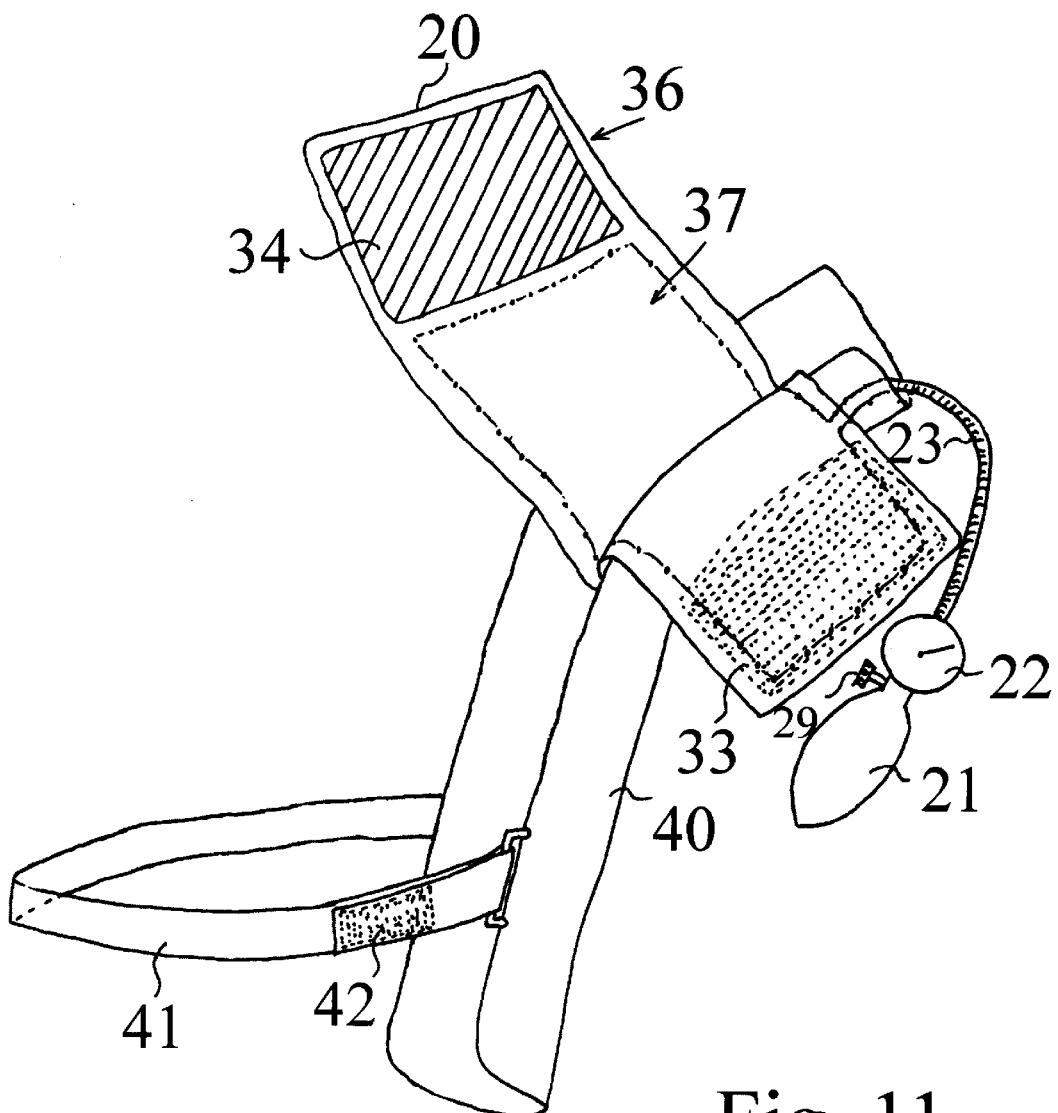
FIG. 11 is a perspective view of an invention shoulder tourniquet fitted with a brace and positioning belt.

In another embodiment shown in FIGS. 10–11, the invention shoulder tourniquet further comprises a brace, preferably rigid, attached to the tourniquet (e.g., to the exterior of the tourniquet). The brace is shaped to hold an arm attached to the shoulder at a fixed angle from the side of the torso to which the shoulder attaches when the tourniquet is affixed around the shoulder. Optionally, the invention shoulder tourniquet can still further comprise a brace fastener, such as a strap, attached to the portion of the brace that extends along the torso and adapted to fasten around the torso of a human. FIG. 10 shows a shoulder tourniquet 20 having a rigid elevating brace 40, which keeps the arm elevated at an angle 3 away from the patient's torso. The angle 3 formed by the patient's arm and proximal side of the torso is generally between 45 degrees and 180 degrees, for example between 75 degrees and 160 degrees, and preferably between 85 degrees and 140 degrees. As shown in FIG. 10, The elevating brace 40 is held firmly in place by physical attachment to the tourniquet 20 and by brace strap 41, which is adapted to encircle and fasten around the patient's torso as shown. The brace strap 41 includes a fabric hook and loop fastener system 42 for securing the brace strap around the torso of the patient. FIG. 11 is a perspective view of the invention shoulder tourniquet that includes a rigid or stiff elevating brace 40 and brace strap 41.

Figure 12:
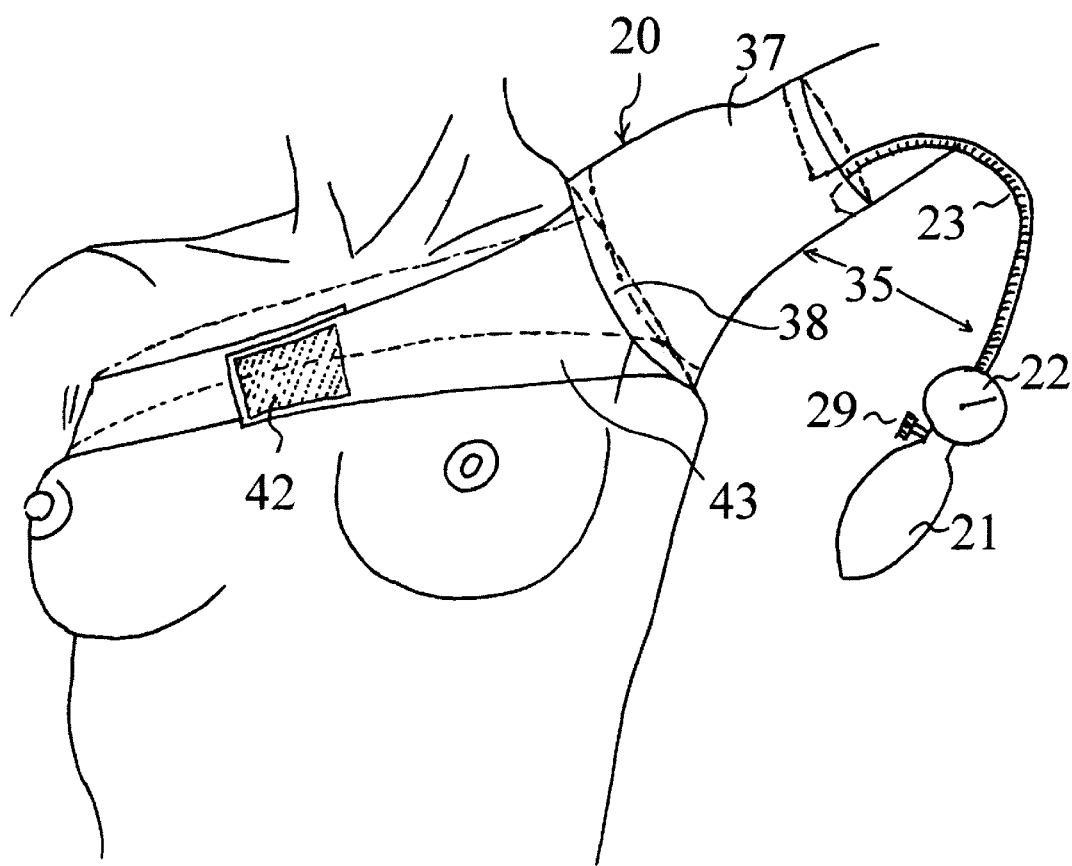
FIG. 12 is a perspective view of an invention shoulder tourniquet affixed on a patient's shoulder area, wherein the tourniquet includes a positioning belt to aid in affixing the tourniquet at a preferred position around the shoulder and to prevent migration of the tourniquet away from the preferred position around the shoulder.
Figure 13:
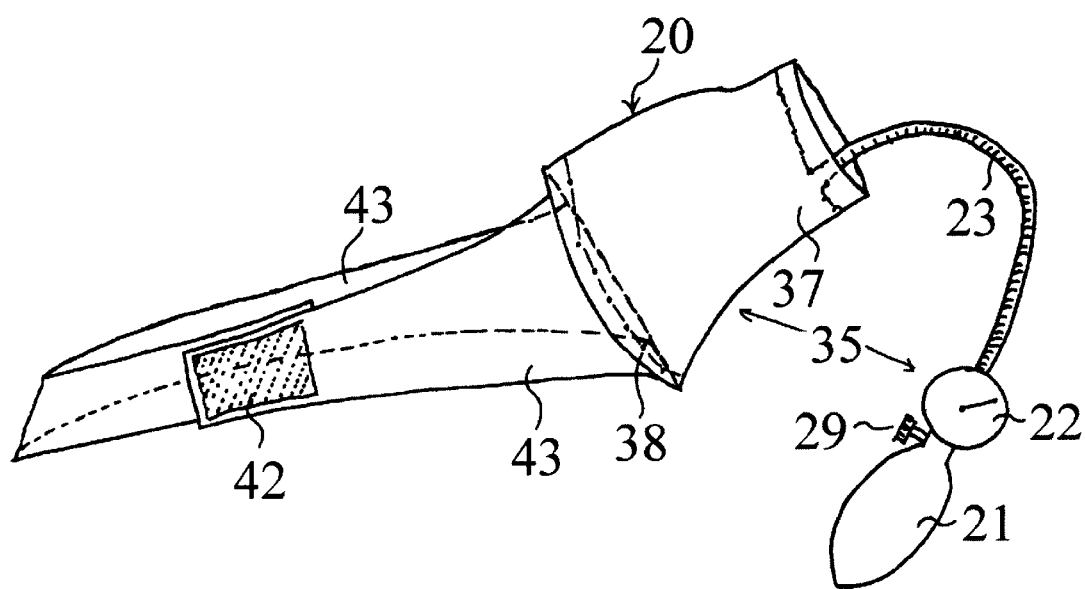
FIG. 13 is a perspective view of an invention shoulder tourniquet fitted with a positioning belt to aid in affixing the tourniquet at a preferred position on the shoulder.

The invention tourniquet optionally further comprises a positioning fastener, which positioning fastener is attached to the tourniquet for fastening around the torso to prevent migration of the tourniquet from the affixed position around the shoulder or hip. FIGS. 12 and 13 show a shoulder tourniquet, in which the positioning fastener is a positioning fastener 43, shown here as a belt, positioned to keep the shoulder tourniquet at a preferred position around the shoulder area of the patient and to prevent migration of the tourniquet away from the preferred location around the shoulder. As shown in FIGS. 12 and 13, belt 43 is sewn onto the fabric cover 38 of the shoulder tourniquet 20, and is tightly fastened with a two-part fabric hook and loop fastener system 34 and 33. The belt loops around the chest to keep shoulder tourniquet in a preferred position even without the elevating brace shown in FIG. 11.

Figure 17:
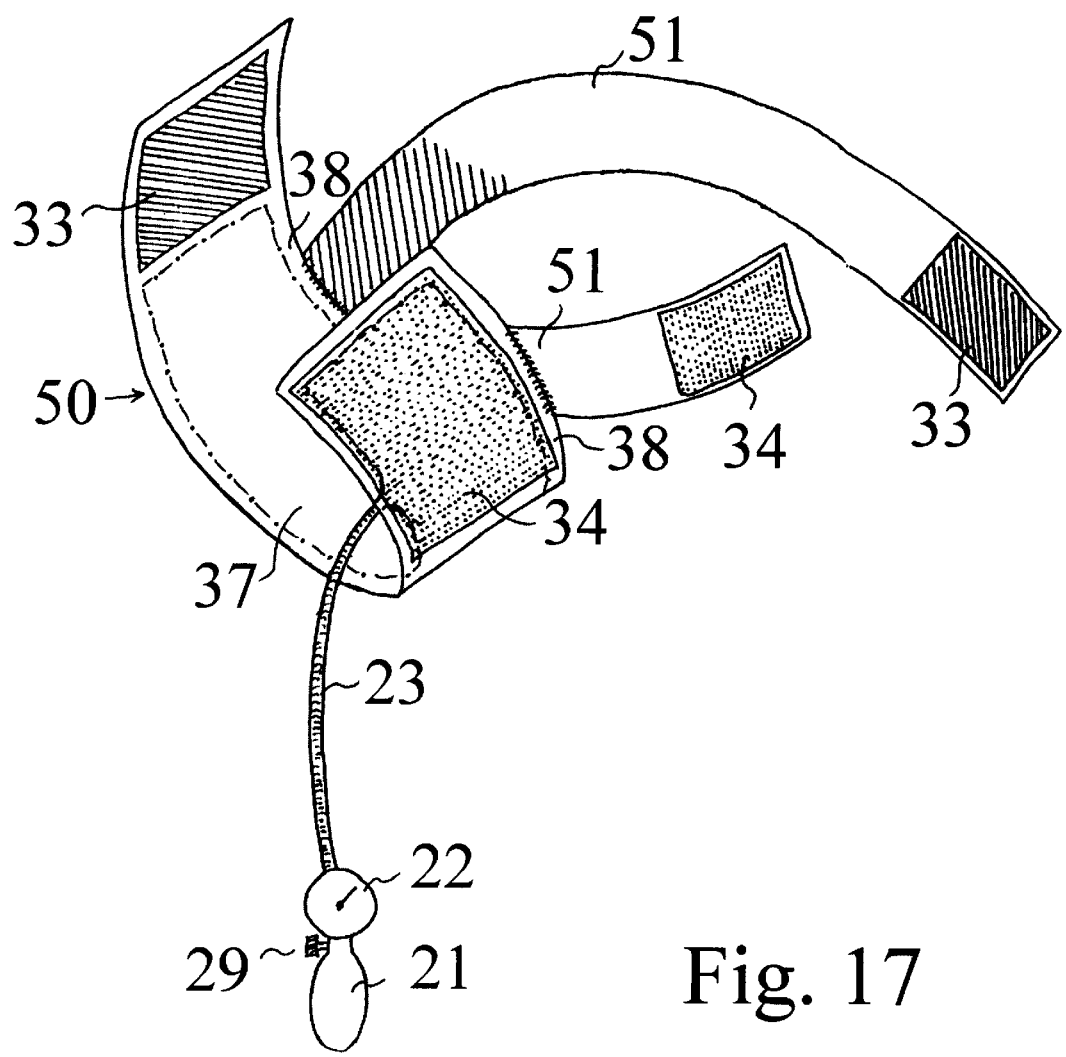
FIG. 17 is a perspective view of an invention hip tourniquet that is fitted with a. positioning belt to keep the tourniquet at a preferred position around the hip and to prevent migration of the tourniquet away from the preferred position around the hip.

FIGS. 15–17 illustrate an embodiment of the invention tourniquet 50 adapted for affixation around the hip area of a patient. FIG. 15 shows an invention hip tourniquet 50 applied to cancer patient 1 with a thigh 26 in a preferred extended position to facilitate position of hip tourniquet 50 around the hip area so as to enable occlusion of arterial flow through not only the major arterial trunk, external iliac artery 7, and femoral artery 6, but also the smaller branch arteries such as lateral femoral circumflex artery 16 and medial femoral circumflex artery 17 that supply blood to proximal femur. The angle 25 formed by the patient's thigh 26 and the patient's torso 11 is generally between 45 degrees and 155 degrees, for example, between 75 degrees and 155 degrees, and preferably between 90 degrees and 145 degrees.

Figure 18:
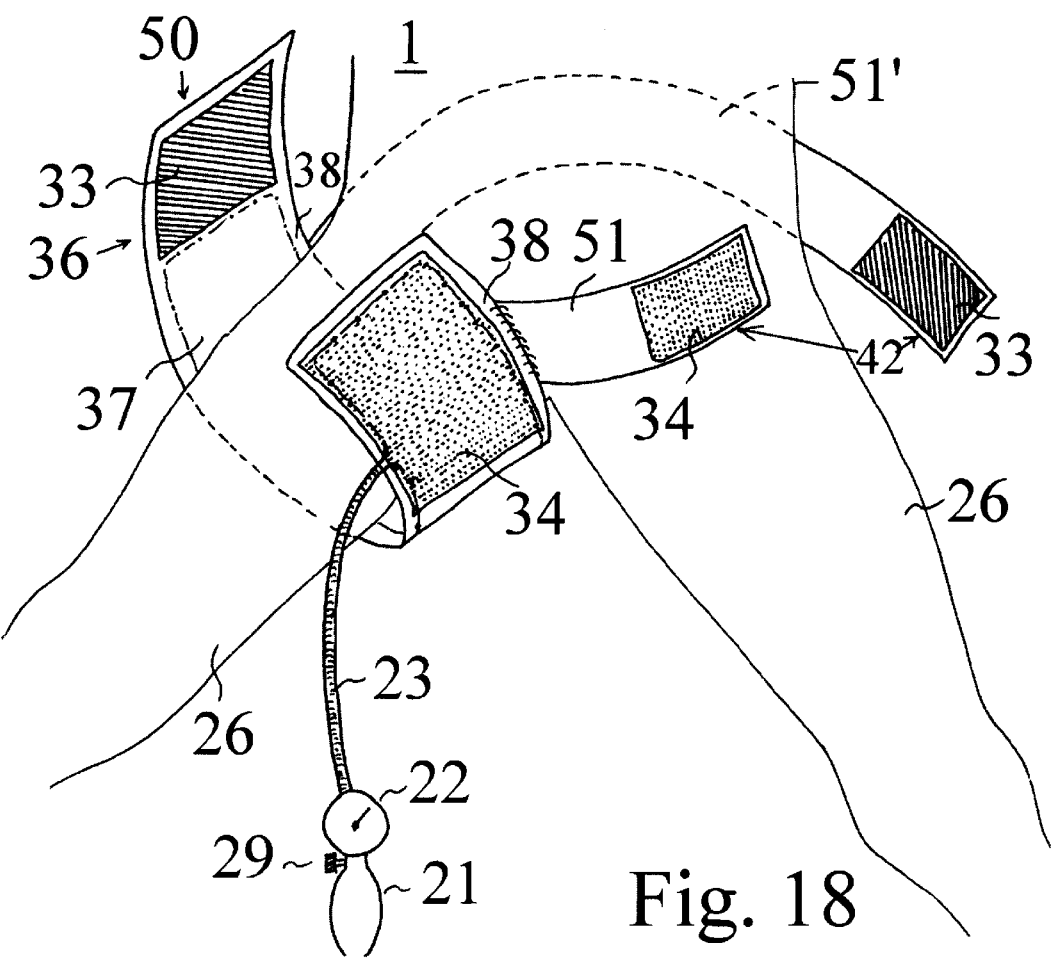
FIG. 18 is another perspective view of FIG. 17, showing the invention hip tourniquet about to be placed around the hip area of a patient.
Figure 19:
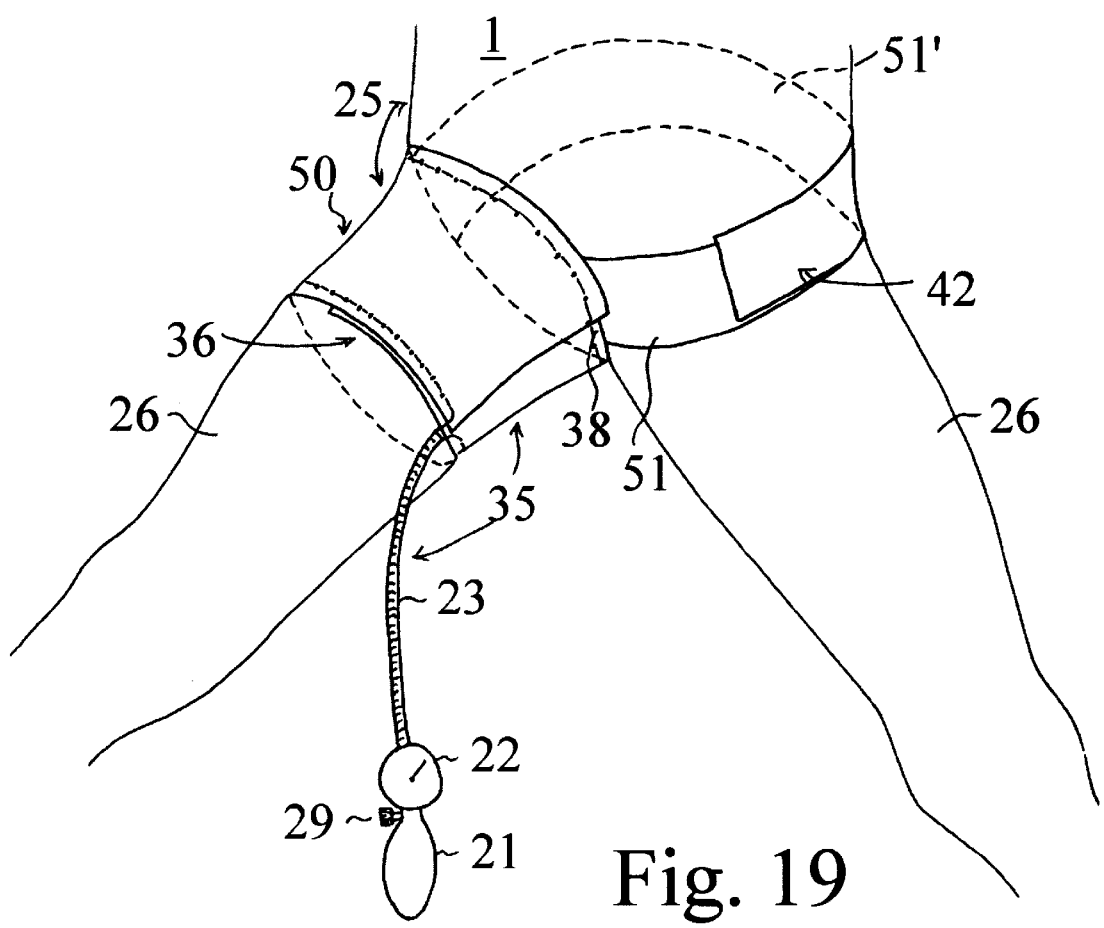
FIG. 19 is another perspective view of FIG. 17, showing the invention hip tourniquet in place around a hip of a patient.
Figure 20:
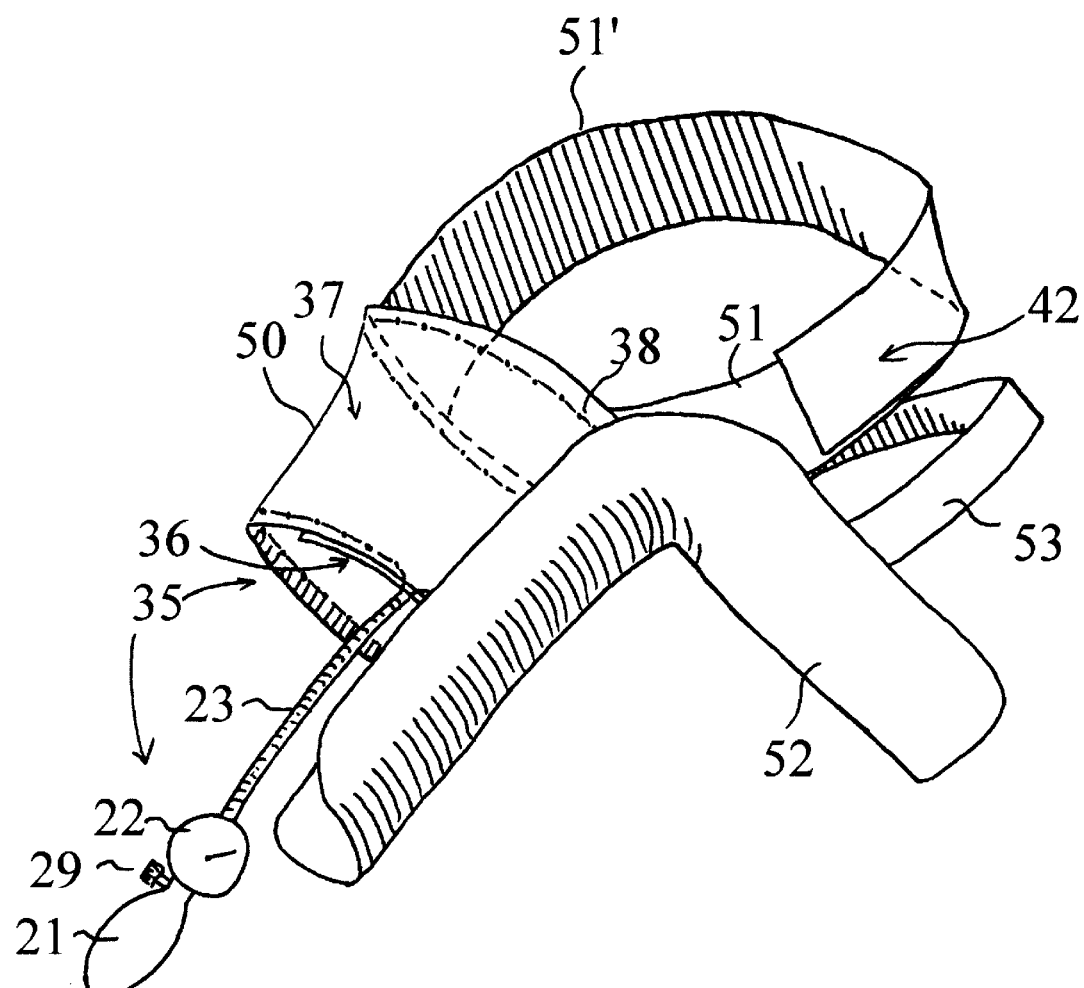
FIG. 20 is a perspective view of an invention hip tourniquet that is fitted with a brace to keep the to keep the occluded leg extended at a fixed angle toward the patient's torso.

As shown in FIGS. 17–19, the hip tourniquet can include a hip positioning fastener 51 (shown here as belt 51 sewn to the exterior of tourniquet 50 and having a two-part fabric hook and loop fastener system 33 and 34) for fastening around the pelvis of the patient to prevent migration of the tourniquet from the affixed position around the hip. The hip tourniquet may also optionally include a brace 52 attached to the tourniquet (shown in FIGS. 20 and 21) for holding the patient's thigh at a fixed angle to the proximal side of the patient's torso.

In an alternative embodiment, the exterior layer of the tourniquet is semi-flexible or inflexible and has a three-dimensional shape selected to hold the bladder around the body part to be occluded, such as the hip area, or shoulder and/or scapular area. The hard shell exterior can be fabricated in several different sizes to accommodate a broad range of body builds. The exterior layer of this "hard shell" tourniquet is generally fabricated from a material selected from the group consisting of an artificial polymer, leather, plaster of Paris, metal, natural woven fiber, and the like, and combinations thereof. The preferred material is an artificial polymer (e.g., a plastic) such as polyethylene, poly propylene, polycarbonate, ethacrylate, acrylic, and the like.

Figure 6:
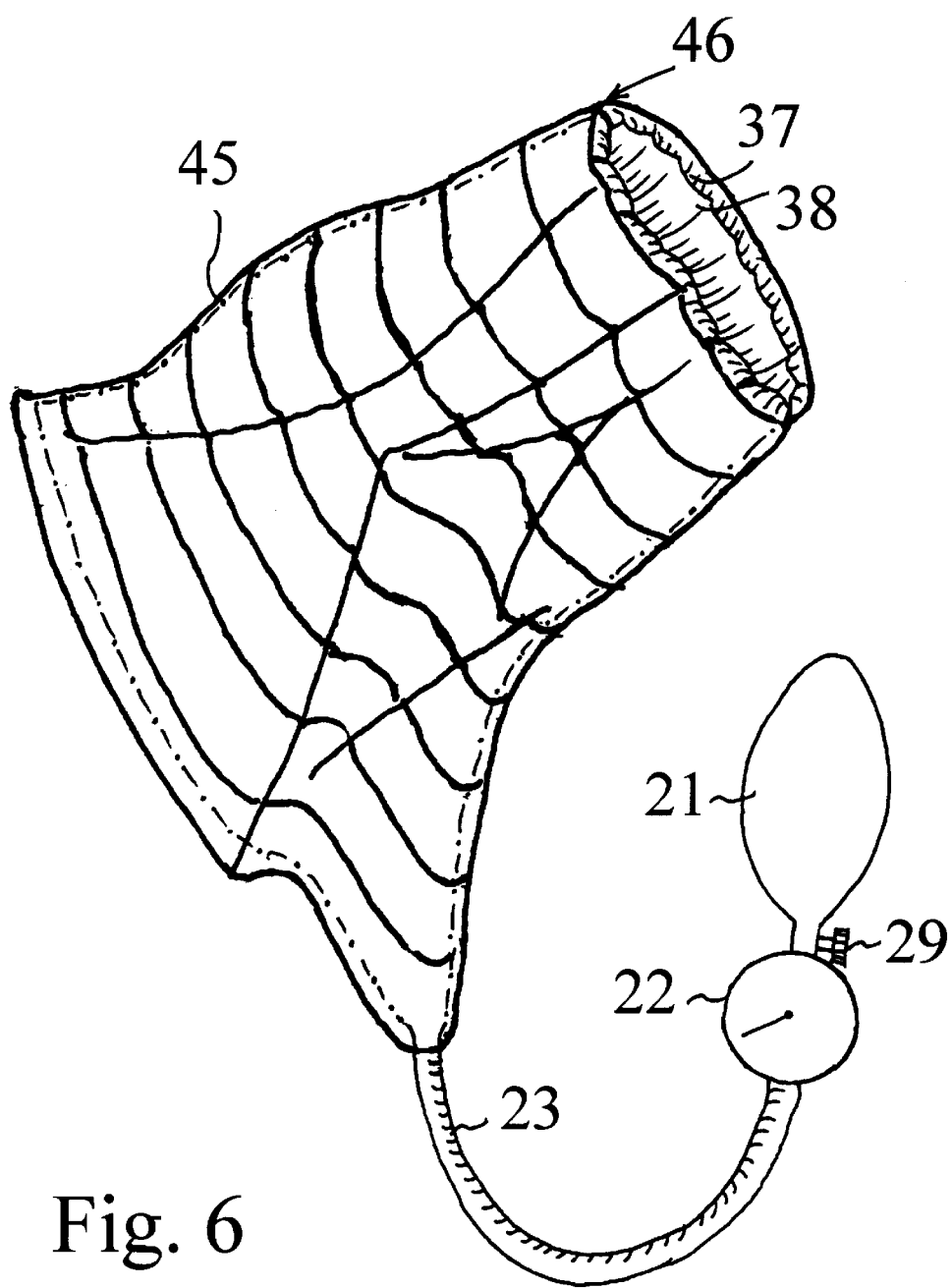
FIG. 6 is a perspective view of an invention hard-shell tourniquet.
Figure 7:
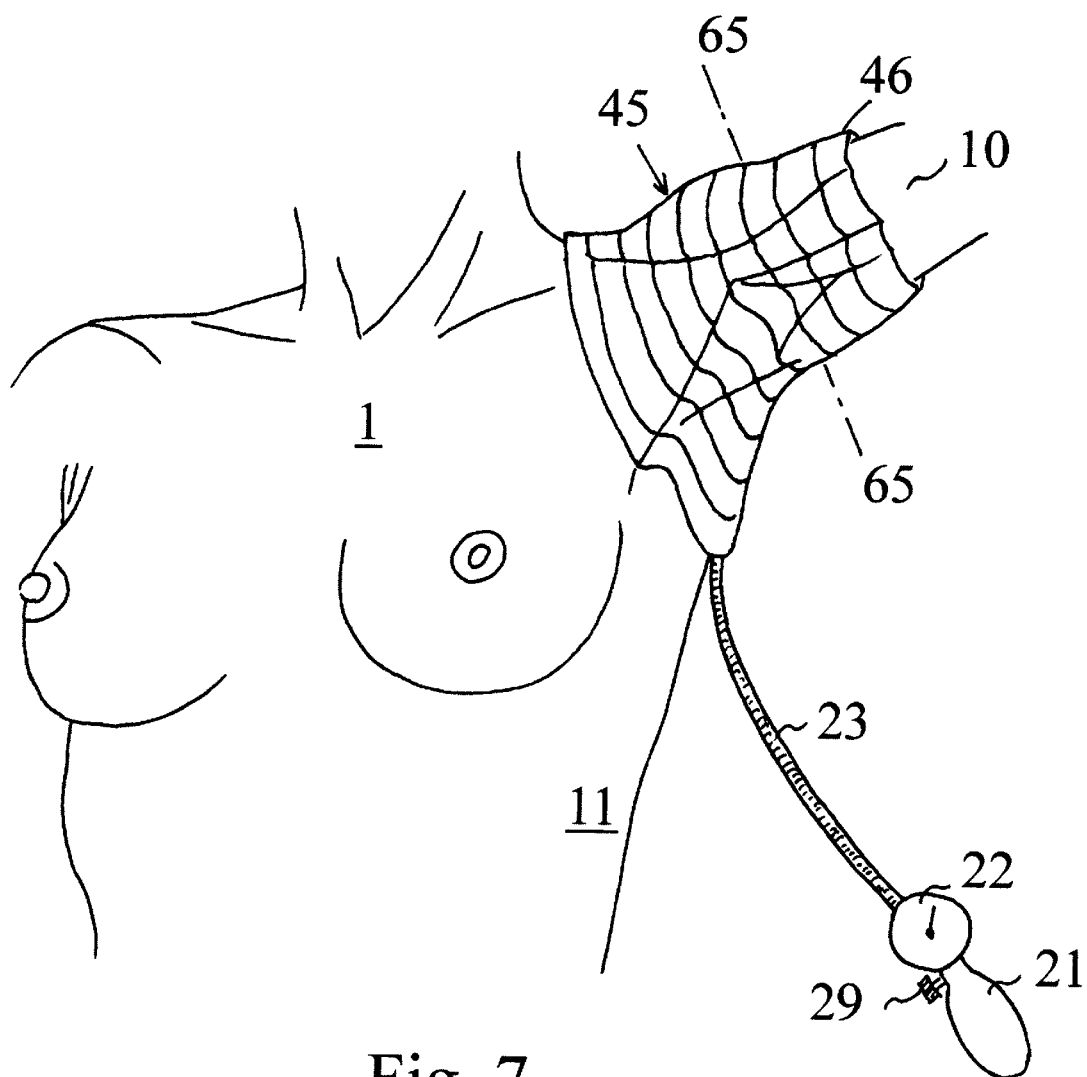
FIG. 7 is a drawing showing an invention hard-shell tourniquet applied onto a cancer patient.

FIG. 6 illustrates an invention hard-shell tourniquet 45 for the shoulder area. The inflexible exterior layer 46 loosely conforms to the contour of the body part to which it is to be applied, in this case, the shoulder. In FIG. 6, the hard shell is shown striped to demonstrate the surface contour. Attached to, and lining the inside surface of the hard shell, is the inflatable bladder 37 with fabric interior layer 38 that comes in contact with the skin of the patient. The inflatable bladder 37 is connected to a source of fluid pressure via an attached fluid-tight connector, shown here as the air pressure tubing 23, air pressure gauge 22, and air pump bulb 21. FIG. 7 shows a hard-shell tourniquet applied onto the shoulder of a cancer patient 1. To apply the hard shell tourniquet, the patient's arm 10 is slipped through the hard-shell tourniquet and positioned as shown. When the inflatable bladder is pressurized with air pump 21, the bladder 37 balloons only in the central direction, toward the patient's arm. This results in relatively uniform distribution of pressure over the entire shoulder area so that blood vessels are occluded without excessive pressure, resulting in decreased pain and decreased risk of tissue damage during the period of tourniquet inflation.

FIG. 8 is a cross section through the shoulder tourniquet of FIG. 7 at line 65, and shows a cross section through the upper humerus bone 12 having myelopoietic bone marrow 47 contained within. This cross sectional view shows the inflexible exterior layer 46 that loosely conforms to the contour of the body part to be applied, in this case, the shoulder, and the inflatable bladder 37 in the beginning stage of inflation with smaller amount of air within the bladder cavity 39. In FIG. 9, the inflatable bladder 37 of FIG. 8 is inflated further. As the inflatable bladder 37 is inflated above the blood pressure, the blood vessels would be completely collapsed and occluded, until the pressure is relieved. This cross sectional view also shows bone marrow within humerus 47, deltoid muscle 48, biceps muscle 49, triceps muscle 54, pectoralis major muscle 55, musculocutaneous nerve 56, median nerve 57, brachial artery 58, brachial vein 59, ulnar nerve 60, radial nerve 61, teres major muscle 62, subcutaneous fat 63, and coracobrachialis muscle 64.

Still another embodiment of the present invention is a hard-shell tourniquet for the hip area that is analogous to that shown in FIGS. 6 through 9, except the contour of the hard-shell follows that of the hip area. Again, the inelastic and inflexible hard shell directs pressure of the inflatable bladder towards the center, resulting in relatively uniform distribution of pressure over the hip area. As a result, less pressure is required to occlude the blood vessels, which in turn results in decreased pain and decreased risk of tissue damage during the period of tourniquet inflation.

In another embodiment, the invention provides a bilateral hard shell bone marrow shielding tourniquet adapted for wearing by a human. The invention bilateral hard shell tourniquet comprises a semi-flexible or inflexible and inelastic exterior carapace in one or more pieces, wherein the carapace has a three-dimensional shape adapted to substantially cover at least the bilateral scapular areas and/or shoulder areas of a wearer while allowing the head, arms, and lower torso to protrude from the carapace. Bilateral inflatable bladders can be attached along the interior surface of the carapace that, when inflated, apply pressure over at least the bilateral scapular areas and/or shoulder areas of the wearer, and a fluid-tight connector on each inflatable bladder for inflating the bladder, wherein inflation of one or both bladders exerts sufficient pressure upon the respective covered areas of the wearer to occlude arterial flow into at least the covered areas. Alternatively, the bilateral bladders can be separate from the tourniquet and applied to the wearer before the carapace is placed around the wearer. Generally the bilateral hard shell tourniquet further comprises at least one fastener attached to the carapace for cinching the carapace about the chest of the wearer. This embodiment of the invention is illustrated in FIGS. 22–29.

Figure 22:
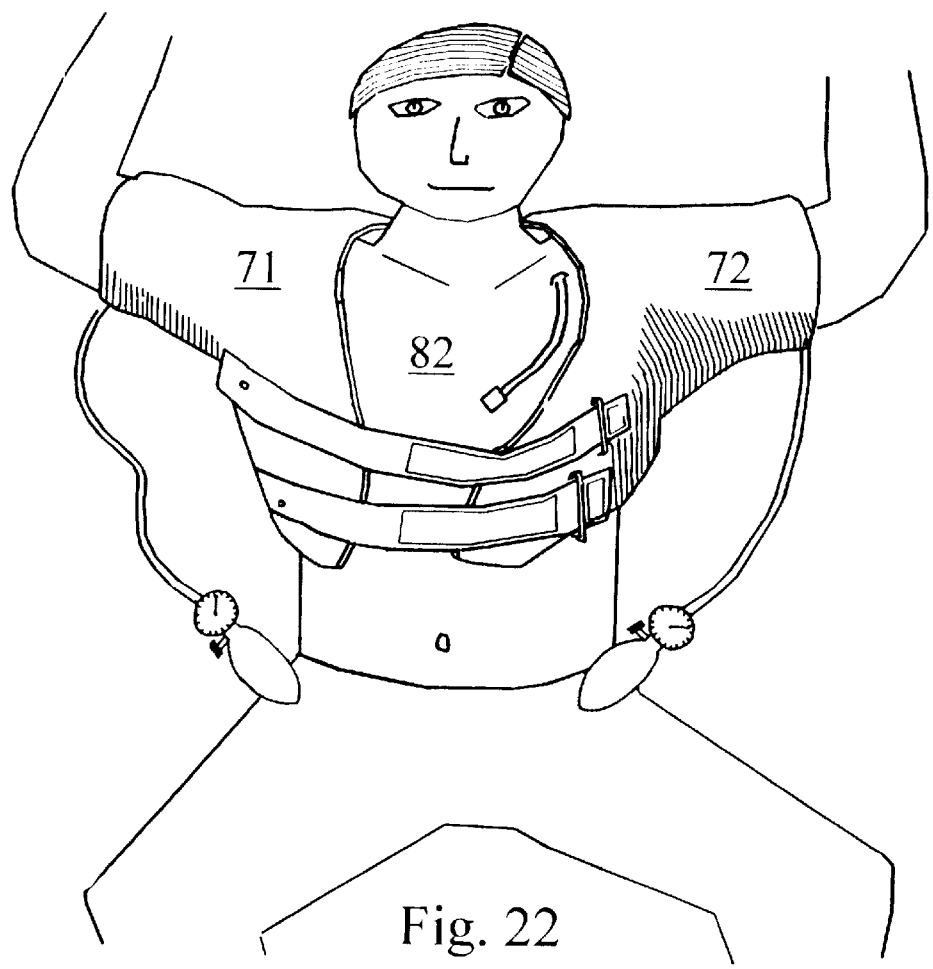
FIG. 22 is a perspective view of an invention hard shell bilateral tourniquet placed around a wearer's upper torso and substantially covering both humeri, and both scapulae.

FIG. 22 shows cancer patient 1 wearing an invention bilateral hard-shell tourniquet 70 having a two part inflexible carapace and attached bilateral flexible bladders designed to apply pressure to bilateral humeri and bilateral scapulae of a patient when the tourniquet is assembled around and "worn" by the patient placing an arm 76 through each arm hole 73 and moving the two pieces of the carapace about the shoulders and scapulae to co-operatively substantially cover the bilateral scapulae and shoulders of the wearer, and cinching the carapace 70 about the chest of the wearer using fasteners 77. The wearer's head 80, arms 76 and torso 81 protrude from the tourniquet and neck/chest opening 82 defined the two pieces of the carapace is large enough to facilitate blood circulation in the part of the wearer's body that is not occluded by the tourniquet. As further shown in FIGS. 23–25, carapace parts 71 and 72 each have an armhole 73 for receiving an arm of the wearer and anterior 74 and posterior 75 sides. At least one adjustable fastener 77 (shown here as two belts, each with an end attached to the anterior side of one of the two carapace pieces, and each with a fabric hook and loop fastener system) joins the anterior sides 74 of the two carapace pieces across the chest of the wearer. At least one additional adjustable fastener 78 (shown in FIGS. 23 and 24 as two belts (in cross-hatching)) joins the two posterior sides 75 of the two carapace parts across the back of the wearer.

Figure 23A:
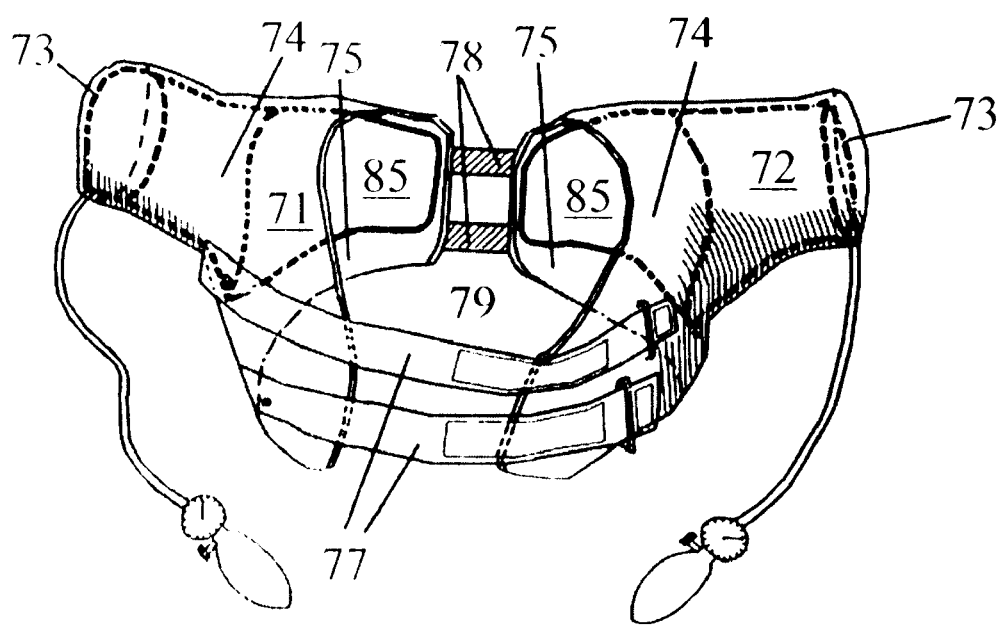
FIG. 23A is a frontal elevation view of an invention hard shell bilateral tourniquet having a two piece carapace with the two pieces assembled, but with the fasteners on the anterior and posterior exterior of the tourniquet not cinched. The carapace is designed to cover bilateral shoulder and bilateral scapular areas of the wearer. A torso opening is shown at the bottom of the tourniquet. The dotted lines show hidden portions of the bilateral bladders and of the torso opening at the bottom of the tourniquet.
Figure 23B:
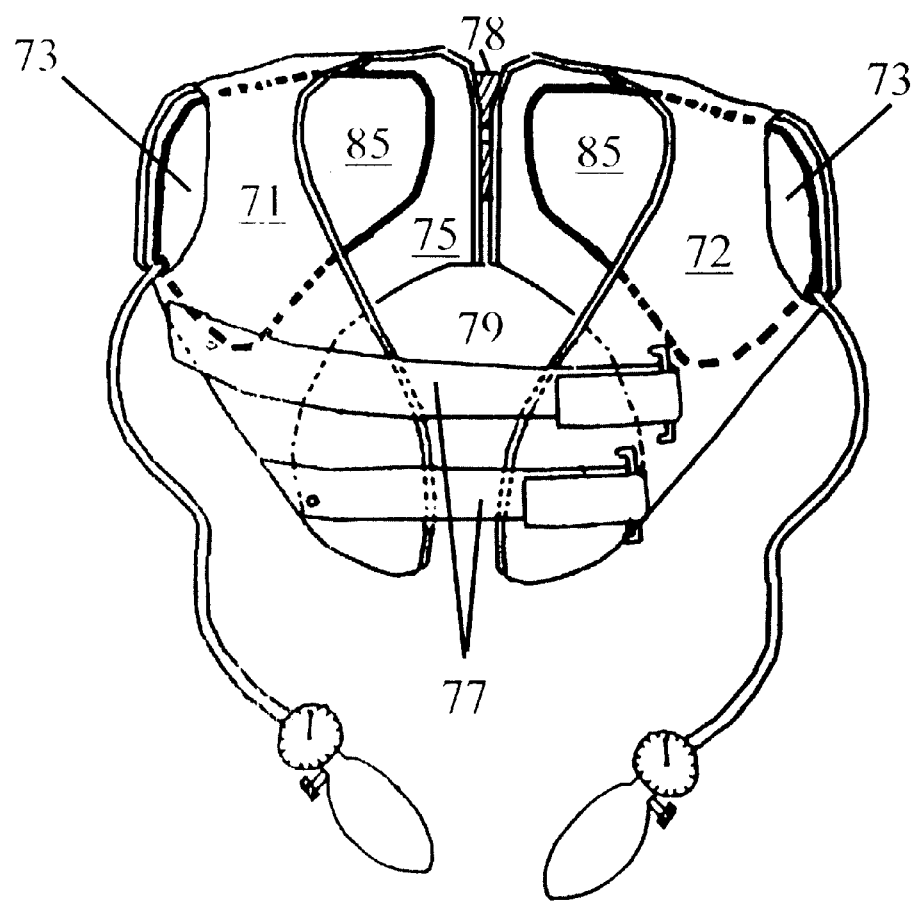
FIG. 23B is a frontal elevation view of the invention hard shell bilateral tourniquet having a two piece carapace as illustrated in FIG. 23A, except that the carapace is designed to cover the bilateral scapular areas of the wearer, but not the bilateral shoulder areas.
Figure 24:
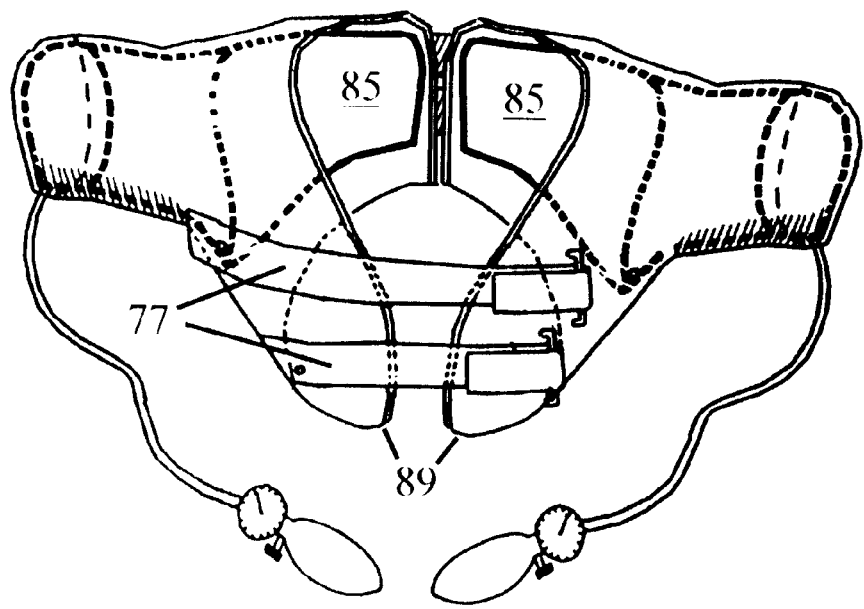
FIG. 24 is a frontal elevation view of the tourniquet of FIG. 23 with the two pieces assembled and cinched together by the fastener.

As can further be seen in FIGS. 23 and 24, the posterior sides 75 of the carapace pieces are shaped to co-operatively create a bottom torso opening 79. Similarly, the two anterior sides 76 of the carapace pieces co-operatively form a neck/chest opening 82. Cushions can be placed under the anterior sides 74 of the carapace to facilitate breathing and blood circulation in the non-occluded parts of the wearer while the tourniquet is worn and the bladders are inflated. A chemotherapeutic agent(s) is administered intravenously through central line catheter 91.

Two mirror image inflatable bladders 85 have a shape and are attached to and positioned along the interior surface of the corresponding carapace pieces to substantially cover the respective shoulder area and proximal scapula of the wearer when the tourniquet is cinched around the chest of the wearer. Each bladder has a fluid-tight connector for attaching the inflatable bladder to a source of fluid pressure for inflating the bladder, shown in FIGS. 22–25 as including an air pump bulb 21, air pressure gauge 22, air pressure tubing 23, and pressure relief valve 29. The preferred shape of the bilateral inflatable bladders 85 (shown in detail in FIG. 25) is designed to exert sufficient pressure upon the respective shoulder area and proximal scapula of the wearer to occlude arterial flow in the covered area and proximal extremity. Preferably, the tourniquet is cinched about the chest of the wearer before the bladders are inflated. As shown by a comparison of FIGS. 23A and 24, fasteners 77 and 78 are adjustable to cinch the two pieces about the wearer by drawing the two pieces of the carapace about the upper torso of the wearer.

As illustrated in FIG. 23B, the carapace optionally covers the bilateral scapular areas of the wearer without covering the bilateral shoulder areas. FIG. 23B shows two carapace pieces 71 and 72 abbreviated in the extension over the shoulder caps as compared with the carapace of FIG. 23A. In this embodiment of the invention, the mirror image inflatable bladders 85 are similarly contoured to cover the surface of a human scapula (the triangular shoulder blade bone) to occlude arterial flow therein, but not to cover the shoulder area sufficiently to occlude arterial flow in the shoulder area.

Figure 26:
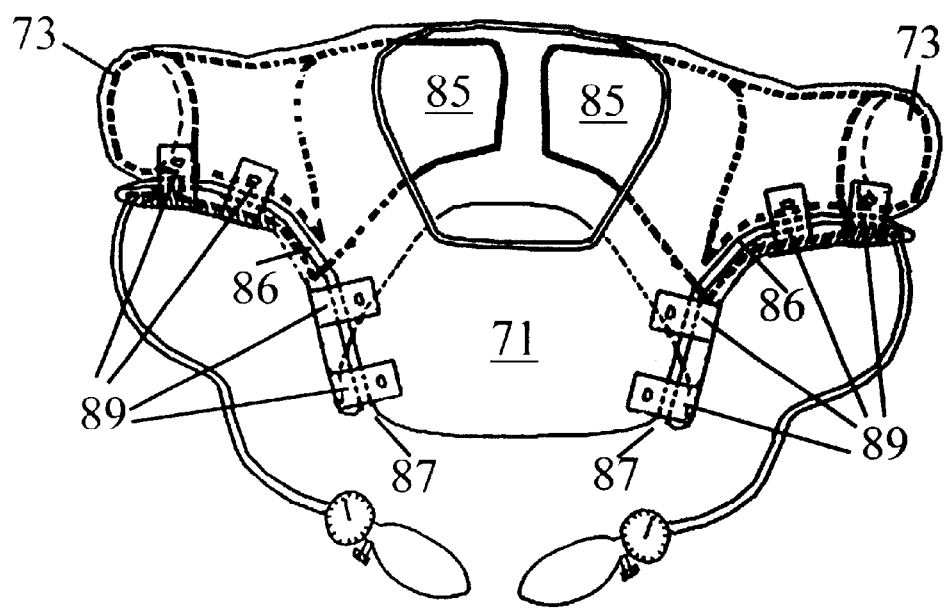
FIG. 26 is a frontal elevation view of an invention hard shell bilateral tourniquet having a one piece semi-flexible carapace with under arm openings drawn together and cinched by a plurality of fasteners. The bottom of the tourniquet has a torso opening. Bilateral inflatable bladders for applying pressure to the wearer's bilateral shoulder areas and scapulae are shown lining the interior surface of the invention tourniquet carapace above the bottom torso opening. Hidden portions of the torso opening and bladders are shown in dotted lines.
Figure 27:
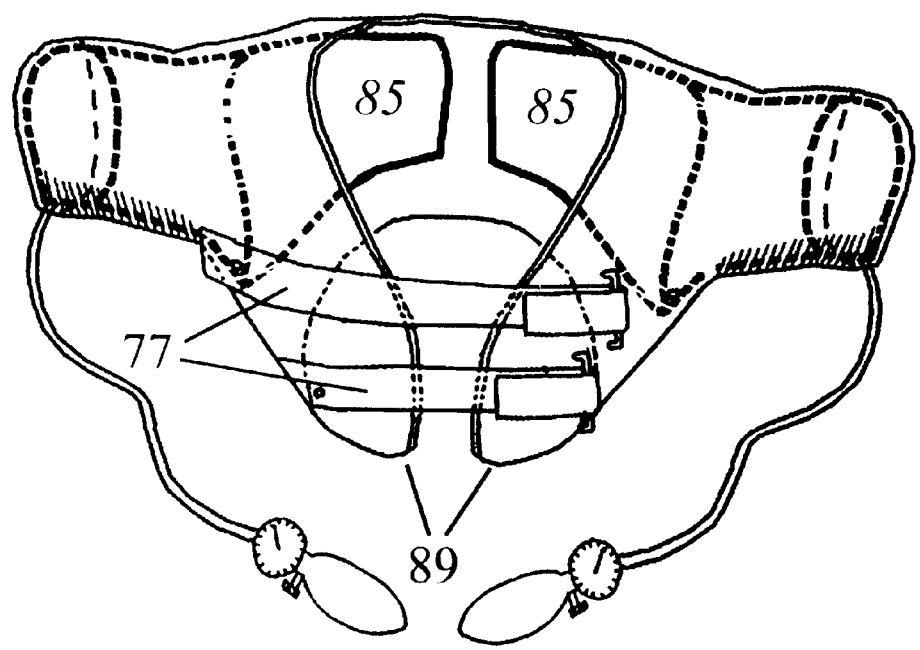
FIG. 27 is a frontal elevation view of an invention hard shell bilateral tourniquet having a one piece, front-opening, semi-flexible carapace that the wearer puts on like a vest. Two fasteners join the left and right sides of the back of the carapace across the chest of the wearer. Bilateral inflatable bladders for applying pressure to the wearer's bilateral shoulder areas and scapulae are shown lining the interior surface of the invention tourniquet carapace with hidden portions shown as dotted lines.
Figure 28:
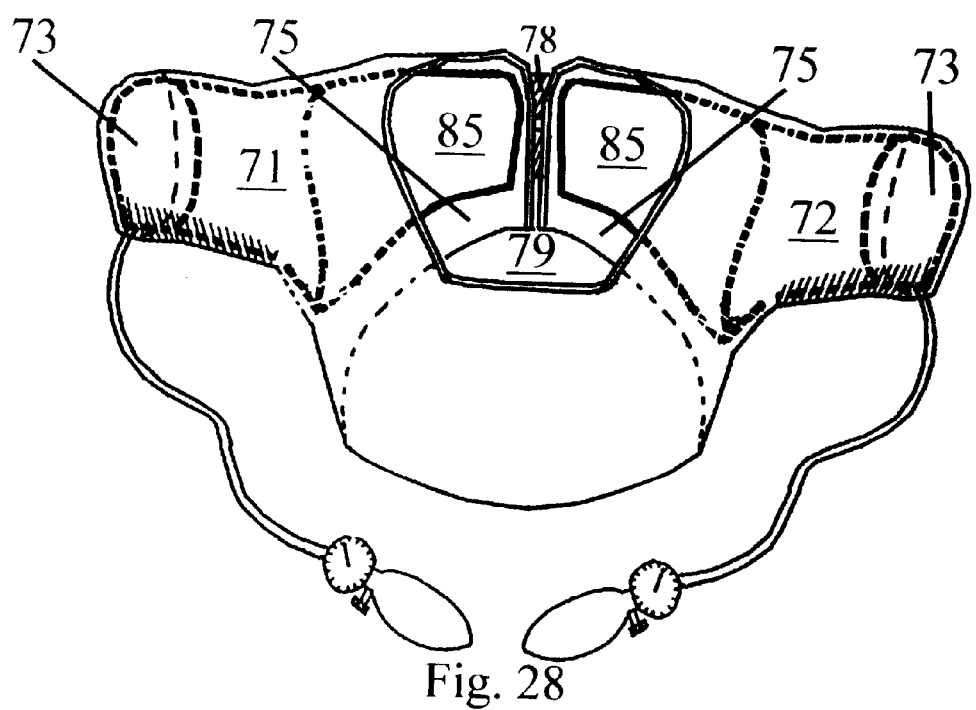
FIG. 28 is a frontal elevation view of an invention hard shell bilateral tourniquet having a one piece, back-opening, semi-flexible carapace that the wearer puts on like a hospital gown. Two fasteners (shown in cross-hatching) join the left and right sides of the back opening of the tourniquet above a bottom torso opening. Bilateral inflatable bladders for applying pressure to the wearer's bilateral shoulder areas and scapulae are shown lining the interior surface of the invention tourniquet carapace. Hidden portions of the bottom torso opening and of the bladders are shown as dotted lines.

Variations of the invention bilateral hard shell inflatable tourniquet are described with reference to FIGS. 26–28. Instead of having a carapace made of two pieces that are cinched together around the wearer, the carapace shown in FIGS. 26–28, is made of a single piece and therefore is generally semi-flexible to facilitate placing the tourniquet about the wearer. The one-piece carapace is provided with at least one opening to further facilitate application of the tourniquet to the body of the wearer. As shown in frontal view in FIG. 26, one-piece carapace 71 has slits 86 running from the underneath of each arm hole 73 to the bottom edge 87 of the carapace and a plurality of adjustable side fasteners 89 for holding the sides formed by the slit together when the tourniquet is worn. In this embodiment, the bilateral inflatable bladders 85 attached to the interior of the carapace have corresponding slit to allow opening of the carapace. The sides of the slits in the bilateral inflatable bladders are brought together and held in position by cinching of the carapace about the wearer so that the bladders substantially surround the shoulder areas of the wearer (the sides of the slits may overlap) when the side fasteners are cinched.

Figure 29:
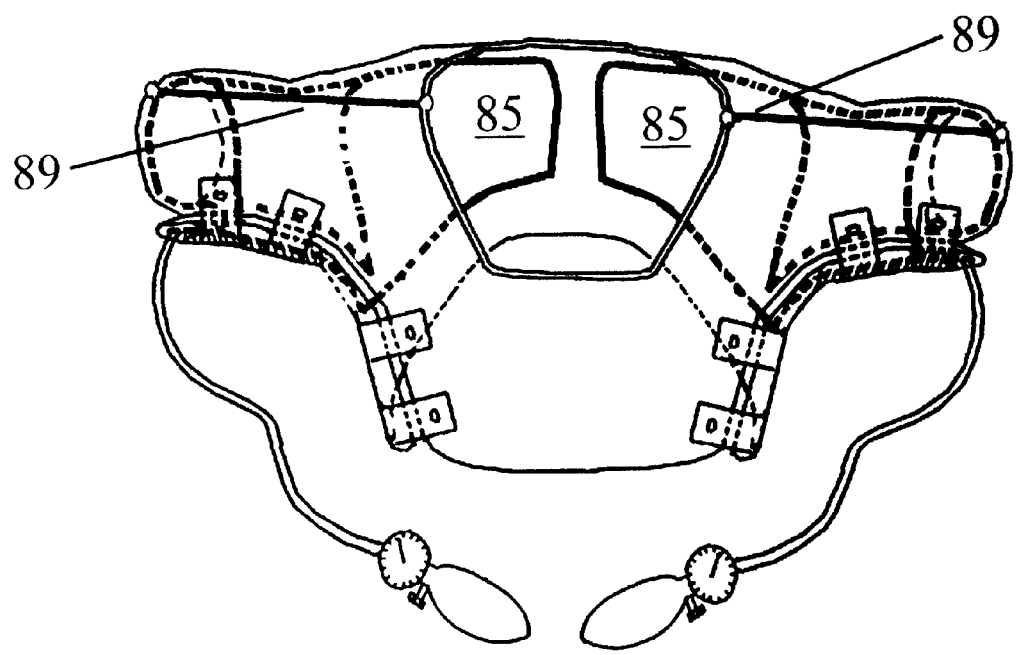
FIG. 29 is a frontal elevation view of an invention hard shell bilateral tourniquet having a two piece carapace with the two pieces hinged at the top of the shoulder and with under arm openings drawn together and cinched by a plurality of fasteners. The bottom of the carapace has a torso opening. Bilateral inflatable bladders for applying pressure to the wearer's bilateral shoulder areas and scapulae are shown lining the interior surface of the invention tourniquet carapace. Hidden portions of the bottom torso opening and of the bladders are shown as dotted lines.

Alternatively, as shown in FIG. 29, the tourniquet with an opening under each arm (described above with reference to FIG. 26) can also have a relatively inflexible carapace of two pieces that are joined by a hinging mechanism 89 along each upper shoulder. In this embodiment, the bilateral tourniquet opens like a "bivalve" and is applied over the head of the wearer. The bilateral bladders 85, also each have a slit under the arm. The edges of the slits are overlapped and then the adjustable side fasteners 89 are secured to cinch the tourniquet around the torso of the wearer before the bilateral bladders are inflated.

Figure 25:
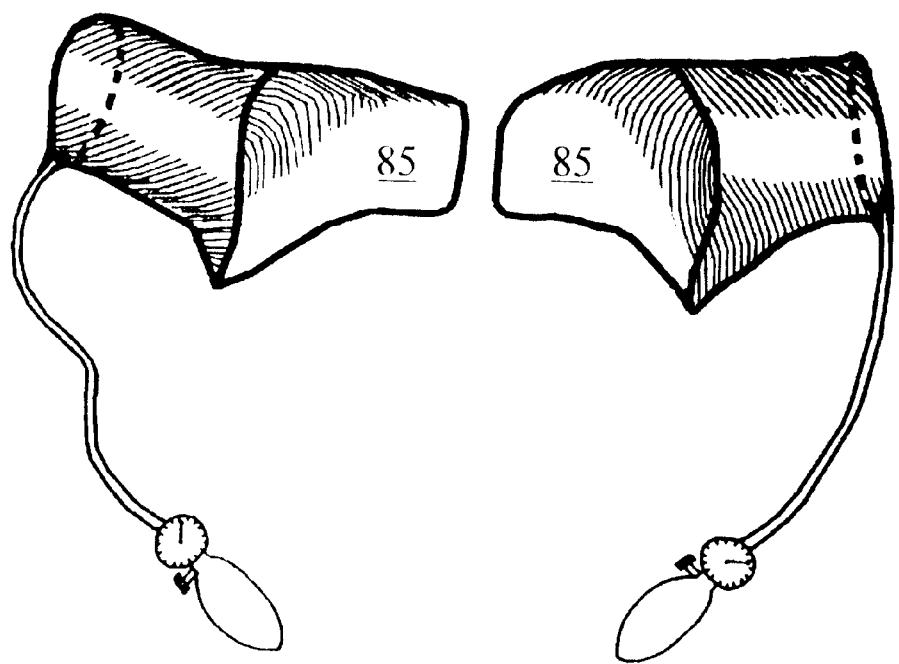
FIG. 25 is a frontal elevation view showing bilateral inflatable bladders for applying pressure to the wearer's bilateral shoulder areas and scapulae that line the interior surface of the invention tourniquet carapace of FIGS. 22–24.

In another embodiment of the invention bilateral tourniquet having a one-piece carapace, shown in FIG. 27, the sides of the carapace do not have an opening, (e.g. slits), but the carapace is semi-flexible and has a front opening such that the tourniquet has the appearance of, and can be donned by the wearer, like a vest. Adjustable fasteners 77 attached to the carapace at either side of the front opening are used to cinch the carapace about the chest of the wearer. In this embodiment, the mirror image bilateral bladders 85 attached to the interior surface of the carapace are configured as shown in FIG. 25.

In another embodiment of the invention bilateral tourniquet having a one-piece carapace, shown in FIG. 28, the carapace is semi-flexible and the opening is at the midline of the back, formed by a slit running from top to bottom of the carapace. In this embodiment, the tourniquet has the appearance of, and can be donned by the wearer, like a short, back-opening hospital gown. Adjustable back fasteners 78 attached to the carapace at either side of the back opening are used to cinch the carapace about the chest of the wearer. In this embodiment, the mirror image bilateral bladders 85 are also configured as shown in FIG. 25.

In another embodiment, the invention provides a hard shell bone marrow shielding tourniquet adapted for applying pressure to a scapular area of a human wearer. In this embodiment, the invention tourniquet comprises a substantially inflexible and inelastic carapace in one piece having a three-dimensional shape adapted to substantially cover at least the scapular area of a wearer while allowing the head, arms, and torso to protrude from the carapace, an inflatable scapular bladder attached along the interior surface of the carapace that, when inflated, applies pressure over the scapular area of the wearer, a fluid-tight connector on the inflatable bladder for inflating the bladder, and at least one adjustable fastener attached to the carapace for cinching the carapace about the torso of the wearer. Inflation of the bladder causes the tourniquet to exert sufficient pressure upon the scapular area of the wearer to occlude arterial flow thereinto.

Figure 30:
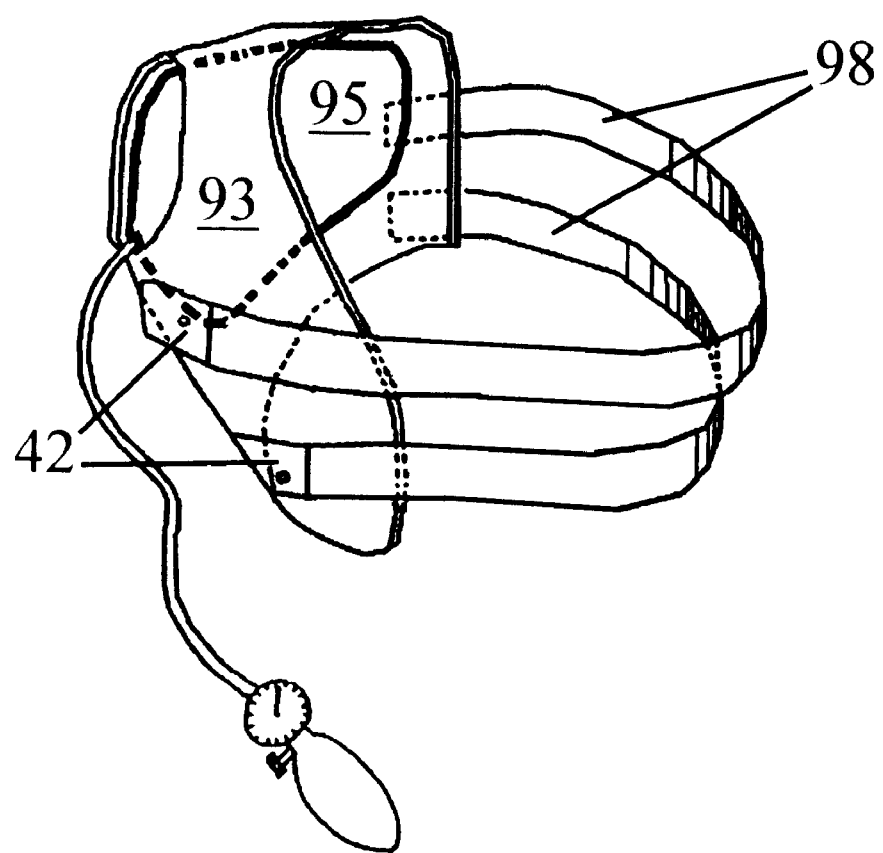
FIG. 30 is a frontal elevation view of an invention hard shell tourniquet having a one-piece inflexible carapace adapted to fit about a wearer so as to cover the scapular area (but not the shoulder cap or arm pit) and a portion of the chest. An inflatable scapular bladder for applying pressure to the triangular scapular area of a human (i.e., the shoulder blade), but not the shoulder area, is shown lining the interior surface of the carapace. Hidden portions of the bottom torso opening and of the bladders are shown as dotted lines.

As illustrated in FIG. 30 in frontal view, one-piece carapace 93 has a shape adapted to fit about a wearer so as to cover the scapular area (but not the shoulder cap or arm pit) and a portion of the chest. Inflatable scapular bladder 95, which is attached to the interior of the carapace posterior, is shaped to cover the triangular scapular area of a human (i.e., the shoulder blade), but not the shoulder area. Two adjustable and releasable fasteners 98 attach to the anterior and posterior sides of carapace 93 and are designed to loop around the torso of the wearer to cinch the inflexible carapace against the torso. When fasteners 98 (illustrated here as each including a fabric hook and loop fastener system 42) are fastened around the torso of the wearer, inflation of scapular bladder 95 according to the invention method exerts sufficient pressure upon the exterior of the scapular area of the wearer to substantially occlude arterial flow into the myelosuppresive bone marrow contained therein.

The carapace can be fabricated in several different sizes to accommodate a broad range of body builds. If the carapace is slightly too large on a patient for the inflatable bladder(s) to exert the requisite pressure to occlude arterial flow to the desired body part(s), the fit can be improved by padding carapace and/or the body part with a relatively incompressible, but flexible, padding, such as a rubber, textile, or other soft material.

The carapace is generally fabricated from a material selected from the group consisting of an artificial polymer, leather, plaster of Paris, metal, natural woven fiber, and the like, and combinations thereof. The preferred material is an artificial polymer (e.g., a plastic) such as polyethylene, poly propylene, polycarbonate, ethacrylate, acrylic, and the like, which is injection molded using techniques known in the art, to obtain a thin shell having the desired bodily shape and degree of flexibility as taught herein. Alternatively, a custom-fitted carapace can be prepared using a polymer splinting material known as Aquaplast® splinting material (Smith & Nephews, Inc.), which is softened in hot water, molded around a body part, for example, by hand, and which will harden at body temperature into a semiflexible shell, as is described in U.S. Pat. No. 4,240,415, which is incorporated herein by reference in its entirety.

In still another embodiment of the invention, a method is provided for fabricating a custom-fitted hard-shell tourniquet that is made to fit an individual patient, much as an orthopedic cast is applied to a shoulder or hip. The invention fabrication method comprises substantially covering a body part of a patient to be compressed for occlusion of arterial flow therein with one or more inflatable bladders having a fluid-tight connector; wrapping the one or more inflatable bladders with a softened orthopedic cast material so as to leave free the connectors on the bladders, and molding the cast material and inflatable bladder around the body part under conditions suitable for causing the orthopedic cast material to harden.

For comfort of the patient, the method can further comprise wrapping the body part to be compressed with a soft cushioning material, such as stockinet, cast padding (Webril®), and/or cotton sheet, prior to wrapping the one or more inflatable bladders around the body part. The cushioning material helps to decrease the pain caused by inflation of the inflatable bladder(s) and also helps to absorb moisture, such as perspiration generated by the body part during fabrication of the hard-shell tourniquet and/or during its use.

During use, the connector on the bladder is attached to a fluid source such as an air pump, and inflated to a pressure substantially above the systolic blood pressure of the patient as disclosed herein. Preferably, the connector, and/or gas source includes a mechanism for regulating gas pressure within the one or more inflatable bladders, including such parts as a pressure gauge, a pressure relief valve, and the like.

The preferred orthopedic cast material for making the invention hard shell tourniquet is a knitted substrate impregnated with polyurethane resin, for example, Delta-Lite®

Polyester Casting Tape (Johnson & Johnson), but other material, such as plaster of Paris may be used. Delta-Lite® Fiberglass Casting Tape and plaster of Paris are activated by water. As the casting tape hardens, heat is evolved, which can be felt by patient. The hard shell made from Delta-Lite® sets in approximately 3 to 5 minutes and is load-bearing in about 20 minutes after setting. Therefore, the custom-fitted hard-shell tourniquet can be used the same day as its fabrication. After completing the first session of chemotherapy using the custom-fitted hard-shell tourniquet, the custom-fitted hard-shell tourniquet may be left in place for subsequent doses after the bladder(s) are deflated, but it is preferable that the tourniquet be compressed loosely enough about the body part of interest that it can be slipped off after the chemotherapy session is completed and reused for one or more subsequent sessions. If it is not possible to slip the custom-fitted hard-shell tourniquet off from the patient, to enable its removal, the hard-shell portion of the tourniquet may be slit open using a standard cast saw so as to loosen the hard-shell. When such a use is contemplated, it is important that the inflatable bladder within the tourniquet be positioned so that it will not be slit when the hard shell is slit open. Breathing dust formed by cutting the hard shell should be avoided, as this may cause respiratory irritation or sensitization. Alternatively, the hard-shell portion may be cut "bivalved" longitudinally into "half-shells". With careful cutting of the hard-shell, preferably to avoid destroying the inflatable bladders underneath, the hard-shell can be saved and reused for subsequent doses of chemotherapy by firmly lashing the custom-fitted hard-shell tourniquet onto the patient's body.

Figure 14:
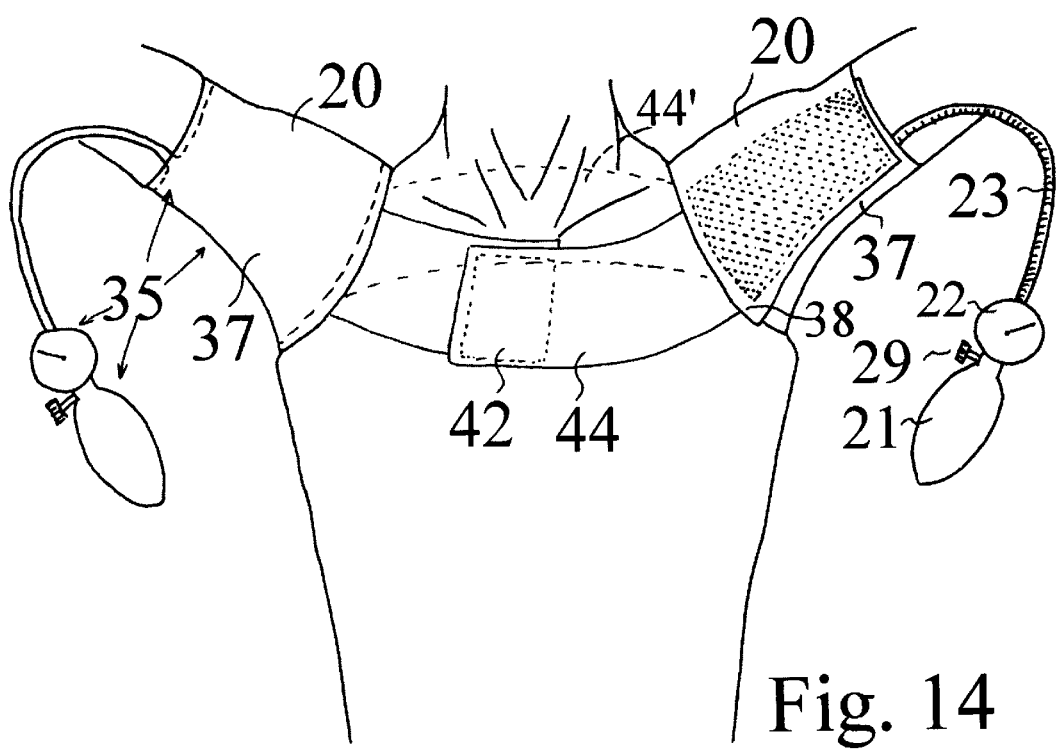
FIG. 14 is a perspective view of a "bilateral" tourniquet apparatus on both of the patient's shoulder areas, the tourniquet apparatus being fitted with a positioning belt.

FIG. 14 is a perspective view of a "bilateral" shoulder tourniquet comprising shoulder tourniquets 20 and 20' fitted on both of the patient's shoulder areas in mirror image arrangement and fitted with a releasable anterior positioning fastener for releasably joining the anterior portions of the two tourniquets, shown in FIG. 14 as belt 44. The belt 44 is sewn onto the fabric cover 38 of the shoulder tourniquet 20, and is tightly fastened with fabric hook and loop fastener system 42. Optionally, in a preferred embodiment, there is a mirror-image releasable posterior positioning fastener, shown here as belt 44' (indicated by the dotted lines behind the patient 1), that releasably joins the shoulder tourniquet across the back of the patient when the two tourniquets 20 and 20' are in place. The anterior and posterior positioning fasteners (belts 44 and 44') keep the shoulder tourniquets in position around the shoulder area of the patient and prevent migration of tourniquet away from the preferred location on the shoulder during use.

FIG. 17 is yet another embodiment of hip tourniquet 50, for placement around a patient's hip area. Hip tourniquet 50 is fitted with a tourniquet positioning fastener (illustrated here as a belt having anterior portion 51 and posterior portion 51') to keep the hip tourniquet in position around the hip and prevent migration of tourniquet away from the preferred position. As illustrated here, the positioning belt 51 is sewn onto the fabric cover 38 of the hip tourniquet 50, and is tightly fastened with fabric loop fastener 33 and fabric hook fastener 34 attached to the exterior of tourniquet 50. The hip positioning fastener is adapted to loop around the patient's pelvis to keep hip tourniquet 50 from slipping down, away from the preferred position where occlusion of the arteries supplying the proximal femur is possible. The hip tourniquet 50 further comprises bladder 37 in fluid communication with a source of fluid pressure, which is shown here as comprising air pump 21, pressure gauge 22, pressure relief valve 29, and air feed tube 23. In the embodiment shown in FIG. 17, the hip tourniquet further comprises a fastener for securing the tourniquet around the hip of the patient, such as a fabric hook and loop fastener system. FIG. 18 shows the hip tourniquet 50 of FIG. 17 about to be fastened on the hip of a patient, and FIG. 19 shows hip tourniquet 50 of FIGS. 17 and 18 now firmly fastened around the patient's hip area.

In another embodiment of hip tourniquet 50, for placement on a patient's hip area (FIG. 20), the hip tourniquet is fitted with a hip extension brace 52 that keeps the thigh extended at an angle toward the patient's torso. The hip extension brace is made of relatively inflexible material. The brace is held firmly in place by the attachment to hip tourniquet 50 as well as by the thigh belt 53.

Figure 21:
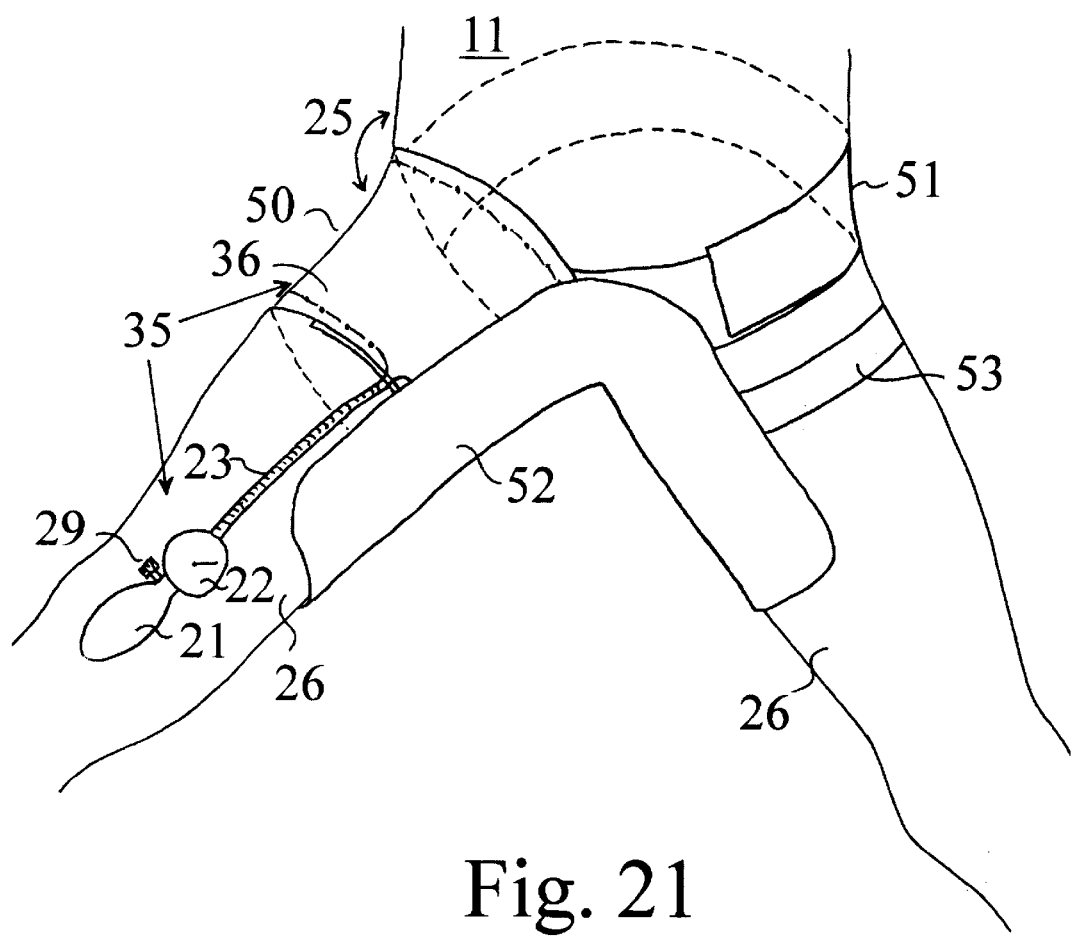
FIG. 21 is a perspective view of an invention hip tourniquet affixed around a patient's hip area, the hip tourniquet being fitted with a brace to keep the occluded leg extended at a fixed angle toward the patient's torso.

FIG. 21 is another perspective view of hip tourniquet fitted with a hip extension brace now shown firmly fastened on the patient's hip area. The hip tourniquet 50 is fitted with a hip extension brace 52, that keeps the thigh extended at an angle toward the patient's torso. The hip extension brace is made of relatively inflexible material. The brace is held firmly in place by the attachment to hip tourniquet 50 as well as by the thigh belt 53. The angle, 25, formed by the patient's thigh, 26, and the patient's torso, 11, is generally between about 45 degrees and about 155 degrees, for example, between about 75 degrees and about 155 degrees, and most preferably between about 90 degrees and about 145 degrees.

The invention will now be described in greater detail by reference to the following non-limiting examples.

EXAMPLE 1

A central line catheter by subclavian or jugular approach is placed in a patient with cancer if the patient is to undergo bilateral shoulder tourniquet procedure. Alternately, a peripheral intravenous line is placed in a neck vein (external jugular), taking care that the catheter does not get dislodged at any time during the entire procedure. If the patient is to undergo a unilateral shoulder tourniquet procedure, a central line catheter or intravenous line in the neck are not necessary since chemotherapy can be infused into the contralateral arm. On the day of chemotherapy, a complete blood count, and test of levels of serum Creatinine, Bilirubin, Serum Glutamic Oxaloacetic Transaminase (SGOT), Serum Glutamic Pyruvic Transaminase (SGPT), and alkaline phosphatase are performed. The white blood cell count should be higher than 4000 per cu. mm., and the platelet count should be higher than 100,000 per cu. mm.

Prior to application of a tourniquet, the patient is premedicated with 1 mg of lorazepam given orally or intravenously for anxiety, 10 mg of ondansetron intravenously for nausea/vomiting, and 100 mg of meperidine, or equivalent, intravenously for pain. Webril® is applied to the upper arm and shoulder area to protect the skin, and the tourniquet is placed over the Webril® to cover the shoulder area, making certain that the entire shoulder or hip area is encircled by the tourniquet. The extremity to be occluded is exsanguinated using an Esmarch bandage and/or gravity drainage, then the tourniquet is inflated to a pressure high enough to substantially occlude, and preferably completely occlude, the covered arteries, which is at least 5 to 10 mmHg above systolic blood pressure, preferably at the limb, for example 5 to 300 mmHg above systolic blood pressure, or between 50 to 200 mmHg above systolic blood pressure, and preferably about 100 mmHg above systolic blood pressure. Alternately, pressure of 280 mmHg may be used. The Esmarch bandage is removed and the absence of radial artery pulsation is determined.

0.4 mg/kg of body weight mechlorethamine is injected through the central line catheter. Five minutes to 2 hours, for example 5 minutes to 1 hour, and preferably 5 minutes to 15 minutes following the administration of the chemotherapeutic agent, the tourniquet is deflated.

EXAMPLE 2

The following is an example of process of using the invention tourniquet to occlude arterial flow into the upper leg so that the bone marrow within the femur, tibia, fibula, ankle bones, and feet bones are not exposed to high concentration of cytotoxic chemotherapeutic drugs.

The procedure described in Example 1 above is followed except that the patient is administered 40 µg/kg of body weight of granisetron intravenously for nausea/vomiting and the Webril® is applied to the upper leg and buttock area to protect skin prior to placing the tourniquet around the hip area and the absence of pulse is determined in the dorsalis pedis artery.

As chemotherapeutic agent, 10 mg mechlorethamine is injected intravenously and 5 minutes to 2 hours, for example 5 minutes to 1 hour, and preferably 5 minutes to 15 minutes, following the administration of the chemotherapeutic agent, the tourniquet is deflated.

EXAMPLE 3

Prior to the administration of chemotherapy, the patient is given 10 µg/kg/day of granulocyte-colony stimulating factor (G-CSF or filgrastim) daily by subcutaneous injections to stimulate the bone marrow. The patient's white blood cell count (WBC) is monitored during this period to avoid producing too high a WBC count. About 24 hours following the final dose of G-CSF, the patient undergoes chemotherapy as described in Examples 1 or 2 herein.

EXAMPLE 4

The procedure described in Example 3 above is followed except that prior to administration of chemotherapy in the place of G-CSF the patient is administered 5 µg/kg body weight/day of granulocyte macrophage-colony stimulating factor (GM-CSF) daily by subcutaneous injection for 2 to 10 days to stimulate the bone marrow.

EXAMPLE 5

The procedure described in Example 3 or 4 above is followed except that the cytokine administered prior to the administration of chemotherapy is 100 µg of stem cell factor (SCF) daily by subcutaneous injection for 2 to 10 days.

EXAMPLE 6

In place of G-CSF, GM-CSF, or SCF administration as in Examples 3, 4, and 5, erythropoietin (EPO), thrombopoietin (TPO), IL-12, or other cytokines are given prior to, during, or after the administration of chemotherapy to stimulate bone marrow.

EXAMPLE 7

The procedure described in Example 1 above is followed except that the patient's arm is chilled to extend the time that the arterial flow is occluded to the arm. Prior to application of the Webril®, the arm to be occluded is chilled to a skin temperature of about 5 to about 35° C., for example, to a skin temperature of about 15 to about 25° C., and preferably to a skin temperature of about 18 to about 22° C., using "cold packs" (Riker 3M) or a cooling blanket with circulating chilled water. Once the desired temperature is attained, Webril® is applied and the procedure of Example 1 is carried out while continuing to chill the arm except that the pressure is maintained on the shoulder area for about 5 minutes to 2 hours, for example 5 minutes to 1 hour, and preferably 5 minutes to 15 minutes, following the administration of the chemotherapeutic agent, before the tourniquet is deflated and the cooling blanket or cooling packs are removed.

EXAMPLE 8

The procedure described in Example 8 above is followed except that the atient's leg is chilled rather than an arm, and the tourniquet is applied around the hip area rather than around the shoulder area.

EXAMPLE 9

This example illustrates an embodiment of the invention method wherein the patient's blood is collected for oxygenation prior to application of the tourniquet and the oxygenated blood is administered to the occluded body part as a means of safely extending the period of occlusion. The procedure described in Example 1 above is followed, except as follows: Prior to exsanguination, a standard blood collection bag is prepared for collecting autologous whole blood by first injecting 100 ml of pure oxygen gas into the bag. Then a portion of a preservative-anticoagulant solution, such as ACD (acid-citrate-dextrose), CPD (citrate-phosphate-dextrose), or CPDA-1 (CPD with adenine), which is generally already in the bag, is removed so that 14-15 ml of the solution remains in the blood collection bag for each 100 ml of whole blood to be collected.

A blood collection needle is inserted into the arm of the patient to undergo bone marrow shielding, and about 100 to about 300 ml of the patient's own (i.e. autologous) blood is then collected into the bag prior to premedication of the patient for pain, anxiety, and the like, and prior to application of the tourniquet.

The collection bag containing the blood is placed upon a continuously tilting machine to gently mix the blood with pure oxygen gas so that each 100 ml of whole blood absorbs as much blood as possible, up to a maximum of about 20 ml of pure oxygen gas. The needle through which the autologous blood is collected is kept in place, later to be used for transfusion of the oxygenated blood back into the same arm.

About thirty minutes or about one hour after the tourniquet is applied, the autologous blood collected previously and exposed to pure oxygen gas is infused back into the patient's arm while the tourniquet remains inflated. At about 90 minutes to about 2 hours following the application of the tourniquet, the tourniquet is deflated.

EXAMPLE 10

This example illustrates a procedure for neutralizing the myelosuppresive effect of a chemotherapeutic agent used in practice of the invention method before the pressure is removed from the occluded body part, allowing administration of an increase in the dosage of the chemotherapeutic agent.

The procedure described in Example 1 above is followed except that as follows: The patient is administered 10 mg of mechlorethamine as an intravenous bolus dose through the central line catheter as the chemotherapeutic agent. Fifteen minutes following the administration of the chemotherapeutic agent, 1000 mg of sodium thiosulfate is administered intravenously. Three to five minutes after administration of the sodium thiosulfate dose, the tourniquet is deflated.

EXAMPLE 11

This example illustrates the use of 5-azacitidine, a nucleoside analogue that has somewhat narrow spectrum of activity compared to nitrogen mustard, in the invention bone marrow shielded chemotherapy method. The procedure described in Example 1 above is followed except that the patient is administered 200 mg/m$^2$ of 5-azacitidine, intravenously as the chemotherapeutic agent, and the pressure on the occluded body part is maintained from about 10 minutes to 2 about hours, for example, about 15 minutes to about 1 hour, and preferably about 15 minutes to about 30 minutes, following the administration of the chemotherapeutic agent.

EXAMPLE 12

The following example illustrates use of doxorubicin, a DNA intercalator with very rapid initial half-life (5 min) followed by longer terminal half-life (10 hr), in the invention bone marrow-shielded chemotherapy method. The procedure described in Example 1 above is followed except that the patient is premedicated with 2 mg of granisetron intravenously for nausea/vomiting, and 1 to 2 mg of hydromorphone intravenously for pain. Doxorubicin in an amount of 50 mg/m$^2$ of body surface treated is administered intravenously as the chemotherapeutic agent, and 30 minutes to 1 hour following the administration of the chemotherapeutic agent, the tourniquet is deflated.

EXAMPLE 13

The following example illustrates use of 5-fluorouracil in the invention bone arrow-shielded chemotherapy method. The procedure described in Example 1 above is followed except for the following: The patient is premedicated with 1 mg of lorazepam orally or intravenously for anxiety, ondansetron is omitted since 5-FU does not cause significant nausea/vomiting, and 100 mg of meperidine is given intravenously for pain. 5-fluorouracil is administered intravenously as the chemotherapeutic agent at a dosage of 300 mg/m$^2$ of treated body surface, and the tourniquet is deflated 30 minutes following the administration of the chemotherapeutic agent. This procedure is repeated daily for a total of 5 days.

EXAMPLE 14

An alternate method of using 5-fluorouracil in the invention method follows the procedure of Example 13 except that the 5-fluorouracil is administered together with leucovorin, a folate vitamin that potentiates 5-fluorouracil. The procedure in Example 15 is followed, except that the patient is administered 370 mg/m$^2$ of 5-fluorouracil plus 20 mg/m$^2$ of leucovorin in the place of the daily 5-fluorouracil of Example 13.

EXAMPLE 15

The procedure described in Example 1 above is followed except that administration of ondansetron is omitted since dactinomycin does not cause significant nausea/vomiting and as the chemotherapeutic agent the patient is administered 5-dactinomycin intravenously at a dosage of 2 mg/m$^2$ of body surface. Thirty minutes following the administration of the chemotherapeutic agent, the tourniquet is deflated.

EXAMPLE 16

The procedure described in Example 15 above is followed except that the chemotherapeutic agent administered intravenously is mitomycin-C at a dosage of 10 g/m$^2$ of body surface treated and the tourniquet is deflated about 30 minutes to 1 hour following the administration of the chemotherapeutic agent.

EXAMPLE 17

The procedure described in Example 15 above is followed except that as the chemotherapeutic agent the patient is intravenously administered streptozocin at a dosage of 10 mg/m$^2$ of body surface treated and the tourniquet is deflated about 30 minutes to 1 hour following the administration of the chemotherapeutic agent.

EXAMPLE 18

The procedure described in Example 1 above is followed except that the patient is intravenously administered 50 mg/m$^2$ of body surface of mitoxantrone as the chemotherapeutic agent. About 30 to about 60 minutes following administration of the chemotherapeutic agent, the tourniquet is deflated.

EXAMPLE 19

The procedure described in above example 18 is followed, except that 200 mg/m$^2$ of body surface of BCNU is used in place of mitoxantrone in Example 18.

EXAMPLE 20

The procedure described in above example 13 is followed, except that 30 mg/m$^2$ of body surface of cytarabine is used in place of 5-FU in Example 13.

EXAMPLE 21

The procedure described in above example 18 is followed, except that 5 mg/m$^2$ of body surface of melphalan is used in place of mitoxantrone in Example 18.

EXAMPLE 22

The procedure described in Example 18 above is followed except that the patient s administered 0.2 mg/kg of body weight of thiotepa in place of mitoxantrone in Example 18.

EXAMPLE 23

The procedure described in above example 18 is followed, except that 200 mg/m$^2$ of treated body surface of DTIC is used in place of mitoxantrone in Example 18.

EXAMPLE 24

The procedure described in Example 1 above is followed except that as the chemotherapeutic agent the patient is administered as the following chemotherapeutic agents according to the following schedule, each administration with the tourniquet in place: 600 mg/m$^2$ of body surface of 5-FU (weekly), 50 mg/m$^2$ of body surface of doxorubicin (every 4 weeks), and 10 mg/m$^2$ of body surface of mitomycin-C (every 8 weeks), through the central line catheter. For each dosage, 15 minutes to 2 hours, but preferably 30 minutes to 2 hours, and most preferably 30 minutes to 1 hour, following the administration of the chemotherapeutic agent, the tourniquet is deflated.

EXAMPLE 25

The procedure described in above Example 24 is followed, except that 0.5 mg/kg of body weight of mechlorethamine is used in place of mitomycin-C in Example 24.

EXAMPLE 26

The procedure described in above Example 24 is followed, except that 0.5 mg/kg of body weight of mechlorethamine, and 2 mg/m$^2$ of body surface of dactinomycin are substituted for mitomycin-C and doxorubicin in Example 24.

EXAMPLE 27

The procedure described in above Example 24 is followed, except that 45 mg/m$^2$ of body surface of mitoxantrone and 0.4 mg/kg of body weight of thiotepa are substituted for doxorubicin, mitomycin, and 5-FU.

EXAMPLE 28

The procedure described in Example 1 above is followed except that as the chemotherapeutic agent the patient is administered by injection a combination of chemotherapeutic agents, such as 0.3 mg/kg of body weight of mechlorethamine (every weeks), 50 mg/m$^2$ of body surface of doxorubicin (every 4 weeks), and 375 mg/m$^2$ of body surface of DTIC (every 2 weeks), through the central line catheter. For each dosage, 15 minutes to 2 hours, but preferably 30 minutes to 2 hours, and most preferably 30 minutes to 1 hour, following the administration of the chemotherapeutic agent, the tourniquet is deflated. Separately from the tourniquet procedure, the remaining drug in this combination regimen, 1.5 mg/m$^2$ of body surface (maximum of 2 mg) of vincristine is administered weekly throughout the regimen. The vincristine is administered separately without application of the tourniquet, since this drug causes minimal damage to bone marrow.

EXAMPLE 29

The procedure described in Example 28 above is followed except that as the chemotherapeutic agent a combination of 50 mg/m$^2$ of body surface of doxorubicin and 50 mg/m$^2$ of body surface of cisplatin is administered instead of mechlorethamine, doxorubicin, and DTIC, and vincristine is omitted.

EXAMPLE 30

The procedure described in Example 28 above is followed, except that the combination of chemotherapeutic agents administered is 200 mg/m$^2$ of body surface of BCNU and 2 mg/m$^2$ of body surface of dactinomycin instead of mechlorethamine, doxorubicin, and DTIC in Example 28, and vincristine is administered as in Example 28.

EXAMPLE 31

The procedure described in above example 28 is followed, except that the combination of chemotherapeutic agents administered is 0.3 mg/kg of body weight of mechlorethamine, 50 mg/m$^2$ of doxorubicin and 50 mg/m$^2$ of body surface of cisplatin instead of mechlorethamine, doxorubicin, and DTIC and vincristine is omitted.

EXAMPLE 32

The procedure described in Example 1 above is followed except that as the chemotherapeutic agent used during the tourniquet procedure, the patient is administered 6 mg/m$^2$ of body surface of mechlorethamine intravenously and the tourniquet is applied (on days 1 and 8 of a 14 day regimen). Fifteen minutes to 2 hours, but preferably 30 minutes to 2 hours, and most preferably 30 minutes to 1 hour, following the administration of the intravenous chemotherapeutic agent, the tourniquet is deflated.

In addition, further chemotherapeutic agents are administered separately from the tourniquet procedure as follows. On days 1 and 8 of the 14 day regimen, at least 30 2 minutes to 60 minutes prior to the above shoulder tourniquet procedure, 1.4 mg/m$^2$ of body surface (maximum of 2 mg) of vincristine are administered intravenously; and on days 1 through 14 of the 14 day regimen, 100 mg/m$^2$ of body surface of procarbazine and 40 mg/m$^2$ of body surface of prednisone are administered orally.

EXAMPLE 33

The procedure described in above Example 32 is followed, except that 25 mg/m$^2$ of body surface of doxorubicin, 6 mg/m$^2$ of body surface of vinblastine, and 375 mg/m$^2$ of body surface of DTIC are substituted for mechlorethamine of Example 32. In the place of vincristine, procarbazine, and prednisone given separately from the tourniquet procedure in Example 32, bleomycin is administered separately from the tourniquet procedure at a dosage of 10 mg/m$^2$ of body surface.

EXAMPLE 34

The procedure described in above Example 32 is followed, except that 750 mg/m$^2$ of body surface of cyclophosphamide and 50 mg/m$^2$ of body surface of doxorubicin are substituted for mechlorethamine of Example 32. The three drugs (i.e. vincristine, procarbazine, and prednisone) given separately from the tourniquet procedure in Example 34, are substituted by 1.4 mg/m$^2$ of body surface (maximum of 2 mg) of vincristine and 60 mg/m$^2$ of body surface of prednisone (per oral daily for 5 days).

EXAMPLE 35

The procedure described in above Example 32 is followed, except that 25 mg/m$^2$ of body surface of doxorubicin (given on days 1 and 8) and 650 mg of cyclophosphamide (given on days 1 and 8) are substituted for mechlorethamine of Example 32. The three drugs (i.e. vincristine, procarbazine, and prednisone) given separately from the shoulder tourniquet procedure in Example 32, are substituted by bleomycin, 5 units/m$^2$ of body surface (given on days 15 and 22), vincristine 1.4 mg/m$^2$ of body surface (maximum of 2 mg, given on days 1 and 8), and 60 mg of prednisone (given daily from day 15 to 28).

EXAMPLE 36

The procedure described in above Example 32 is followed, except that 50 mg/m$^2$ of body surface of doxorubicin, 500 mg/m$^2$ of body surface of 5-fluorouracil (given on days 1 and 8), and 500 mg/m$^2$ of body surface of cyclophosphamide are substituted for mechlorethamine of Example 32. The three drugs (i.e. vincristine, procarbazine, and prednisone) given separately from the tourniquet procedure in Example 32, are omitted.

EXAMPLE 37

The procedure described in above Example 32 is followed, except that 45 mg/m$^2$ of body surface of doxorubicin, and 500 mg/m$^2$ of body surface of cyclophosphamide are substituted for mechlorethamine of Example 32. The three drugs (i.e. vincristine, procarbazine, and prednisone) given separately from the tourniquet procedure in Example 32, are omitted.

EXAMPLE 38

The procedure described in above Example 32 is followed, except that 10 mg/m² of body surface of mitomycin-C (given on days 1 and 22, then every 6 weeks) and vindesine 3 mg/m² of body surface (given weekly for 5 times, then every 2 weeks) are substituted for the mechlorethamine of Example 32. The three drugs (i.e. vincristine, procarbazine, and prednisone) given separately from the tourniquet procedure in Example 32, are omitted.

EXAMPLE 39

The procedure described in above Example 32 is followed, except that 8 mg/m² of body surface of mitomycin-C (given on days 1, 29, and 71 only), vindesine 3 mg/m² of body surface (given weekly for 5 times, then every 2 weeks), and cisplatin 120 mg/m² of body surface (given on days 1, 29, then every 6 weeks) are substituted for mechlorethamine of Example 32. The three drugs (i.e. vincristine, procarbazine, and prednisone) given separately from the tourniquet procedure in Example 32, are omitted.

EXAMPLE 40

The procedure described in above Example 32 is followed, except that 8 mg/m² of body surface of mitomycin-C (given on days 1, 29, and 71 only), vinblastine 4.5 mg/m² of body surface (given weekly for 5 times, then every 2 weeks), and cisplatin 120 25 mg/m² of body surface (given on days 1, 29, then every 6 weeks) are substituted for mechlorethamine of Example 32. The three drugs (i.e. vincristine, procarbazine, and prednisone) given separately from the tourniquet procedure in Example 32, are omitted.

EXAMPLE 41

The procedure described in above Example 32 is followed, except that 8 mg/m² of body surface of mitomycin-C (given on days 1, 29, and 71 only), vinblastine 4.5 mg/m² of body surface (given weekly for 5 times, then every 2 weeks), and cisplatin 120 mg/m² of body surface (given on days 1, 29, then every 6 weeks) are substituted for mechlorethamine of Example 32. The three drugs (i.e. vincristine, procarbazine, and prednisone) given separately from the tourniquet procedure in Example 32, are omitted.

EXAMPLE 42

The procedure described in above Example 32 is followed, except that 45 mg/m² of body surface of doxorubicin, 50 mg/m² of body surface of etoposide (given daily for 5 days), and 1000 mg/m² of body surface of cyclophosphamide are substituted for the mechlorethamine of Example 32. The three drugs (i.e. vincristine, procarbazine, and prednisone) given separately from the tourniquet procedure in Example 32, are omitted.

EXAMPLE 43

The procedure described in above Example 32 is followed, except that 1000 mg/m² of body surface of cyclophosphamide and 45 mg/m² of body surface of doxorubicin are substituted for the mechlorethamine of Example 32. The three drugs (i.e. vincristine, procarbazine, and prednisone) given separately from the tourniquet procedure in Example 32, are substituted by 1.4 mg/m² of body surface (maximum of 2 mg) of vincristine.

EXAMPLE 44

The procedure described in above Example 32 is followed, except that 1000 mg/m² of body surface of cyclophosphamide and 50 mg/m² of body surface of doxorubicin are substituted for the mechlorethamine of Example 32. The three drugs (i.e. vincristine, procarbazine, and prednisone) given separately from the tourniquet procedure in Example 32, are substituted by 1.4 mg/m² of body surface (maximum of 2 mg) of vincristine and 60 mg/m² of body surface of etoposide (given daily for 5 days).

EXAMPLE 45

A human study was performed to assess the effectiveness of a shoulder tourniquet for transiently occluding blood supply to bone marrow of a humerus. An invention shoulder tourniquet was applied to the right shoulder of a human adult male and inflated to 280 mm Hg. Eight millicuries of technetium-99m sulfur colloid was then injected intravenously into the contralateral left arm vein. A gamma camera (Model NXT Maxi Camera 400 AC) with LEAP collimator was used to monitor blood perfusion to the head, neck, and bilateral upper arms. With the tourniquet inflated, images were collected every minute for the first 20 minutes, beginning 1 minute following the injection, with 60 seconds of accumulated exposure for each image. At 20 minutes post injection, the tourniquet was deflated to restore the pressure on the occluded shoulder to atmospheric pressure, and then at the 22 minute point another image was collected over a 60 second period. In total, 64×64 images were processed and stored in a Sophy computer system.

Visual examination of the images showed that inflation of the invention shoulder tourniquet to 280 mm Hg is very effective for transiently occluding arterial flow into the humerus bone, including the upper ⅓ of the humerus while perfusion to the head and contralateral arm was unimpaired. The images also show that within two minutes of deflation of the tourniquet, perfusion was reestablished in the treated shoulder and arm.

EXAMPLE 46

This example illustrates the utility of the invention bone marrow shielding tourniquet during administration of a standard dose of mechlorethamine (0.4 mg/kg) to a human patient with breast cancer. This patient responded favorably to the invention method of treatment by having decreased pain in her back even though the mechlorethamine was administered at a dosage no higher than the standard dosage.

The patient (Patient # 1), a 46 year old female, had been diagnosed two years earlier as having a high-grade lobular carcinoma (5×3×3 cm) in the left breast with invasion of capillary and lymphatic vessels (38 of 41 axillary nodes were positive for cancer). A mastectomy was performed followed by chemotherapy with 6 cycles of CEF (epirubicin, 5-FU, and cyclophosphamide). The patient also received radiation therapy to the left chest wall and axilla. Approximately two years post-radiation and chemotherapy, the patient was found to have metastatic recurrence to spine, pelvis and lung. In treatment of the recurrence, the patient received 2500 rads of x-ray radiation over 5 weeks to T10-L2 spine and to right coxofemoral joint, followed by two cycles of chemotherapy with CEF. Because of the high total dose of epirubicin, the patient could receive no further CEF chemotherapy. At the time of enrollment in treatment using the invention method and device, the patient was experiencing back pain of level 2 on a 10 level pain scale.

In the first cycle of treatment according to the invention, a standard dose of 0.4 mg/kg of body weight of mechlorethamine was administered without use of the invention bone marrow shielding tourniquet. As premedication the patient received intravenously 16 mg dexamethasone and 2 mg Kytril and 1 mg lorazepam orally. Then the dose of mechlorethamine was administered intravenously without bone marrow shielding and without GM-CSF. The nadirs of the patient's white blood count (WBC), absolute neutrophil count (ANC), and platelet count were 1200 (day 12), 840 (day 12), and 48,000 cells/cu mm (day 15), respectively. By day 22, the patient's WBC (white blood count), ANC (absolute neutrophile count), and platelet count recovered to 4000, 3400, and 164,000 cells/cu mm, respectively and the patient reported symptomatic improvement of back pain after the first cycle.

In a second cycle of treatment, a bone marrow shielded standard dose mechlorethamine was administered 31 days after the first cycle of treatment. An invention bone marrow shielding tourniquet was applied to the right humerus at a pressure of 260 mm/Hg for 15 minutes, while a dose of 0.4 mg/kg of body weight of mechlorethamine was administered in the left arm vein. The nadirs of the patient's WBC, ANC, and platelet count were 1000 (day 10), 600 (day 12), and 20,000 cells/cu mm (day 17), respectively. By day 19 post second cycle treatment, the patient's WBC, ANC, and platelet count had recovered to 3100, 1860, and 54,000 cells/cu mm, respectively.

In a third cycle of treatment 35 days after the second cycle of treatment, an invention bone marrow shielding tourniquet was applied to bilateral humeri and one scapula at 260 mm Hg for 4 minutes and then 180 mm Hg for 11 minutes while the standard dose of mechlorethamine was administered through a Groshong catheter inserted into the right subclavian vein. The nadirs of the patient's WBC, ANC, and platelet count were 900 (day 12), 459 (day 12), and 19,000 cells/cu mm (day 19), respectively. By day 22, patient's WBC, ANC, and platelet count recovered to 3200, 2240, and 26,000 cells/cu mm, respectively.

In a fourth cycle of treatment 28 days after the third cycle of treatment, an invention bone marrow shielding tourniquet was applied to bilateral humeri and one scapula at 260 mm Hg for 4 minutes and then 180 mm Hg for 11 minutes while the standard dose of mechlorethamine was administered through a Groshong catheter inserted into the right subclavian vein. The nadirs of the patient's WBC, ANC, and platelet count were 500 (day 12), 360 (day 12), and 17,000 cells/cu mm (day 23), respectively. By day 30, the patient's WBC, ANC, and platelet count had recovered to 3350, 2546, and 150,000 cells/cu mm, respectively.

EXAMPLE 47

In this Example, a patient (patient #2) with brain cancer, a notoriously difficult tumor to treat with chemotherapy, was treated using the invention method and apparatus. Patient # 2, a 49 year old female, had been diagnosed with high-grade glioma of the right hemisphere of the brain about four and a half years earlier. At that time she underwent a craniotomy and subsequently received radiation therapy to the brain over a period of 5 weeks. Patient #2 did well for about 51 months, but thereafter experienced convulsions and vomiting. Upon examination, the patient was found to have a recurrence and was treated by a second resection of the glioma via a craniotomy. At the time of enrollment in the present treatment regimen, patient #2 had no symptoms except for a mild weakness in her left arm and a healed craniotomy scar from ear to ear on her scalp.

In the first cycle of chemotherapy according to the present invention, patient #2 was administered 16 mg dexamethasone intravenously, and 2 mg Kytril and 1 mg lorazepam orally as premedications. Then 0.4 mg/kg of body weight of mechlorethamine was administered intravenously into the right arm vein in standard fashion without the use of the invention bone marrow shielding tourniquet. The nadirs of the patient's WBC, ANC, and platelet count were 2100, 300, and 174,000 cells/cu mm, respectively, the first two occurring on day 17 and the last occurring on day 12. By day 19, the patient's WBC, ANC, and platelet count had recovered to 3000, 1000, and 332,000 cells/cu mm, respectively.

In a second cycle of treatment 21 days after the first cycle of treatment, an invention bone marrow shielding tourniquet was applied only to the patient's right humerus at 260 mm Hg pressure and the doses of medication of the first cycle were repeated. The nadir of the patient's WBC, ANC, and platelet count were 1100 (day 15), 266 (day 17), and 135,000 cells/cu mm (day 12), respectively. By day 19, the patient's WBC, ANC, and platelet count had recovered to 2300, 825, and 249,000 cells/cu mm, respectively.

A third cycle of treatment was administered on days 18 and 19 following completion of the second cycle at twice the standard dose using the invention bone marrow shielding tourniquet and with a supplemental administration of GM-CSF.

Patient #2 was premedicated with 8 mg dexamethasone IV, 16 mg dexamethasone IV, and 2 mg Kytril, 1 mg lorazepam, and 0.3 mg of buprenorphine orally. Then, the invention bone marrow shielding tourniquet was applied to the patient's bilateral humeri and bilateral scapulae at a pressure of 260 mm Hg prior to administration of 0.4 mg/kg of body weight of mechlorethamine given IV through a Groshong catheter placed into the patient's left subclavian vein. The bone marrow shielding tourniquet was kept inflated for 15 minutes following the injection of mechlorethamine, except for the left scapula bladder, which was deflated 3 minutes after injection of mechlorethamine. This regimen of chemotherapy was repeated the next day for a total of 2 days. On day 2, Patient #2 was started on a daily supplemental dosage of 400 μg of GM-CSF subcutaneously for a total of 14 days. The nadirs of the patient's WBC, ANC, and platelet count were 1000 (day 11), 580 (day 15), and 36,000 cells/cu mm (day 17), respectively. By day 19 post-treatment, the patients WBC and platelet count had recovered to 2500 and 69,000 cells/cu mm, respectively.

In the fourth cycle of treatment, started 35 days after commencement of the third cycle, the patient was premedicated with 8 mg of dexamethasone IV, and 16 mg of Zofran IV, 2 mg of lorazepam orally, 0.3 mg of buprenorphine IV, and Benadryl 20 mg IV. The invention bone marrow shielding tourniquet was applied to bilateral humeri and bilateral scapulae for 15 minutes at 280 mmHg while 0.4 mg/kg of body weight of mechlorethamine was administered through a Groshong catheter as above. This regimen of chemotherapy was repeated the next day for a total of 2 days. The patient was not given any GM-CSF until she developed fever, which was successfully managed with an outpatient IV antibiotic and daily subcutaneous GM-CSF. The nadirs of the patient's WBC, ANC, and platelet count were 300 (day 13), 0 (day 15), and 9,000 cells/cu mm (day 22), respectively. By day 22, the patient's WBC and ANC had recovered to 1400 and 1232 cells/cu mm, respectively. CT scan of brain showed a substantial decrease in tumor size.

EXAMPLE 48

In this Example, a patient with rectal cancer, another very difficult type of cancer to treat with chemotherapy, receives one cycle of mechlorethamine with Bone marrow shielding tourniquet applied to one humerus and two cycles of mechlorethamine with Bone marrow shielding tourniquet applied to bilateral humeri and bilateral scapulae, all given without GM-CSF.

Patient # 3, a 48 year old male, had been diagnosed three years prior as having adenocarcinoma of the rectum. At that time, a resection of the rectal cancer was performed with an anastomosis of the rectum. About three years post-surgery, the patient had symptoms of recurrence and was found to have a large tumorous mass in the rectum, which was determined to be unresectable due to its size. Instead, the patient was administered radiation therapy at 5000 rads to the pelvis in 20 fractions and two months later underwent diverting colostomy for 70% obstruction of the rectum caused by the very large size of the tumor remaining after the radiation therapy. At the time of enrollment in the present treatment regimen, patient #3 was suffering from pain in the rectum and took Darvon for the pain.

Some three months after the colostomy, in a first cycle of treatment according to the present invention, an intravenous line was place in right arm vein and patient #3 was administered 16 mg dexamethasone IV, and 2 mg Kytril and 1 mg lorazepam orally as premedications followed by 0.4 mg/kg of body weight of mechlorethamine IV while an invention bone marrow shielding tourniquet was applied to left humerus alone at 260 mm Hg for 15 minutes. No GM-CSF was given. The nadirs of the patient's WBC and ANC were 2900 (day 15), 1537 cells/cu mm (day 15), respectively. By day 19 post-treatment, the patient's WBC and ANC had recovered to 3000, and 1890 cells/cu mm, respectively.

In the second cycle administered 41 days later, patient #3 was administered 16 mg dexamethasone IV, and 2 mg Kytril orally, 1 mg lorazepam orally, and 0.3 mg of buprenorphine IV as premedications. An invention bone marrow shielding tourniquet was applied to the patient's bilateral humeri and bilateral scapulae at a pressure of 260 mm Hg while 0.4 mg/kg of body weight of mechlorethamine (twice the standard dose) was given IV through a Groshong catheter placed into patient's right subclavian vein. The bone marrow shielding tourniquet was kept inflated for 15 minutes following the injection of mechlorethamine. This chemotherapy regimen was repeated the next day for a total of 2 days. Patient #3 was not given any GM-CSF. The nadirs of the patient's WBC, ANC, and platelet count were 1800 (day 19), 918 (day 19), and 130,000 cells/cu mm (day 22), respectively. By day 26 post-treatment, the patient's WBC, ANC, and platelet count had recovered to 2700, 1863 and 240,000 cells/cu mm, respectively. After the second cycle, the patient's rectal pain was completely resolved and the patient was able to return to work as a mechanic. CT (computerized axial tomography) scan showed "no disease" whereas previous CT scan had shown very large tumor obstructing the rectum.

In a third cycle of treatment commencing 37 days after the second cycle, the patient was administered 8 mg dexamethasone IV, and 16 mg Zofran IV, 2 mg Ativan, 20 mg Benadryl orally, but no buprenorphine, as premedication, and a standard dose of 0.4 mg/kg of body weight of mechlorethamine was given IV through the Groshong catheter with the invention bone marrow shielding tourniquet applied to bilateral humeri and bilateral scapulae at 280 mm/Hg for 15 minutes on the right side, but only 4 minutes on the left side. On the second day of the third cycle, the chemotherapy was repeated with the invention bone marrow shielding tourniquet applied to bilateral humeri and scapulae for 15 minutes. The nadirs of the patient's WBC, ANC, and platelet count were 2300 (day 10), 1372 (day 15), and 170,000 cells/cu mm (day 21), respectively. By day 31 post-treatment, the patient's WBC, ANC, and platelet count had recovered to 4800, 2448, and 225,000 cells/cu mm, respectively.

Some two weeks after the third cycle of treatment, the patient underwent sigmoidoscopy, which showed markedly smaller tumor mass. As a result, the patient was presented at a local tumor board and a recommendation was made to have the patient undergo resection of the tumor, which was successfully performed.

The resected surgical specimen showed only necrotic mass without any detectable cancer under microscopic histopathology examination.

EXAMPLE 49

The next example is a very young patient with breast cancer, who developed metastatic disease after receiving standard surgical and chemotherapeutic treatments. She received her first cycle of mechlorethamine at 4 times the standard dose (0.4 mg/kg of body weight×4) with the Bone marrow shielding tourniquet applied to bilateral humeri and bilateral scapulae and daily GM-CSF for 21 days. The patient tolerated chemotherapy well with a degree and duration of myelosuppression that was equivalent to that associated with standard dose mechlorethamine.

Patient # 4, a 28 year old female, had been diagnosed with breast cancer involving almost all of the right breast about two years prior. At that time the patient underwent preoperative chemotherapy with Cytoxan, 5-FU, and epirubicin (120 mg/sq m) for 4 cycles, with partial response (80%), followed by modified radical mastectomy about one year post-diagnosis. Patient #4 had more than 10 positive lymph nodes and received post-operative radiation therapy to her chest wall.

Following the mastectomy, the patient had an additional 4 cycles of the chemotherapy, except with a lower dose of epirubicin (80 mg/sq m). The patient started to have back pain within a few months and underwent radiation therapy to the spine for 10 days. The pain improved and the patient had a slight pain in her back at the time of enrollment in the present treatment regimen. However, one month later, patient #4 was found to have liver metastases, multiple lesions, on both lobes, as diagnosed by ultrasound. At the time of enrollment (about five months after radiation therapy), patient #4 also had numerous 0.5 cm to 1 cm hard skin nodules over the right chest wall (over the mastectomy site).

In a first cycle of chemotherapy according to the invention, patient #4 was administered 8 mg dexamethasone IV, and 16 mg Zofran IV, 1 mg lorazepam, 0.3 mg of buprenorphine and 30 mg of benadryl orally as premedications. A bone marrow shielding tourniquet was applied to the patient's bilateral humeri and bilateral scapulae at a pressure of 280 mm Hg while 0.4 mg/kg of body weight of mechlorethamine was administered IV through a Hickman catheter placed into patient's left subclavian vein. The invention one marrow shield was kept inflated for 15 minutes following the injection of mechlorethamine. This chemotherapy was repeated daily through Hickman catheter for a total of 4 days. On the second day of chemotherapy, patient #4 was started on a daily subcutaneous dose of GM-CSF (400 μg) for 21 days. The nadirs of the patient's WBC, ANC, and platelet count were 400, 164, and 14,000 cells/cu mm, respectively, all occurring on day 14. By day 19, patient's WBC, ANC, and platelet counts had partially recovered to 1800, 1170, and 22,000 cells/cu mm, respectively.

EXAMPLE 50

The patient in this example, a breast cancer patient who developed metastatic disease after receiving standard surgical and chemotherapeutic treatments, received her first cycle of mechlorethamine at 4 times the standard dose (0.4 mg/kg of body weight×4) with the invention bone marrow shielding tourniquet applied to bilateral humeri and bilateral scapulae and daily GM-CSF for 13 days. The patient tolerated chemotherapy well with a degree and duration of myelosuppression that was much milder than that associated with standard doses of mechlorethamine that are administered without bone marrow shielding according to the invention method. In addition, the tumor mass on the patient's skull almost disappeared after one cycle of the invention chemotherapy with the bone marrow shielding tourniquet.

Patient #5 is a 54 year old female who had been diagnosed with an advanced stage of cancer (6×4 cm in size) of the left breast about two years prior. At that time the patient underwent preoperative chemotherapy with Cytoxan, 5-FU and epirubicin at regular dose for 3 cycles, with a partial response, followed by modified radical mastectomy some four months later. As 29 of 30 of the lymph nodes were positive for cancer, following the mastectomy, patient had radiation therapy to the left chest wall and left axilla with some skin damage from radiation. An additional 3 cycles of Cytoxan, 5-FU and epirubicin were given post-operatively. The patient's surgeon tried to implant a silicon prosthesis, but the implant was not successful so the breast prosthesis was eventually removed. About 26 months after the mastectomy, the patient developed pain in her left leg. A bone scan showed multiple metastatic lesions in pelvis, ribs, and skull. The patient consequently received radiation to her hips in fractions, resulting in improvement of the pain.

At the time of enrollment in the present study, the patient used a cane to walk with slight pain in her left hip area and was taking Tamoxifen and prednisone at mg every other day. There was darkened skin with a linear horizontal scar over the mastectomy site, with apparent radiation burn, resulting in some dried exudate from the scar. In addition, the patient had a firm and slightly tender tumorous mass (3 cm×3.5 cm) over the left parietal bone of her skull.

A first cycle of chemotherapy according to the present invention was commenced about 29½ months after the mastectomy. An invention bone marrow shielding tourniquet was applied to the patient's bilateral humeri and bilateral scapulae at a pressure of 280 mm Hg while 0.4 mg/kg of body weight of mechlorethamine was given IV through a Hickman catheter placed into patient's right subclavian vein. The bone marrow shielding tourniquet was kept inflated for 15 minutes following the injection of mechlorethamine. This chemotherapy regimen was repeated daily through a Hickman catheter for a total of 4 days. On the third day of chemotherapy, the patient was started on a daily dose of GM-CSF (400 μg subcutaneously) for 13 days. The nadirs of the patient's WBC, ANC, and platelet count were 2100 (day 8), 1197 (day 8), and 90,000 cells/cu mm (day 15), respectively. By day 17, the patient's WBC, ANC, and platelet count recovered to 3900, 2379, and 99,000 cells/cu mm, respectively. After the first cycle of chemotherapy with the bone marrow shielding tourniquet in place, the patient's tumor mass in her left parietal bone of skull has almost disappeared.

It will be apparent to those skilled in the art that various changes may be made in the invention without departing from the spirit and scope thereof, and therefore, the invention encompasses embodiments in addition to those specifically disclosed in the specification, but only as indicated in the appended claims.

What is claimed is:

1. A method for bone marrow-shielded chemotherapeutic treatment of a patient in need thereof, said method comprising:

applying pressure to at least one body part of the patient to temporarily occlude arterial flow to the bone marrow within the proximal humerus and/or proximal femur while blood circulation through the remainder of the body is maintained, administering to the blood circulation in the remainder of the body an effective amount of at least one myelosuppresive chemotherapeutic agent while the arterial flow through the at least one body part is occluded and so that the myelosuppresive effect of the agent is substantially dissipated within the maximum safe period for the occlusion of the arterial flow, and removing the pressure to restore blood circulation to the bone marrow when the effect has substantially dissipated and within the maximum safe period, wherein a tumor located in the remainder of the body is treated by the at least one chemotherapeutic agent without destruction of a substantial portion of the bone marrow in the at least one body part, and without general anesthesia.

2. A method for bone marrow-shielded chemotherapeutic treatment of a patient in need thereof, said method comprising:

applying a bone marrow shielding tourniquet to cover at least one body part of the patient so as to temporarily occlude arterial flow to the bone marrow to temporarily occlude arterial flow to the bone marrow within the proximal humerus and/or proximal femur while blood circulation through the remainder of the body is maintained, administering to the blood circulation in the remainder of the body an effective amount of at least one myelosuppresive chemotherapeutic agent and while the arterial flow through the at least one body part is occluded until the myelosuppresive effect of the agent is substantially dissipated within the maximum safe period for the occlusion of the arterial flow, and removing the bone marrow shielding tourniquet to restore blood circulation to the bone marrow when the effect has substantially dissipated and within the maximum safe period.

3. The method according to claim 2 wherein the chemotherapeutic agent has a known period of initial half-life and the tourniquet is removed about 1 minute to about 2 hours after passage of the known period of initial half life.

4. The method according to claim 2 wherein the method is practiced without general anesthesia and the maximum safe period is about three hours.

5. The method according to claim 3 wherein the known period of initial half-life is about 10 seconds to about 25 minutes and the removing of the tourniquet is about 15 minutes after passage of the known period of initial half life.

6. The method according to claim 2 wherein the tourniquet applies a pressure substantially greater than the systolic blood pressure of the patient.

7. The method according to claim 6 wherein the pressure is from about 5 mmHg to about 300 mmHg above the systolic blood pressure.

8. The method according to claim 7 wherein the pressure is from about 50 mmHg to about 200 mmHg above the systolic blood pressure.

9. The method according to claim 2 wherein the pressure is substantially equalized over the body surface covered by the tourniquet.

10. The method according to claim 2 wherein the method is repeated at spaced intervals of from eight hours to two months.

11. The method according to claim 10 wherein the repeating is for up to 20 repeats.

12. The method according to claim 2 wherein the arterial flow is occluded for a period of from about 5 minutes to about 2 hours.

13. The method according to claim 2 wherein the body part is a shoulder and/or a hip and the method further comprises exsanguinating the arm proximal to the shoulder and/or leg proximal to the hip prior to application of the tourniquet.

14. The method according to claim 13 wherein the exsanguinating involves applying an Esmarch bandage or gravity drainage of the arm or leg.

15. The method according to claim 2 wherein the tourniquet is inflatable and the applying involves inflation of the tourniquet to apply the pressure around the at least one body part.

16. The method according to claim 2 wherein the at least one body part is a shoulder and the tourniquet occludes arterial flow into the proximal humerus of the patient.

17. The method according to claim 15 wherein the at least one body part includes both shoulders and the tourniquet occludes arterial flow into the proximal humeri of the patient.

18. The method according to claim 2 wherein the at least one body part includes a hip and the tourniquet occludes arterial flow into the proximal femur of the patient.

19. The method according to claim 17 wherein the at least one body part includes both hips and the tourniquet occludes arterial flow into the respective proximal femurs of the patient.

20. The method according to claim 2 wherein the at least one body part includes a scapula of the patient.

21. The method according to claim 2 wherein the at least one body part includes both scapulae of the patient.

22. The method according to claim 2 further comprising administering to the patient an effective amount of one or more active agents for relieving pain, anxiety, nausea or vomiting.

23. The method according to claim 22 wherein the one or more active agents are administered before the tourniquet is applied.

24. The method according to claim 2 wherein the chemotherapeutic agent is cytotoxic against the type of tumor being treated.

25. The method according to claim 24 wherein the chemotherapeutic agent is mechlorethamine and the effective amount is in the range from about 0.1 mg/kg to about 1.6 mg/kg of body weight of the patient.

26. The method according to claim 25 wherein the effective amount is in the range from about 0.2 mg/kg to about 0.6 mg/kg of body weight of the patient.

27. The method according to claim 25 wherein the tumor is associated with a cancer selected from the group consisting of Hodgkin's disease, lymphoma, sarcoma, and skin, lung, breast, brain, colon, rectal, uterine, stomach, liver, kidney, pancreas, prostate, testicular and ovarian cancer.

28. The method according to claim 2 wherein the method further comprises administering highly oxygenated autologous blood into the occluded body part while the tourniquet is applied.

29. The method according to claim 2 wherein the method further comprises chilling the occluded body part during at least a portion of the time during which the tourniquet is applied.

30. The method according to claim 2 wherein the body part includes both shoulders and wherein the method further comprises administering the chemotherapeutic agent via a central venous catheter.

31. The method according to claim 1 further comprising administering to the patient an effective amount of a cytokine selected from the group consisting of Granulocyte-colony stimulating factor, granulocyte-macrophage-colony stimulating factor, stem cell factor, erythropoietin, thrombopoietin, interleukin-11, and suitable combinations thereof.

32. A method for fabricating an individualized bone marrow shielding tourniquet, said method comprising:
(a) wrapping a hip or shoulder to be compressed for occlusion of arterial blood flow therein with an inflatable bladder having a fluid-tight connector,
(b) wrapping the inflatable bladder with a softened orthopedic cast material so as to leave free the connector, and
(c) molding the cast material and the one or more inflatable bladders around the hip or shoulder under conditions suitable for causing the orthopedic cast material to harden.

33. The method according to claim 32 wherein the method further comprises wrapping the shoulder or hip to be compressed with a cushioning material prior to wrapping the one or more inflatable bladders around the hip or shoulder.

34. The method according to claim 33 wherein the cushioning material is moisture absorbent.

35. The method according to claim 33 wherein the cushioning material is stockinet, cast padding, or cotton sheet, or a combination thereof.

36. The method according to claim 34, wherein the orthopedic cast material is a knitted substrate impregnated with polyurethane resin or plaster of Paris.

37. A method for protecting myelopoietic marrow cells from the effects of chemotherapeutic agents without the need for physical removal of bone marrow cells from the body of a patient in need thereof, said method comprising:
applying substantially uniform pressure of from 5 mmHg to about 300 mmHg above the systolic blood pressure around at least one body part including the proximal humerus and/or femur of the patient to temporarily occlude arterial flow to the bone marrow therein while blood circulation through the remainder of the body is maintained,
administering to the blood circulation in the remainder of the body an effective amount of at least one myelosuppresive chemotherapeutic agent while the arterial flow through the at least one body part is occluded and so that the myelosuppresive effect of the agent is substantially dissipated within about three hours of commencement of the application of the pressure, and
removing the pressure to restore blood circulation to the bone marrow when the effect has substantially dissipated and within the three hours.

38. The method according to claim 37 further comprising administering to the patient an effective amount of a cytokine selected from the group consisting of Granulocyte-colony stimulating factor, granulocyte-macrophage-colony stimulating factor, stem cell factor, erythropoietin, thrombopoietin, interleukin-11, and suitable combinations thereof.

39. The method according to claim 38 further comprising administering the chemotherapeutic agent to the via a central venous catheter.

40. The method according to claim 39 wherein the catheter is placed into a vein selected from the group consisting of internal jugular, external jugular, and subclavian veins.

* * * * *